US012692650B2

(12) United States Patent
Bridewell et al.

(10) Patent No.: US 12,692,650 B2
(45) Date of Patent: Jul. 28, 2026

(54) WATER SOLUBLE FIBERS WITH POST PROCESS MODIFICATIONS AND ARTICLES CONTAINING SAME

(71) Applicant: MONOSOL, LLC, Merrillville, IN (US)

(72) Inventors: Victoria Bridewell, Merrillville, IN (US); Nicholas Zeese, Merrillville, IN (US); Richard Goetz, Merrillville, IN (US); Jonathon Knight, Merrillville, IN (US); Alyssa Shuey, Merrillville, IN (US)

(73) Assignee: MONOSOL, LLC, Merrillville, IN (US)

( * ) Notice: Subject to any disclaimer, the term of this patent is extended or adjusted under 35 U.S.C. 154(b) by 911 days.

(21) Appl. No.: 18/000,372

(22) PCT Filed: Jun. 2, 2021

(86) PCT No.: PCT/US2021/035448
§ 371 (c)(1),
(2) Date: Nov. 30, 2022

(87) PCT Pub. No.: WO2021/247705
PCT Pub. Date: Dec. 9, 2021

(65) Prior Publication Data
US 2023/0220613 A1 Jul. 13, 2023

Related U.S. Application Data

(60) Provisional application No. 63/033,601, filed on Jun. 2, 2020.

(51) Int. Cl.
| | |
|---|---|
| *D06M 13/144* | (2006.01) |
| *A61F 13/15* | (2006.01) |
| *D01F 8/16* | (2006.01) |
| *D04H 1/4309* | (2012.01) |
| *D04H 1/435* | (2012.01) |
| *D04H 3/007* | (2012.01) |
| *D06M 11/38* | (2006.01) |
| *D06M 23/10* | (2006.01) |
| *D06M 101/24* | (2006.01) |
| *D06M 101/30* | (2006.01) |

(52) U.S. Cl.
CPC ..... *D06M 13/144* (2013.01); *A61F 13/15211* (2013.01); *D01F 8/16* (2013.01); *D04H 1/4309* (2013.01); *D04H 1/435* (2013.01); *D04H 3/007* (2013.01); *D06M 11/38* (2013.01); *D06M 23/10* (2013.01); *D06M 2101/24* (2013.01); *D06M 2101/30* (2013.01); *D10B 2401/024* (2013.01)

(58) Field of Classification Search
CPC .... D06M 13/144; D06M 11/38; D06M 23/10; D06M 2101/24; D06M 2101/30; A61F 13/15211; D01F 8/16; D01F 8/00; D04H 1/4309; D04H 1/435; D04H 3/007; D04H 3/011; D10B 2401/024; C08F 116/06; C08F 216/06; C08J 3/12; A61L 15/62; A61L 15/24; A61L 15/42
See application file for complete search history.

(56) References Cited

U.S. PATENT DOCUMENTS

| | | | | |
|---|---|---|---|---|
| 4,258,849 A | * | 3/1981 | Miller ..................... | D04H 1/64 442/166 |
| 4,366,206 A | | 12/1982 | Tanaka | |
| 5,410,037 A | | 4/1995 | Wagner et al. | |
| 6,191,193 B1 | | 2/2001 | Lee et al. | |
| 6,521,246 B2 | | 2/2003 | Sapieszko et al. | |
| 6,872,696 B2 | | 3/2005 | Becker et al. | |
| 2002/0003106 A1 | | 1/2002 | Takeuchi et al. | |
| 2005/0205574 A1 | | 9/2005 | Lambotte et al. | |
| 2006/0261516 A1 | | 11/2006 | Kunitake et al. | |
| 2010/0018641 A1 | | 1/2010 | Branham et al. | |
| 2011/0189413 A1 | | 8/2011 | Denome et al. | |
| 2017/0042143 A1 | | 2/2017 | Burakowska-Meise et al. | |

FOREIGN PATENT DOCUMENTS

| | | | |
|---|---|---|---|
| EP | 1048722 B1 | 6/2005 | |
| JP | S46-36489 B | 12/1971 | |
| JP | S53-74195 A | 7/1978 | |
| JP | H06145441 A | 5/1994 | |
| JP | H8-284021 A | 10/1996 | |
| KR | 20100027568 A | 3/2010 | |
| KR | 101652567 B1 | 8/2016 | |
| KR | 10-1861038 B1 | 5/2018 | |
| KR | 101861038 | * | 5/2018 |
| WO | 2016137293 A1 | 5/2018 | |

(Continued)

OTHER PUBLICATIONS

Rejection Decision issued in Chinese Patent Application No. 202180045774.4, dated Apr. 7, 2025.
Examination Report issued in Australian patent application No. 2021285853, issued Nov. 8, 2023.
Office Action issued in Japanese patent application No. 2022-572334, mailing date Feb. 6, 2024.
First Examination Report issued in Indian Patent Application No. 202217067280, dated May 2, 2024.
Office Action issued in Chinese Patent Application No. 202180045774. 4, dated May 13, 2024.
International Search Report and Written Opinion for PCT/US2021/035448 issued Sep. 8, 2021.
Extended European Search Report issued in European Patent Application No. 24195726.5, dated Dec. 18, 2024.

(Continued)

*Primary Examiner* — Kumar R Bhushan
(74) *Attorney, Agent, or Firm* — Benesch Friedlander Coplan & Aronoff LLP

(57) ABSTRACT

A method of treating a fiber includes admixing a fiber comprising a polymer comprising at least one of a vinyl acetate moiety or a vinyl alcohol moiety and having a degree of hydrolysis less than 100% with a hydrolysis agent solution to form a mixture so as to increase the degree of hydrolysis of at least a portion of the fiber.

43 Claims, 13 Drawing Sheets

(56) References Cited

FOREIGN PATENT DOCUMENTS

WO          2021247705 A1      12/2021

OTHER PUBLICATIONS

Lee, Young Jae et al: "Preparation of monodisperse poly(vinyl alcohol) (PVA) nanoparticles by dispersion polymerization and heterogeneous surface saponification", Fibers and Polymers, The Korean Fiber Society, Seoul, vol. 17, No. 4, Apr. 29, 2016 (Apr. 29, 2016), pp. 502-511, XP035718114, ISSN: 1229-9197, DOI: 10.1007/S12221-016-5892-2.

Seok, Lyoo Won et al: "Preparation of Syndiotactic Poly(vinyl alcohol)/Poly(vinyl pivalate/vinyl acetate) Microspheres with Radiopacity Using Suspension Copolymerization and Saponification", Jan. 1, 2010, pp. 389-391, XP093227955, DOI: 10.1063/1.3455646; Retrieved from the Internet: URL: https://pubs.aip.org/aip/acp/article/1255/1/389/868697/Preparation-of-Syndiotact ic-Poly-vinyl-alcohol [retrieved on Nov. 26, 2024].

Peixoto, Luciana S et al: "Synthesis of Spherical Core-Shell PVAc—co—PMMA/PVA Particles for Use in Vascular Embolization", Macromolecular Symposia, [Online] vol. 299-300, No. 1, Jan. 1, 2011, pp. 32-138, XP093227960, DEISSN: 1022-1360, DOI: 10.1002/masy.200900152Retrieved from the Internet:URL:https://api.wiley.com/onlinelibrary/td m/v1/articles/10.1002%2Fmasy.200900152>, [retrieved on Nov. 26, 2024].

Office Action issued in Chinese Patent Application No. 202180045774. 4, dated Jan. 9, 2025.

Extended European Search Report issued in European Patent Application No. 21817632.9, dated Sep. 19, 2024.

Examination Report issued in Australian Patent Application No. 2021285853, dated Oct. 3, 2024.

Official Action issued in Japanese Patent Application No. Patent application 2022-572334, dated Nov. 19, 2024.

* cited by examiner (A)    (B)    (C)    (D)

stand collar rod

WATER SOLUBLE FIBERS WITH POST PROCESS MODIFICATIONS AND ARTICLES CONTAINING SAME

PRIORITY CLAIM AND CROSS-REFERENCE

This application is a U.S. national stage application under 35 U.S.C. § 371 of International Application No. PCT/US2021/035448, filed Jun. 2, 2021, which claims the benefit under 35 U.S.C. § 119(e) of U.S. Provisional Application No. 63/033,601, filed Jun. 2, 2020, the entire disclosures of which are hereby incorporated by reference.

FIELD

The present disclosure relates generally to water soluble fibers. More particularly, the disclosure relates to water soluble fibers comprising polyvinyl alcohol modified after fiber formation by hydrolysis.

BACKGROUND

Nonwoven webs are traditionally used in many single-use consumer products including personal care products, such as bandages, diaper components, feminine care, and adult incontinence, and single-use wipes, such as in industrial applications, medical applications, cleaning applications, and personal/baby care. Traditional chemistries used in such products, e.g., viscose, polypropylene, or cotton fibers, are generally non-sustainable, non-biodegradable, are potential contributors to microplastics, and are often disposed of incorrectly, such as by flushing down a toilet and entering wastewater treatment and sewage facilities. Known wipes must be disposed of in a bin, which may not be hygienic or convenient for a user. Improper disposal of these articles can result in pipe clogs in the home, formation of "fatbergs" or aggregation of congealed mass of biodegradable and non-biodegradable materials composed of congealed grease and cooking fat and disposable wipes in residential and munici-pal wastewater systems, contributing to oceanic microplas-tics, and require a change in consumer behavior.

The solubility profile and mechanism (e.g., hot-water soluble vs. cold-water soluble, readily soluble vs. delayed solubility or extended release) of a water-soluble article may need to be adjusted based on the end use of the article. For articles including water-soluble fibers, the solubility profile and mechanism are generally varied by selecting fiber forming materials having a degree of hydrolysis or degree of polymerization. However, the degree of hydrolysis and degree of polymerization of fiber forming materials also influence the ability of the fiber forming material to form fibers. Thus, a fiber formed of a particular polymer having a desired degree of hydrolysis and degree of polymerization to provide a fiber having a desired solubility profile may not be accessible as the fiber forming material may not survive the fiber making process.

SUMMARY

One aspect of the disclosure provides a method of treating a fiber including a hydrolyzable polymer such as a polymer comprising at least one of a vinyl acetate moiety or a vinyl alcohol moiety having a degree of hydrolysis of less than 100%, the method including admixing the fiber and a hydrolysis agent solution to increase the degree of hydro-lysis of at least a portion of the polymer in the fiber.

Another aspect of the disclosure provides a method of treating a fiber including a hydrolyzable polymer such as a polymer comprising at least one of a vinyl acetate moiety or a vinyl alcohol moiety having a degree of hydrolysis of less than 100%, the method including contacting a surface of the fiber with a hydrolysis agent solution to increase the degree of hydrolysis of the polymer at in a region of the fiber comprising at least the surface of the fiber.

Another aspect of the disclosure provides a fiber prepared according to the methods of the disclosure.

Another aspect of the disclosure provides a fiber having a surface region and an interior region, the fiber comprising a hydrolyzable polymer a polymer comprising at least one of a vinyl acetate moiety or a vinyl alcohol moiety and the fiber having a transverse cross-section characterized by the poly-mer of the surface region having a greater degree of hydro-lysis than the polymer of the interior region. Optionally, the transverse cross-section of the fiber is characterized by an increasing gradient in the degree of hydrolysis of the poly-mer from the interior region to the surface region.

Another aspect of the disclosure provides a fiber com-prising a transverse cross-section characterized by a core-sheath structure, also referred to as a core-shell structure, the fiber having a first, core region, comprising a hydrolyzable polymer such as a polymer comprising at least one of a vinyl acetate moiety or a vinyl alcohol moiety having a degree of hydrolysis less than 100%, a second, shell region, compris-ing such a polymer having a degree of hydrolysis greater than the polymer of the first region.

Another aspect of the disclosure provides a method of treating a nonwoven web comprising a plurality of fibers comprising a hydrolyzable polymer such as a polymer comprising at least one of a vinyl acetate moiety or a vinyl alcohol moiety having a degree of hydrolysis of less than 100%, the method including contacting at least a portion of the nonwoven web with a hydrolysis agent solution to increase the degree of hydrolysis of the polymer of the fibers of the portion of the nonwoven web.

Another aspect of the disclosure provides a nonwoven web treated according to the methods of the disclosure.

Another aspect of the disclosure provides a nonwoven web comprising a fiber of the disclosure.

Another aspect of the disclosure provides a multilayer nonwoven web comprising a first layer comprising a non-woven web treated according to the methods of the disclo-sure or a nonwoven web comprising a fiber of the disclosure.

Another aspect of the disclosure provides a pouch com-prising a nonwoven web according to the disclosure in the form of a pouch defining an interior pouch volume.

Another aspect of the disclosure provides a sealed article comprising a nonwoven web of the disclosure.

Another aspect of the disclosure provides a flushable article comprising a nonwoven web of the disclosure.

Another aspect of the disclosure provides a wearable absorbent article, the article comprising an absorbent core having a wearer facing side and an outer facing side and a liquid acquisition layer, wherein the liquid acquisition layer comprises a nonwoven web of the disclosure.

Further aspects and advantages will be apparent to those of ordinary skill in the art from a review of the following detailed description. While the fibers, nonwoven webs, pouches, articles and their methods of making a susceptible of embodiments in various forms, the description hereafter includes specific embodiments with the understanding that the disclosure is illustrative and is not intended to limit the invention to the specific embodiments described herein.

BRIEF DESCRIPTION OF THE DRAWINGS

For further facilitating the understanding of the present disclosure, fourteen (14) drawing figures are appended hereto.

DETAILED DESCRIPTION

Figure 1:
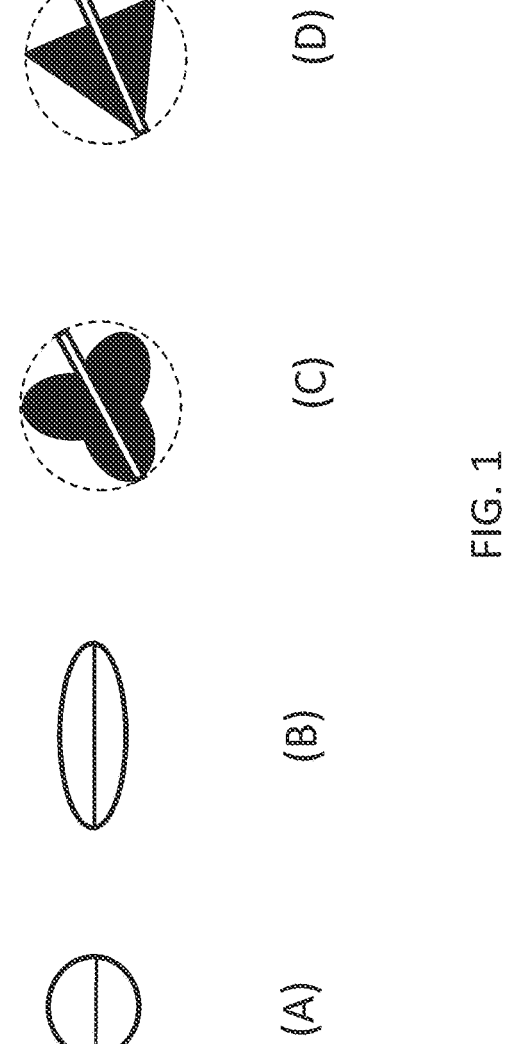
FIGS. 1A-1D show a transverse cross-section of various fiber shapes, wherein the line indicates the diameter of the fiber.

As described in the Background, a fiber formed of a particular polymer having a desired degree of hydrolysis and degree of polymerization to provide a fiber having a desired solubility profile may not be accessible because the fiber forming material may not survive the fiber making process. Accordingly, it would be advantageous to provide a method for modifying the solubility profile of a fiber after fiber formation in order to access otherwise unavailable solubility profiles.

Additionally, as the solubility profile of a fiber or a water-soluble article prepared therefrom can be designed for a particular end use, it would be advantageous to provide a method for modifying the solubility profile of a fiber after fiber formation in order to manage inventory. The ability to post-process modify the degree of hydrolysis and, thus, the solubility profile of a fiber would advantageously allow access to various fiber types starting from one or a plurality of fiber types.

Provided herein are methods of treating fibers or a surface thereof to increase the degree of hydrolysis of a hydrolyzable polymer that makes up the fiber or a surface thereof, by contacting the fiber or surface thereof with a hydrolysis agent solution. The methods of the disclosure can advantageously provide a fiber having an increase in the average degree of hydrolysis of a hydrolyzable polymer that makes up the fiber, a fiber having a core-sheath structure wherein the polymer of the sheath or surface region has a greater degree of hydrolysis than the polymer of the core or interior region, and/or a fiber having an increasing gradient of the degree of hydrolysis of the polymer that makes up the fiber, from an interior region to a surface region. Optionally, the hydrolyzable polymer comprises at least one of a vinyl acetate moiety or a vinyl alcohol moiety. As used herein, "at least one of a vinyl acetate moiety or a vinyl alcohol moiety" and "a vinyl acetate moiety and/or a vinyl alcohol moiety" describe an example hydrolyzable polymer comprising only a vinyl acetate moiety, only a vinyl alcohol moiety, or both a vinyl acetate moiety and a vinyl alcohol moiety. In embodiments, the fibers of the disclosure are water-soluble prior to treatment with the hydrolysis agent solution and remain water-soluble after treatment with the hydrolysis agent solution. In embodiments, the fibers of the disclosure are cold-water soluble prior to treatment with the hydrolysis agent solution and are hot-water soluble after treatment with the hydrolysis agent solution. In embodiments, the fibers of the disclosure are cold-water soluble prior to treatment with the hydrolysis agent solution and at least a portion of the exterior surface of the fiber is hot-water soluble after treatment with the hydrolysis agent solution. In embodiments, the fiber is not water-soluble prior to treatment with the hydrolysis agent solution and the fiber is water-soluble after treatment with the hydrolysis agent solution. In embodiments, the fiber is not water-soluble after admixing the fiber with the hydrolysis agent.

The methods and fibers of the disclosure can provide one or more advantages, including but not limited to, providing control over the microstructure of the a fiber, modifying the solubility profile and/or mechanism of a fiber, enhancing the chemical compatibility of a fiber to a chemical agent, increasing the absorbance capacity of a fiber, increasing and/or controlling the loading of an active to the interior of a fiber, and/or providing control over the release of a composition or active from the interior of a fiber.

As used herein and unless specified otherwise, the term "water-soluble" refers to any nonwoven web or article containing same having a dissolution time of 300 seconds or less at a specified temperature as determined according to MSTM-205 as set forth herein, or any fiber having complete dissolution time of less than 30 seconds at a specified temperature according to the method for determining single fiber solubility disclosed herein. For example, the solubility parameters can be characteristic of a nonwoven web having a thickness of 6 mil (about 152 μm), or an article made therefrom. The dissolution time of the nonwoven web optionally can be 200 seconds or less, 100 seconds or less, 60 seconds or less, or 30 seconds or less at a temperature of about 100° C., about 90° C., about 80° C., about 70° C., about 60° C., about 50° C., about 40° C., about 20° C., or about 10° C. In embodiments wherein the dissolution temperature is not specified, the water-soluble nonwoven web has a dissolution time of 300 seconds or less at a temperature no greater than about 100° C. A fiber can have a complete dissolution time of 30 seconds or less at a temperature of about 100° C., about 90° C., about 80° C., about 70° C., about 60° C., about 50° C., about 40° C., about 20° C., or about 10° C. As used herein, a fiber is "insoluble," "water-insoluble," or "insoluble in water" when the fiber has a complete dissolution time of greater than 30 seconds at a specified temperature according to the method for determining single fiber solubility disclosed herein. In embodiments wherein the complete dissolution temperature is not specified, a water-soluble fiber has a complete dissolution time of 30 seconds or less at a temperature no greater than about 100° C. and a water-insoluble fiber has a complete dissolution time of greater than 30 seconds at a temperature no greater than about 100° C. As used herein and unless specified otherwise, the term "cold water-soluble" refers to any nonwoven web having a dissolution time of 300 seconds or less at 10° C. as determined according to MSTM-205. For example, the dissolution time optionally can be 200 seconds or less, 100 seconds or less, 60 seconds or less, or 30 seconds at 10° C. As used herein and unless specified otherwise, the term "cold water-soluble" in connection with a fiber refers to a fiber having a complete dissolution time of 30 seconds or less at a temperature of 10° C. or less, according to the Method for Determining Single Fiber Solubility disclosed herein.

As used herein and unless specified otherwise, the term "water-dispersible" refers to a nonwoven web, or article containing same wherein upon submersion in water at a specified temperature the nonwoven web or article physically disassociates into smaller constituent pieces. The smaller pieces may or may not be visible to the naked eye, may or may not remain suspended in the water, and may or may not ultimately dissolve. In embodiments wherein a dispersion temperature is not specified, the nonwoven web or pouch will disintegrate in 300 seconds or less at a temperature of about 100° C. or less, according to MSTM-205. For example, the disintegration time optionally can be 200 seconds or less, 100 seconds or less, 60 seconds or less, or 30 seconds or less at a temperature of about 80° C., about 70° C., about 60° C., about 50° C., about 40° C., about 20° C., or about 10° C., according to MSTM-205. For example, such dispersion parameters can be characteristic of a nonwoven web having a thickness of 6 mil (about 152 μm), or an article made therefrom.

As used herein, the term "flushable" refers to an article such as a nonwoven web, or pouch that is dispersible in aqueous environments, for example, a liquid sewage system, such that the disposal of the web(s) or pouch(es) does not result in the catching of such articles within the pipes of a plumbing system or building up over time to cause a blockage of such a pipe. The INDA/EDANA standard for flushability requires that greater than 95% of the starting material must pass through a 12.5 mm sieve after 60 minutes of slosh box testing using 28 RPM and 18° tilt angle. The Flushability Test set forth herein provides a more stringent flushability test. A commercially available nonwoven web in the form of a flushable wipe, herein referred to as Commercial Wipe A, is certified as flushable and has a disintegration time of 20 seconds as measured by the Flushability Test set forth herein. Thus, as used herein and unless specified otherwise, the term "flushable" refers to an article such as a nonwoven web or pouch that has a percent disintegration that meets or exceeds the percent degradation of Commercial Wipe A (20%) as measured by the Flushability Test as set forth herein. Flushable nonwoven webs and articles containing same have the advantage of being more processable in recycling processes or can simply be flushed in, for example, septic and municipal sewage treatment systems such that, after use, the web, structure, or pouch does not need to be landfilled, incinerated, or otherwise disposed of.

As used herein and unless specified otherwise, the term "nonwoven web" refers to a web or sheet comprising, consisting of, or consisting essentially of fibers arranged (e.g., by a carding process) and bonded to each other. Thus, the term nonwoven web can be considered short hand for nonwoven fiber-based webs. Further, as used herein, "nonwoven web" includes any structure including a nonwoven web or sheet, including, for example, a nonwoven web or sheet having a film laminated to a surface thereof. Methods of preparing nonwoven webs from fibers are well known in the art, for example, as described in *Nonwoven Fabrics Handbook*, prepared by Ian Butler, edited by Subhash Batra et al., Printing by Design, 1999, herein incorporated by reference in its entirety. As used herein and unless specified otherwise, the term "film" refers to a continuous film or sheet, e.g., prepared by a casting or extrusion process.

"Comprising" as used herein means that various components, ingredients or steps that can be conjointly employed in practicing the present disclosure. Accordingly, the term "comprising" encompasses the more restrictive terms "consisting essentially of" and "consisting of." The present compositions can comprise, consist essentially of, or consist of any of the required and optional elements disclosed herein. For example, a thermoformed packet can "consist essentially of" a nonwoven web described herein for use of its thermoforming characteristics, while including a non-thermoformed film or nonwoven web (e.g., lid portion), and optional markings on the film, e.g., by inkjet printing. The disclosure illustratively disclosed herein suitably may be practiced in the absence of any element or step which is not specifically disclosed herein.

All percentages, parts and ratios referred to herein are based upon the total dry weight of the nonwoven web or film composition or total weight of the packet content composition of the present disclosure, as the case may be, and all measurements made are at about 25° C., unless otherwise specified. All such weights as they pertain to listed ingredients are based on the active level and therefore do not include carriers or by-products that may be included in commercially available materials, unless otherwise specified.

All ranges set forth herein include all possible subsets of ranges and any combinations of such subset ranges. By default, ranges are inclusive of the stated endpoints, unless stated otherwise. Where a range of values is provided, it is understood that each intervening value between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also contemplated to be part of the disclosure.

It is expressly contemplated that for any number value described herein, e.g., as a parameter of the subject matter described or part of a range associated with the subject matter described, an alternative which forms part of the description is a functionally equivalent range surrounding the specific numerical value (e.g., for a dimension disclosed as "40 mm" an alternative embodiment contemplated is "about 40 mm").

As used herein, the terms packet(s) and pouch(es) should be considered interchangeable. In certain embodiments, the terms packet(s) and pouch(es), respectively, are used to refer to a container made using the nonwoven web and/or film, and to a fully-sealed container preferably having a material sealed therein, e.g., in the form a measured dose delivery system. The sealed pouches can be made from any suitable method, including such processes and features such as heat sealing, solvent welding, and adhesive sealing (e.g., with use of a water-soluble adhesive).

As used herein and unless specified otherwise, the terms "wt. %" and "wt %" are intended to refer to the composition of the identified element in "dry" (non-water) parts by weight of the entire article or composition referred to, for example a nonwoven web or film, including residual moisture in the nonwoven web or film (when applicable), or laminate structure, or parts by weight of a composition enclosed within a pouch (when applicable).

As used herein and unless specified otherwise, the term "PHR" ("phr") is intended to refer to the composition of the identified element in parts per one hundred parts water-soluble polymer (whether PVOH or other polymers, unless specified otherwise) in the polymer-containing article referred to, e.g., a water-soluble film, a fiber, or a nonwoven web, or a solution used to make the fiber or film.

The nonwoven webs, pouches, and related articles and methods of making and use are contemplated to include embodiments including any combination of one or more of the additional optional elements, features, and steps further described below (including those shown in the Examples and figures), unless stated otherwise.

Fiber Forming Materials

In general, the fibers of the disclosure can include a single fiber forming material or a combination (i.e., blend) of fiber forming materials. A single fiber can include one of more water-soluble fiber forming materials, one or more non-water-soluble fiber forming materials, or a combination of water-soluble and non-water-soluble fiber forming materials. The fibers of the disclosure can generally include a synthetic fiber forming material, a natural fiber forming material, a plant based fiber forming material, a bio-based fiber forming material, a biodegradable fiber forming material, a compostable fiber forming material, or a combination thereof. Plant-based fiber forming materials can be naturally occurring (e.g., cotton) or re-constituted (e.g., bamboo).

In general, the fibers of the disclosure include a fiber forming material that, prior to contact with a hydrolysis agent, includes a hydrolyzable group. Hydrolyzable groups generally include (a) any functional group that can be substituted with a nucleophile, such as water or a hydroxyl ion, in the presence of an acid or base catalyst, (b) cyclic functional groups that can be opened with a nucleophile (e.g., cyclic esters such as a lactone), (c) functional groups that can be cleaved with water in the presence of an enzyme to provide an —OH moiety on the polymer backbone, and/or (d) any functional group that can be reduced to provide an —OH moiety on the polymer backbone. Suitable hydrolyzable groups include, but are not limited to, esters, amides, ethers, acetals, nitriles, sulfhydryls, or a combination thereof. Suitable polymers including a hydrolyzable group include polyvinyl acetate, polyvinyl propionate, polyvinyl alcohol polymers having a degree of hydrolysis of less than 100%, poly(N-vinylacetamide) polymers, polyvinyl butyral polymers, poly(butyl acrylate) polymers, poly(butyl methacrylate) polymers, cellulose acetate polymers, polyacrylonitrile polymers, poly(N-isopropylacrylamide) polymers, poly(N,N-diethylacrylamide) polymers, poly(N,N-dimethylacrylamide) polymers, polyl(methylvinylether) polymers, poly(N,N-di methylaminoethyl methacrylate) polymers, poly(N-vinylformamide) polymers, poly(N-vinylcaprolactam) polymers, polyvinylpyrrolidone polymers, polylactic acid, and combinations thereof.

In embodiments, the fibers of the disclosure include a polymer comprising at least one of a vinyl acetate moiety or a vinyl alcohol moiety. Such a polymer is hydrolyzable. Unless expressly indicated otherwise, the term "a polymer comprising at least one of a vinyl acetate moiety or a vinyl alcohol moiety" as used herein will be understood to encompass any polymer having at least one moiety resulting from only vinyl acetate, only vinyl alcohol, or both vinyl acetate and vinyl alcohol. In some embodiments, suitable examples of such a polymer (or the polymer) include, without limitation, a polyvinyl alcohol homopolymer, a polyvinyl acetate homopolymer, a polyvinyl alcohol copolymer, a modified polyvinyl alcohol copolymer, and combinations thereof. For example, the polyvinyl alcohol copolymer is a copolymer of vinyl acetate and vinyl alcohol in some embodiments. For example, in some embodiments, the modified polyvinyl alcohol copolymer comprises an anionically modified copolymer, which may be a copolymer of vinyl acetate and vinyl alcohol further comprising additional groups such as a carboxylate, a sulfonate, or combinations thereof. Such a polymer comprising at least one of a vinyl acetate moiety or a vinyl alcohol moiety may also include an additional polymer, for example, in a blend.

Unless expressly indicated otherwise, the term "degree of hydrolysis" is understood as a percentage (e.g., a molar percentage) of hydrolyzed moieties among all hydrolyzable moieties a polymer initially has. For example, for a polymer comprising at least one of a vinyl acetate moiety or a vinyl alcohol moiety, partial replacement of an ester group in vinyl acetate moieties with a hydroxyl group occurs during hydrolysis, and a vinyl acetate moiety becomes a vinyl alcohol moiety. The degree of hydrolysis of a polyvinyl acetate homopolymer is considered as zero, while the degree of hydrolysis of a polyvinyl alcohol homopolymer is 100%. The degree of hydrolysis of a copolymer of vinyl acetate and vinyl alcohol is equal to a percentage of vinyl alcohol moieties among a total of vinyl acetate and vinyl alcohol moieties, and is between zero and 100%.

Polyvinyl alcohol is a synthetic polymer that can be prepared by the alcoholysis, also termed hydrolysis or saponification, of polyvinyl acetate. Fully hydrolyzed PVOH, where virtually all the acetate groups have been converted to alcohol groups, is a strongly hydrogen-bonded, highly crystalline polymer which dissolves only in hot water—greater than about 140° F. (about 60° C.). If a sufficient number of acetate groups are allowed to remain after the hydrolysis of polyvinyl acetate, that is the polymer is partially hydrolyzed, then the polymer is more weakly hydrogen-bonded, less crystalline, and is generally soluble in cold water—less than about 50° F. (about 10° C.). As such, the partially hydrolyzed polymer is a vinyl alcohol-vinyl acetate copolymer that is a PVOH copolymer, but is commonly referred to as "polyvinyl alcohol (PVOH)" or "the PVOH polymer." For brevity, the term "the PVOH polymer" used herein is understood to encompass a homopolymer, a copolymer, and a modified copolymer comprising vinyl alcohol moieties, for example, 50% or higher of vinyl alcohol moieties.

The fibers described herein can include polyvinyl acetate, one or more polyvinyl alcohol (PVOH) homopolymers, one or more polyvinyl alcohol copolymers, or a combination thereof. As used herein, the term "homopolymer" generally includes polymers having a single type of monomeric repeating unit (e.g., a polymeric chain consisting of or consisting essentially of a single monomeric repeating unit). For the particular case of "PVOH," the term "the PVOH polymer" as an example of a hydrolyzable polymer or a polymer comprising at least one of a vinyl acetate moiety or a vinyl alcohol moiety includes copolymers consisting of a distribution of vinyl alcohol monomer units and vinyl acetate monomer units, depending on the degree of hydrolysis (e.g., a polymeric chain consisting of or consisting essentially of vinyl alcohol and vinyl acetate monomer units). In the limiting case of 100% hydrolysis, a PVOH homopolymer can include a true homopolymer having only vinyl alcohol units. In some embodiments, the fibers and/or films of the disclosure include such a polymer comprising at least one of a vinyl acetate moiety or a vinyl alcohol moiety. In some embodiments, the fibers and/or films of the disclosure include a hot water-soluble polymer comprising at least one of a vinyl acetate moiety or a vinyl alcohol moiety.

In some embodiments, the hydrolyzable polymer described herein includes a modified polyvinyl alcohol, for example, a copolymer. The modified polyvinyl alcohol can include a copolymer or higher polymer (e.g., ter-polymer) including one or more monomers in addition to the vinyl acetate/vinyl alcohol groups. Optionally, the modification is neutral, e.g., provided by an ethylene, propylene, N-vinylpyrrolidone or other non-charged monomer species. Optionally, the modification is a cationic modification, e.g., provided by a positively charged monomer species. Optionally, the modification is an anionic modification. Thus, in some embodiments, the polyvinyl alcohol includes an anionic modified polyvinyl alcohol. An anionic modified polyvinyl alcohol can include a partially or fully hydrolyzed PVOH copolymer that includes an anionic monomer unit, a vinyl alcohol monomer unit, and optionally a vinyl acetate monomer unit (i.e., when not completely hydrolyzed). In some embodiments, the PVOH copolymer can include two or more types of anionic monomer units. General classes of anionic monomer units which can be used for the PVOH copolymer include the vinyl polymerization units corresponding to sulfonic acid vinyl monomers and their esters, monocarboxylic acid vinyl monomers, their esters and anhydrides, dicarboxylic monomers having a polymerizable double bond, their esters and anhydrides, and alkali metal salts of any of the foregoing. Examples of suitable anionic monomer units include the vinyl polymerization units corresponding to vinyl anionic monomers including vinyl acetic acid, maleic acid, monoalkyl maleate, dialkyl maleate, maleic anhydride, fumaric acid, monoalkyl fumarate, dialkyl fumarate, itaconic acid, monoalkyl itaconate, dialkyl itaconate, citraconic acid, monoalkyl citraconate, dialkyl citraconate, citraconic anhydride, mesaconic acid, monoalkyl mesaconate, dialkyl mesaconate, glutaconic acid, monoalkyl glutaconate, dialkyl glutaconate, glutaconic anhydride, alkyl acrylates, alkyl alkacrylates, vinyl sulfonic acid, allyl sulfonic acid, ethylene sulfonic acid, 2-acrylamido-1-methyl propane sulfonic acid, 2-acrylamide-2-methyl propanesulfonic acid, 2-methylacrylamido-2-methyl propanesulfonic acid, 2-sulfoethyl acrylate, alkali metal salts of the foregoing (e.g., sodium, potassium, or other alkali metal salts), esters of the foregoing (e.g., methyl, ethyl, or other $C_1$-$C_4$ or $C_6$ alkyl esters), and combinations of the foregoing (e.g., multiple types of anionic monomers or equivalent forms of the same anionic monomer). In some embodiments, the PVOH copolymer can include two or more types of monomer units selected from neutral, anionic, and cationic monomer units.

The level of incorporation of the one or more monomer units/level of modification in the PVOH copolymers is not particularly limited. In embodiments, the one or more monomer units/modifications are present in the PVOH copolymer in an amount in a range of about 1 mol. % or 2 mol. % to about 6 mol. % or 10 mol. % (e.g., at least 1.0, 1.5, 2.0, 2.5, 3.0, 3.5, or 4.0 mol. % and/or up to about 3.0, 4.0, 4.5, 5.0, 6.0, 8.0, or 10 mol. % in various embodiments). In embodiments, the modification is an anionic modification and the anionic monomer units are present in the PVOH copolymer in an amount in a range of about 1 mol. % or 2 mol. % to about 6 mol. % or 10 mol. % (e.g., at least 1.0, 1.5, 2.0, 2.5, 3.0, 3.5, or 4.0 mol. % and/or up to about 3.0, 4.0, 4.5, 5.0, 6.0, 8.0, or 10 mol. % in various embodiments).

Polyvinyl alcohols can be subject to changes in solubility characteristics. The acetate group in the co-poly(vinyl acetate vinyl alcohol) polymer (PVOH copolymer) is known by those skilled in the art to be hydrolysable by either acid or alkaline hydrolysis. As the degree of hydrolysis increases, a polymer composition made from the PVOH copolymer will have increased mechanical strength but reduced solubility at lower temperatures (e.g., requiring hot water temperatures for dissolution). Accordingly, exposure of a PVOH copolymer to an alkaline environment (e.g., resulting from a laundry bleaching additive) can transform the polymer from one which dissolves rapidly and entirely in a given aqueous environment (e.g., a cold water medium) to one which dissolves slowly and/or incompletely in the aqueous environment, potentially resulting in undissolved polymeric residue at the end of a wash cycle.

PVOH copolymers with pendant carboxyl groups, such as, for example, vinyl alcohol/hydrolyzed methyl acrylate sodium salt polymers, can form lactone rings between neighboring pendant carboxyl and alcohol groups, thus reducing the water solubility of the PVOH copolymer. In the presence of a strong base, the lactone rings can open over the course of several weeks at relatively warm (ambient) and high humidity conditions (e.g., via lactone ring-opening reactions to form the corresponding pendant carboxyl and alcohol groups with increased water solubility). Thus, contrary to the effect observed with a PVOH copolymer without pendant carboxyl groups, it is believed that such a PVOH copolymer can become more soluble due to chemical interactions between the polymer and an alkaline composition inside a pouch during storage.

Specific sulfonic acids and derivatives thereof having polymerizable vinyl bonds can be copolymerized with vinyl acetate to provide cold-water-soluble PVOH polymers which are stable in the presence of strong bases. The base-catalyzed alcoholysis products of these copolymers, which are used in the formulation of water-soluble film, are vinyl alcohol-sulfonate salt copolymers which are rapidly soluble. The sulfonate group in the PVOH copolymer can revert to a sulfonic acid group in the presence of hydrogen ions, but the sulfonic acid group still provides excellent cold-water solubility of the polymer. In embodiments, vinyl alcohol-sulfonate salt copolymers contain no residual acetate groups (i.e., are fully hydrolyzed) and therefore are not further hydrolysable by either acid or alkaline hydrolysis. Generally, as the amount of modification increases, the water solubility increases, thus sufficient modification via sulfonate or sulfonic acid groups inhibit hydrogen bonding and crystallinity, enabling solubility in cold water. In the presence of acidic or basic species, the copolymer is generally unaffected, with the exception of the sulfonate or sulfonic acid groups, which maintain excellent cold water solubility even in the presence of acidic or basic species. Examples of suitable sulfonic acid comonomers (and/or their alkali metal salt derivatives) include vinyl sulfonic acid, allyl sulfonic acid, ethylene sulfonic acid, 2-acrylamido-1-methylpropanesulfonic acid, 2-acrylamido-2-methylpropanesufonic acid, 2-methacrylamido-2-methyl propanesulfonic acid and 2-sulfoethyl acrylate, with the sodium salt of 2-acrylamido-2-methylpropanesulfonic acid (AMPS) being a preferred comonomer.

The fiber forming polymers, whether polyvinyl alcohol polymers or otherwise, can be blended. When the polymer blend includes a blend of polyvinyl alcohol polymers, the PVOH polymer blend can include a first PVOH polymer ("first PVOH polymer"), which can include a PVOH copolymer or a modified PVOH copolymer including one or more types of anionic monomer units (e.g., a PVOH ter- (or higher co-) polymer), and a second PVOH polymer ("second PVOH polymer"), which can include a PVOH comopolymer or a modified PVOH copolymer including one or more types of anionic monomer units (e.g., a PVOH ter- (or higher co-) polymer). In some aspects, the PVOH polymer blend includes only the first PVOH polymer and the second PVOH polymer (e.g., a binary blend of the two polymers). Alternatively, or additionally, the PVOH polymer blend or a fiber or nonwoven web made therefrom can be characterized as being free or substantially free from other polymers (e.g., other polymers generally, other PVOH-based polymers specifically, or both). As used herein, "substantially free" means that the first and second PVOH polymers make up at least 95 wt. %, at least 97 wt. %, or at least 99 wt. % of the total amount of water-soluble polymers in the water-soluble fiber or film. In other aspects, the fiber can include one or more additional water-soluble polymers. For example, the PVOH polymer blend can include a third PVOH polymer, a fourth PVOH polymer, a fifth PVOH polymer, etc. (e.g., one or more additional PVOH copolymers or modified PVOH copolymers, with or without anionic monomer units). For example, the fiber can include at least a third (or fourth, fifth, etc.) water-soluble polymer which is other than a PVOH polymer (e.g., other than PVOH copolymers or modified PVOH copolymers, with or without anionic monomer units).

The degree of hydrolysis (DH) of the PVOH copolymers included in the fibers of the present disclosure can be in a range of about 75% to about 99.9% (e.g., about 79% to about 99.9%, about 79% to about 92%, about 80% to about 90%, about 88% to 92%, about 86.5% to about 89%, or about 88%, 90% or 92% such as for cold-water-soluble compositions; about 90% to about 99%, about 92% to about 99%, about 95% to about 99%, about 98% to about 99%, about 98% to about 99.9%, about 96%, about 98%, about 99%, or greater than 99%). As the degree of hydrolysis is reduced, a fiber made from the polymer will have reduced mechanical strength but faster solubility at temperatures below about 20° C. As the degree of hydrolysis increases, a fiber or film made from the polymer will tend to be mechanically stronger and the thermoformability will tend to decrease. The degree of hydrolysis can be chosen such that the water-solubility of the polymer is temperature dependent, and thus the solubility of a fiber made from the polymer is also influenced. In one option the fiber is cold water-soluble. For a co-poly(vinyl acetate vinyl alcohol) polymer that does not include any other monomers (e.g., a homopolymer not copolymerized with an anionic monomer) a cold water-soluble fiber, soluble in water at a temperature of less than 10° C., can include PVOH with a degree of hydrolysis in a range of about 75% to about 90%, or in a range of about 80% to about 90%, or in a range of about 85% to about 90%. In another option the fiber is hot water-soluble. For a co-poly (vinyl acetate vinyl alcohol) polymer that does not include any other monomers (e.g., a homopolymer not copolymerized with an anionic monomer) a hot water-soluble fiber, soluble in water at a temperature of at least about 60° C., can include PVOH with a degree of hydrolysis of at least about 98%.

The degree of hydrolysis of the polymer blend can also be characterized by the arithmetic weighted, average degree of hydrolysis ($\overline{H}°$). For example, $\overline{H}°$ for a PVOH polymer that includes two or more PVOH polymers is calculated by the formula $\overline{H}°=\Sigma(W_i \cdot H_i)$ where $W_i$ is the molar percentage of the respective PVOH polymer and $H_i$ is the respective degrees of hydrolysis. When a polymer is referred to as having a specific degree of hydrolysis, the polymer can be a single polyvinyl alcohol polymer having the specified degree of hydrolysis or a blend of polyvinyl alcohol polymers having an average degree of hydrolysis as specified.

The viscosity of a PVOH polymer ($\mu$) is determined by measuring a freshly made solution using a Brookfield LV type viscometer with UL adapter as described in British Standard EN ISO 15023-2:2006 Annex E Brookfield Test method. It is international practice to state the viscosity of 4% aqueous polyvinyl alcohol solutions at 20° C. All viscosities specified herein in Centipoise (cP) should be understood to refer to the viscosity of 4% aqueous polyvinyl alcohol solution at 20° C., unless specified otherwise. Similarly, when a polymer is described as having (or not having) a particular viscosity, unless specified otherwise, it is intended that the specified viscosity is the average viscosity for the polymer, which inherently has a corresponding molecular weight distribution, i.e. the weighted natural log average viscosity as described below. It is well known in the art that the viscosity of PVOH polymers is correlated with the weight average molecular weight ($\overline{M}w$) of the PVOH polymer, and often the viscosity is used as a proxy for the $\overline{M}w$.

In embodiments, the PVOH polymer can have a viscosity of about 1.0 to about 50.0 cP, about 1.0 to about 40.0 cP, or about 1.0 to about 30.0 cP, for example about 4 cP, 8 cP, 15 cP, 18 cP, 23 cP, or 26 cP. In embodiments, the PVOH homopolymers and/or copolymers can have a viscosity of about 1.0 to about 40.0 cP, or about 5 cP to about 23 cP, for example, about 1 cP, 1.5 cP, 2 cP, 2.5 cP, 3 cP, 3.5 cP, 4 cP, 4.5 cP, 5 cP, 5.5 cP, 6 cP, 6.5 cP, 7 cP, 7.5 cP, 8 cP, 8.5 cP, 9 cP, 9.5 cP, 10 cP, 11 cP, 12 cP, 13 cP, 14 cP, 15 cP, 17.5 cP, 18 cP, 19 cP, 20 cP, 21 cP, 22 cP, 23 cP, 24 cP, 25 cP, 26 cP, 27 cP, 28 cP, 29 cP, 30 cP, 31 cP, 32 cP, 33 cP, 34 cP, 35 cP, or 40 cP. In embodiments, the PVOH homopolymers and/or copolymers can have a viscosity of about 21 cP to 26 cP. In embodiments, the PVOH homopolymers and/or copolymers can have a viscosity of about 5 cP to about 14 cP. In embodiments, the PVOH homopolymers and/or copolymers can have a viscosity of about 5 cP to about 23 cP.

For reference, in a polymer blend, the first PVOH polymer is denoted as having a first 4% solution viscosity at 20° C. ($\mu_1$), and the second PVOH polymer is denoted as having a second 4% solution viscosity at 20° C. ($\mu_2$). In various embodiments, the first viscosity pi can be in a range of about 4 cP to about 70 cP (e.g., at least about 4, 8, 10, 12, or 16 cP and/or up to about 12, 16, 20, 24, 28, 30, 32, 35, 37, 40, 45, 48, 50, 56, 60, or 70 cP, such as about 4 cP to about 70 cP, about 4 cP to about 60 cP, about 4 cP to about 46 cP, about 4 cP to about 24 cP, about 10 cP to about 16 cP, or about 10 cP to about 20 cP, or about 20 cP to about 30 cP). Alternatively or additionally, the second viscosity $\mu_2$ can be in a range of about 4 cP to about 70 cP (e.g., at least about 4, 8, 10, 12, or 16 cP and/or up to about 12, 16, 20, 24, 28, 30, 32, 35, 37, 40, 45, 48, 50, 56, 60, or 70 cP, such as about 12 cP to about 30 cP, about 10 cP to about 16 cP, or about 10 cP to about 20 cP, or about 20 cP to about 30 cP). When the PVOH polymer blend includes three or more PVOH polymers selected from PVOH polymer and PVOH copolymers, the foregoing viscosity values can apply to each PVOH polymer or PVOH copolymer individually. Thus, the weight-average molecular weight of the water-soluble polymers, including the first PVOH copolymer and the second PVOH copolymer, can be in a range of about 30,000 to about 175,000, or about 30,000 to about 100,000, or about 55,000 to about 80,000, for example. When referring to average viscosity of the PVOH polymer blend, the weighted natural log average viscosity ($\bar{\mu}$) is used. The $\bar{\mu}$ for a PVOH polymer that includes in two or more PVOH polymers is calculated by the formula $\bar{\mu}=e^{\Sigma W_i \ln \mu_i}$ where $\mu_i$ is the viscosity for the respective PVOH polymers.

In embodiments wherein the water-soluble fiber includes a blend of a polyvinyl alcohol homopolymer and a polyvinyl alcohol copolymer, the relative amounts of homopolymer and copolymer are not particularly limited. The polyvinyl alcohol homopolymer can make up about 15 wt. % to about 70 wt. % of total weight of the water-soluble polymer blend, for example, at least about 15 wt. %, at least about 20 wt. %, at least about 25 wt. %, at least about 30 wt. %, at least about 40 wt. %, at least about 50 wt. %, or at least about 60 wt. % and up to about 70 wt. %, up to about 60 wt. %, up to about 50 wt. %, up to about 40 wt. %, or up to about 30 wt. %, based on the total weight of the water-soluble polymer blend, and can be a single homopolymer or a blend of one or more homopolymers (e.g., having a difference in viscosity and/or degree of hydrolysis). The remainder of the water-soluble polymer blend can be the water-soluble polyvinyl alcohol copolymer. Without intending to be bound by theory, it is believed that as the amount of homopolymer decreases below about 15 wt. %, the ability of the blend of polyvinyl alcohol homopolymer and copolymer to form a fiber decreases. The water-soluble polyvinyl alcohol copolymer can make up about 30 wt. % to about 85 wt. % of the total weight of the water-soluble polymer blend, for example, at least about 30 wt. %, at least about 40 wt. %, at least about 50 wt. %, at least about 60 wt. %, at least about 70 wt. %, at least about 75 wt. %, or at least about 80 wt. %, and up to about 85 wt. %, up to about 80 wt. %, up to about 70 wt. %, up to about 60 wt. %, up to about 50 wt. %, or up to about 40 wt. %, based on the total weight of the water-soluble polymer blend, and can be a single copolymer or a blend of one or more copolymers. The blend can consist of a polyvinyl alcohol homopolymer and a polyvinyl alcohol copolymer. The blend can consist of a polyvinyl alcohol homopolymer and a plurality of polyvinyl alcohol copolymers. The blend can consist of more than one polyvinyl alcohol homopolymer and more than one polyvinyl alcohol copolymer.

In embodiments, the fibers comprise polyvinyl acetate, a polyvinyl alcohol homopolymer, a polyvinyl alcohol copolymer, a modified polyvinyl alcohol copolymer, or a combination thereof. In embodiments, the fibers comprise a polyvinyl alcohol homopolymer, a polyvinyl alcohol copolymer, a modified polyvinyl alcohol copolymer, or a combination thereof. In embodiments, the fibers comprise a polyvinyl alcohol copolymer. In embodiments, the fibers comprise a modified polyvinyl alcohol copolymer. In embodiments, the fibers comprise a polyvinyl alcohol copolymer that is an anionically modified copolymer. In embodiment, the fibers comprise an anionically modified copolymer and the anionic modification comprises a carboxylate, a sulfonate, or a combination thereof. In embodiments, the polyvinyl alcohol polymer is water-soluble prior to admixing the fiber with the hydrolysis agent solution. In embodiments, the polymer has a degree of hydrolysis greater than about 79% and less than about 99.9% (e.g., from about 79% to about 96%), prior to admixing the fiber with the hydrolysis agent solution.

The fibers of the disclosure can include water-soluble polymers other than polyvinyl acetate and PVOH including, but are not limited to, polyacrylate, water-soluble acrylate copolymer, polyvinyl pyrrolidone, polyethylenimine, pullulan, water-soluble natural polymer including, but not limited to, guar gum, gum Acacia, xanthan gum, carrageenan, and water-soluble starch, water-soluble polymer derivatives including, but not limited to, modified starches, ethoxylated starch, and hydroxypropylated starch, copolymers of the foregoing and a combination of any of the foregoing additional polymers or copolymers. Yet other water-soluble polymers can include polyalkylene oxides, polyacrylamides, polyacrylic acids and salts thereof, water-soluble celluloses, cellulose ethers, cellulose esters, cellulose amides, additional polyvinyl acetate, polycarboxylic acids and salts thereof, polyamino acids, polyamides, gelatins, methylcelluloses, carboxymethylcelluloses and salts thereof, dextrins, ethylcelluloses, hydroxyethyl celluloses, hydroxypropyl methylcelluloses, maltodextrins, polymethacrylates, and combinations of any of the foregoing. Such water-soluble polymers, whether PVOH or otherwise are commercially available from a variety of sources.

In embodiments, the fiber includes the polyvinyl alcohol polymer and an additional polymer comprising a polyvinyl alcohol, a polyvinyl acetate, a polyacrylate, a water-soluble acrylate copolymer, a polyvinyl pyrrolidone, a polyethylenimine, a pullulan, a guar gum, a gum Acacia, a xanthan gum, a carrageenan, a starch, a modified starch, a polyalkylene oxide, a polyacrylamide, a polyacrylic acid, a cellulose, a cellulose ether, a cellulose ester, a cellulose amide, a polycarboxylic acid, a polyamino acid, a polyamide, a gelatin, a dextrin, copolymers of the foregoing, and a combination of any of the foregoing additional polymers or copolymers.

The fibers can additionally include a water-insoluble fiber forming material. Suitable water-insoluble fiber forming materials include, but are not limited to, cotton, polyester, copolyester, polyethylene (e.g., high density polyethylene and low density polyethylene), polypropylene, wood pulp, fluff pulp, abaca, viscose, insoluble cellulose, insoluble starch, hemp, jute, flax, ramie, sisal, bagasse, banana fiber, lacebark, silk, sinew, catgut, wool, sea silk, mohair, angora, cashmere, collagen, actin, nylon, Dacron, rayon, bamboo fiber, modal, diacetate fiber, triacetate fiber, polyester, copolyester, polylactide (PLA), polyethylene terephthalate (PET), polypropylene (PP), and combinations thereof. In embodiments, the water-insoluble fiber does not include cotton or rayon. In embodiments, the water-insoluble fiber comprises wool, diacetate, triacetate, nylon, PLA, PET, PP, or a combination thereof.

The fibers can further comprise non-fiber forming materials, referred to herein as auxiliary or secondary ingredients. Auxiliary agents can include active agents and processing agents such as, but not limited to active agents, plasticizers, plasticizer compatibilizers, surfactants, lubricants, release agents, fillers, extenders, cross-linking agents, antiblocking agents, antioxidants, detackifying agents, antifoams, nanoparticles such as layered silicate-type nanoclays (e.g., sodium montmorillonite), bleaching agents (e.g., sodium metabisulfite, sodium bisulfite or others), aversive agents such as bitterants (e.g., denatonium salts such as denatonium benzoate, denatonium saccharide, and denatonium chloride; sucrose octaacetate; quinine; flavonoids such as quercetin and naringen; and quassinoids such as quassin and brucine) and pungents (e.g., capsaicin, piperine, allyl isothiocyanate, and resinferatoxin), and other functional ingredients, in amounts suitable for their intended purposes. As used herein and unless specified otherwise, "auxiliary agents" include secondary additives, processing agents, and active agents. Specific such auxiliary agents and processing agents can be selected from those suitable for use in water-soluble fibers, water-insoluble fibers, nonwoven webs, or those suitable for use in water-soluble films.

In embodiments, the fibers of the disclosure are free of auxiliary agents. As used herein and unless specified otherwise, "free of auxiliary agents" with respect to the fiber means that the fiber includes less than about 0.01 wt. %, less than about 0.005 wt. %, or less than about 0.001 wt. % of auxiliary agents, based on the total weight of the fiber.

A plasticizer is a liquid, solid, or semi-solid that is added to a material (usually a resin or elastomer) making that material softer, more flexible (by decreasing the glass-transition temperature of the polymer), and easier to process. A polymer can alternatively be internally plasticized by chemically modifying the polymer or monomer. In addition, or in the alternative, a polymer can be externally plasticized by the addition of a suitable plasticizing agent. Water is recognized as a very efficient plasticizer for PVOH and other polymers; including but not limited to water-soluble polymers, however, the volatility of water makes its utility limited since polymer films need to have at least some resistance (robustness) to a variety of ambient conditions including low and high relative humidity.

The plasticizer can include, but is not limited to, glycerin, diglycerin, sorbitol, ethylene glycol, diethylene glycol, triethylene glycol, dipropylene glycol, tetraethylene glycol, propylene glycol, polyethylene glycols up to 400 MW, neopentyl glycol, trimethylolpropane, polyether polyols, sorbitol, 2-methyl-1,3-propanediol (MPDiol®), ethanolamines, and a mixture thereof. The total amount of the non-water plasticizer provided in a fiber can be in a range of about 1 wt. % to about 45 wt. %, or about 5 wt. % to about 45 wt. %, or about 10 wt. % to about 40 wt. %, or about 20 wt. % to about 30 wt. %, about 1 wt. % to about 4 wt. %, or about 1.5 wt. % to about 3.5 wt. %, or about 2.0 wt. % to about 3.0 wt. %, for example about 1 wt. %, about 2.5 wt. %, about 5 wt. %, about 10 wt. %, about 15 wt. %, about 20 wt. %, about 25 wt. %, about 30 wt. %, about 35 wt. %, or about 40 wt. %, based on total fiber weight.

Surfactants for use in fibers are well known in the art. Surfactants for use in films are also well known in the art and can suitably be used in the fibers and/or nonwoven webs of the disclosure. Optionally, surfactants are included to aid in the dispersion of the fibers during carding. Suitable surfactants for fibers of the present disclosure include, but are not limited to, dialkyl sulfosuccinates, lactylated fatty acid esters of glycerol and propylene glycol, lactylic esters of fatty acids, sodium alkyl sulfates, polysorbate 20, polysorbate 60, polysorbate 65, polysorbate 80, alkyl polyethylene glycol ethers, lecithin, acetylated fatty acid esters of glycerol and propylene glycol, sodium lauryl sulfate, acetylated esters of fatty acids, myristyl dimethylamine oxide, trimethyl tallow alkyl ammonium chloride, quaternary ammonium compounds, alkali metal salts of higher fatty acids containing about 8 to 24 carbon atoms, alkyl sulfates, alkyl polyethoxylate sulfates, alkylbenzene sulfonates, monoethanolamine, lauryl alcohol ethoxylate, propylene glycol, diethylene glycol, salts thereof and combinations of any of the forgoing.

Suitable surfactants can include the nonionic, cationic, anionic and zwitterionic classes. Suitable surfactants include, but are not limited to, propylene glycols, diethylene glycols, monoethanolamine, polyoxyethylenated polyoxypropylene glycols, alcohol ethoxylates, alkylphenol ethoxylates, tertiary acetylenic glycols and alkanolamides (nonionics), polyoxyethylenated amines, quaternary ammonium salts and quaternized polyoxyethylenated amines (cationics), alkali metal salts of higher fatty acids containing about 8 to 24 carbon atoms, alkyl sulfates, alkyl polyethoxylate sulfates and alkylbenzene sulfonates (anionics), and amine oxides, N-alkylbetaines and sulfobetaines (zwitterionics). Other suitable surfactants include dioctyl sodium sulfosuccinate, lactylated fatty acid esters of glycerin and propylene glycol, lactylic esters of fatty acids, sodium alkyl sulfates, polysorbate 20, polysorbate 60, polysorbate 65, polysorbate 80, lecithin, acetylated fatty acid esters of glycerin and propylene glycol, and acetylated esters of fatty acids, and combinations thereof. In various embodiments, the amount of surfactant in the fiber is in a range of about 0.01 wt. %, to about 2.5 wt. %, about 0.1 wt. % to about 2.5 wt. %, about 1.0 wt. % to about 2.0 wt. %, about 0.01 wt % to 0.25 wt %, or about 0.10 wt % to 0.20 wt %.

In embodiments, the fibers and/or nonwoven webs of the disclosure can include an active agent. The active agent can be added to the fiber itself, or during carding of the nonwoven web, and/or can be added to the nonwoven web prior to bonding. Active agents added to the fibers during carding can be distributed throughout the nonwoven web. Active agents added to the nonwoven web after carding but prior to bonding can be selectively added to one or both faces of the nonwoven web. Additionally, active agents can be added to the surface of pouches or other articles prepared from the nonwoven webs. In embodiments, the active agent is provided as part of the plurality of fibers, dispersed within the nonwoven web, provided on a face of the nonwoven web, or a combination thereof.

The active agent, when present in the fiber and/or nonwoven web in an amount of at least about 1 wt %, or in a range of about 1 wt % to about 99 wt %, provides additional functionality to the nonwoven web. In embodiments, the active agent can comprise one or more components including, but not limited to, enzymes, oils, flavors, colorants, odor absorbers, fragrances, pesticides, fertilizers, activators, acid catalysts, metal catalysts, ion scavengers, detergents, disinfectants, surfactants, bleaches, bleach components, fabric softeners or combinations thereof. In embodiments, the active agent can comprise a colorant, a surfactant, or a combination thereof. The active agent can take any desired form, including as a solid (e.g., powder, granulate, crystal, flake, or ribbon), a liquid, a mull, a paste, a gas, etc., and optionally can be encapsulated.

In certain embodiments, the active agent may comprise an enzyme. Suitable enzymes include enzymes categorized in any one of the six conventional Enzyme Commission (EC) categories, i.e., the oxidoreductases of EC 1 (which catalyze oxidation/reduction reactions), the transferases of EC 2 (which transfer a functional group, e.g., a methyl or phosphate group), the hydrolases of EC 3 (which catalyze the hydrolysis of various bonds), the lyases of EC 4 (which cleave various bonds by means other than hydrolysis and oxidation), the isomerases of EC 5 (which catalyze isomerization changes within a molecule) and the ligases of EC 6 (which join two molecules with covalent bonds). Examples of such enzymes include dehydrogenases and oxidases in EC 1, transaminases and kinases in EC 2, lipases, cellulases, amylases, mannanases, and peptidases (a.k.a. proteases or proteolytic enzymes) in EC 3, decarboxylases in EC 4, isomerases and mutases in EC 5 and synthetases and synthases of EC 6. Suitable enzymes from each category are described in, for example, U.S. Pat. No. 9,394,092, the entire disclosure of which is herein incorporated by reference.

Enzymes for use in laundry and dishwashing applications can include one or more of protease, amylase, lipase, dehydrogenase, transaminase, kinase, cellulase, mannanase, peptidase, decarboxylase, isomerase, mutase, synthetase, synthase, and oxido-reductase enzymes, including oxidoreductase enzymes that catalyze the formation of bleaching agents.

Oils other than fragrances can include flavorants and colorants.

In one class of embodiments the active agent includes a flavor or combination of flavors. Suitable flavors include but are not limited to, spearmint oil, cinnamon oil, oil of wintergreen (methylsalicylate), peppermint oils, and synthetic and natural fruit flavors, including citrus oils.

In some embodiments, the active agent may be a colorant or combination of colorants. Examples of suitable colorants include food colorings, caramel, paprika, cinnamon, and saffron. Other examples of suitable colorants can be found in U.S. Pat. No. 5,002,789, hereby incorporated by reference in its entirety.

Another class of embodiments include one or more odor absorbers as active agents. Suitable odor absorbers for use as active agents according to the disclosure include, but are not limited to, zeolites, and complex zinc salts of ricinoleic acid. The odor absorbing active agent can also comprise fixatives that are well known in the art as largely odor-neutral fragrances, including but not limited to extracts of labdanum, styrax, and derivatives of abietic acid.

Another class of embodiments include one or more fragrances as active agents. As used herein, the term fragrance refers to any applicable material that is sufficiently volatile to produce a scent. Embodiments including fragrances as active agents can include fragrances that are scents pleasurable to humans, or alternatively fragrances that are scents repellant to humans, animals, and/or insects. Suitable fragrances include, but are not limited to, fruits including, but not limited to, lemon, apple, cherry, grape, pear, pineapple, orange, strawberry, raspberry, musk and flower scents including, but not limited to, lavender-like, rose-like, iris-like and carnation-like. Optionally the fragrance is one which is not also a flavoring. Other fragrances include herbal scents including, but not limited to, rosemary, thyme, and sage; and woodland scents derived from pine, spruce and other forest smells. Fragrances may also be derived from various oils, including, but not limited to, essential oils, or from plant materials including, but not limited to, peppermint, spearmint and the like. Suitable fragrant oils can be found in U.S. Pat. No. 6,458,754, hereby incorporated by reference in its entirety.

Fragrances can include perfumes. The perfume may comprise neat perfume, encapsulated perfume, or mixtures thereof. Preferably, the perfume includes neat perfume. A portion of the perfume may be encapsulated in a core-shell encapsulate. In another type of embodiment, the perfume will not be encapsulated in a core-shell encapsulate.

As used herein, the term "perfume" encompasses the perfume raw materials (PRMs) and perfume accords. The term "perfume raw material" as used herein refers to compounds having a molecular weight of at least about 100 g/mol and which are useful in imparting an odor, fragrance, essence or scent, either alone or with other perfume raw materials. As used herein, the terms "perfume ingredient" and "perfume raw material" are interchangeable. The term "accord" as used herein refers to a mixture of two or more PRMs.

Applicable insect repellant fragrances include one or more of dichlorvos, pyrethrin, allethrin, naled and/or fenthion pesticides disclosed in U.S. Pat. No. 4,664,064, incorporated herein by reference in its entirety. Suitable insect repellants are citronellal (3,7-dimethyl octanal), N,N-diethyl-3-methylbenzamide (DEET), vanillin, and the volatile oils extracted from turmeric (*Curcuma longa*), kaffir lime (*Citrus hystrix*), citronella grass (*Cymbopogon winterianus*) and hairy basil (*Ocimum americanum*). Moreover, applicable insect repellants can be mixtures of insect repellants.

In one class of embodiments, the active agents according to the disclosure can comprise one or more pesticides. Suitable pesticides may include, but are not limited to, insecticides, herbicides, acaricides, fungicides, and larvacides.

Another class of embodiments include one or more fertilizers as active agents. As used herein, the term fertilizer applies to any applicable material that releases one or more of nitrogen, phosphorus, potassium, calcium, magnesium, sulfur, boron, chlorine, copper, iron, manganese, molybdenum, or zinc. Suitable fertilizers include, but are not limited to zeolites. For example, clinoptilolite is a zeolite that releases potassium and can also release nitrogen when preloaded with ammonium.

One class of embodiments comprise acid catalysts as active agents. As used herein, the term acid catalysts refers to any species that serves as a proton source, thereby facilitating a chemical reaction. In one type of embodiment, the acid catalyst will be a non-oxidizing organic acid. A suitable organic acid is para-toluenesulfonic acid. In some embodiments, active agents that are acid catalysts will facilitate reactions including, but not limited to, acetalization, esterification or transesterification. Additional acid catalyzed reactions are well known in the art.

In one class of embodiments, active agents will include metal catalysts. These catalysts mediate reactions including, but not limited to, oxidation or reduction, hydrogenation, carbonylation, C—H bond activation, and bleaching. Suitable metals for use as metal catalysts include, but are not limited to the VIIIA and IB transition metals, for example, iron, cobalt, nickel, copper, platinum, rhodium, ruthenium, silver, osmium, gold and iridium. The metal that mediates catalysis can be of any suitable oxidation state.

In alternative embodiments, the active agent may optionally be an ion scavenger. Suitable ion scavengers include, but are not limited to, zeolites. Optionally, zeolites can be added to water-soluble packets comprising laundry detergents or dish washing detergents enclosed within, as a water softener.

Inorganic and organic bleaches are suitable cleaning active agents for use herein. Inorganic bleaches include perhydrate salts including, but not limited to, perborate, percarbonate, perphosphate, persulfate and persilicate salts. The inorganic perhydrate salts are normally the alkali metal salts. Alkali metal percarbonates, particularly sodium percarbonate are suitable perhydrates for use herein. Organic bleaches can include organic peroxyacids including diacyl and tetraacylperoxides, especially, but not limited to, diperoxydodecanedioc acid, diperoxytetradecanedioc acid, and diperoxyhexadecanedioc acid. Dibenzoyl peroxide is a suitable organic peroxyacid according to the disclosure. Other organic bleaches include the peroxy acids, particular examples being the alkylperoxy acids and the arylperoxy acids.

In one class of embodiments, active agents can comprise bleach sensitizers, including organic peracid precursors that enhance the bleaching action in the course of cleaning at temperatures of 60° C. and below. Bleach sensitizers suitable for use herein include compounds which, under perhydrolysis conditions, give aliphatic peroxoycarboxylic acids having from 1 to 10 carbon atoms, or from 2 to 4 carbon atoms, and/or optionally substituted perbenzoic acid. Suitable substances bear O-acyl and/or N-acyl groups of the number of carbon atoms specified and/or optionally substituted benzoyl groups. Suitable substances include, but are not limited to, polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), carboxylic anhydrides, in particular phthalic anhydride, acylated polyhydric alcohols, in particular triacetin, ethylene glycol diacetate and 2,5-diacetoxy-2,5-dihydrofuran and also triethylacetyl citrate (TEAC).

In embodiments that comprise fabric softeners as active agents, various through-the-wash fabric softeners, especially the impalpable smectite clays of U.S. Pat. No. 4,062,647, incorporated herein by reference in its entirety, as well as other softener clays known in the art, can optionally be used to provide fabric softener benefits concurrently with fabric cleaning. Clay softeners can be used in combination with amine and cationic softeners as disclosed, for example, in U.S. Pat. Nos. 4,375,416 and 4,291,071, incorporated herein by reference in their entireties.

In embodiments, the active agent can include disinfectants. Disinfectants suitable for use herein can include, but are not limited to, hydrogen peroxide, inorganic peroxides and precursors thereof, sodium metabisulfite, quaternary ammonium cation based compounds, chlorine, activated carbon, and hypochlorite.

In embodiments, the active agent can include surfactants. Suitable surfactants for use herein can include, but are not limited to, propylene glycols, diethylene glycols, monoethanolamine, polyoxyethylenated polyoxypropylene glycols, alcohol ethoxylates, alkylphenol ethoxylates, tertiary acetylenic glycols and alkanolamides (nonionics), polyoxyethylenated amines, quaternary ammonium salts and quaternized polyoxyethylenated amines (cationics), alkali metal salts of higher fatty acids containing about 8 to 24 carbon atoms, alkyl sulfates, alkyl polyethoxylate sulfates and alkylbenzene sulfonates (anionics), amine oxides, N-alkylbetaines and sulfobetaines (zwitterionics), dioctyl sodium sulfosuccinate, lactylated fatty acid esters of glycerin and propylene glycol, lactylic esters of fatty acids, sodium alkyl sulfates, polysorbate 20, polysorbate 60, polysorbate 65, polysorbate 80, lecithin, acetylated fatty acid esters of glycerin and propylene glycol, and acetylated esters of fatty acids, and combinations thereof.

Active agents may be solids or liquids. Active agents that are solids can have an average particle size (e.g., Dv50) of at least about 0.01 μm, or a size in a range of about 0.01 μm to about 2 mm, for example. Liquid active agents may be applied directly to the nonwoven web, mixed with a carrier powder, or microencapsulated. In embodiments that comprise a carrier powder, the average particle size of the carrier powder can be at least about 0.01 μm, or in a range of about 0.01 μm to about 2 mm, for example.

In one class of embodiments the active agent is encapsulated, allowing for the controlled release of the active agent. Suitable microcapsules can include or be made from one or more of melamine formaldehyde, polyurethane, urea formaldehyde, chitosan, polymethyl methacrylate, polystyrene, polysulfone, poly tetrahydrofuran, gelatin, gum arabic, starch, polyvinyl pyrrolidone, carboxymethylcellulose, hydroxyethylcellulose, methylcellulose, arabinogalactan, polyvinyl alcohol, polyacrylic acid, ethylcellulose, polyethylene, polymethacrylate, polyamide, poly (ethylenevinyl acetate), cellulose nitrate, silicones, poly(lactideco-glycolide), paraffin, carnauba, spermaceti, beeswax, stearic acid, stearyl alcohol, glyceryl stearates, shellac, cellulose acetate phthalate, zein, and combinations thereof. In one type of embodiment, the microcapsule is characterized by a mean particle size (e.g., Dv50) of at least about 0.1 micron, or in a range of about 0.1 micron to about 200 microns, for example. In alternate embodiments, the microcapsules can form agglomerates of individual particles, for example wherein the individual particles have a mean particle size of at least about 0.1 micron, or in a range of about 0.1 micron to about 200 microns.

The fibers to be treated can be formed by any process known in the art, for example, wet cool gel spinning, thermoplastic fiber spinning, melt blowing, spun bonding, electro-spinning, rotary spinning, continuous filament producing operations, tow fiber producing operations, and combinations thereof.

In embodiments, the fibers comprise fibers formed by wet cool gel spinning, melt blowing, spun bonding, or a combination thereof. In embodiments, the fibers comprise fibers that are formed by wet cool gel spinning. In embodiments, the fibers comprise water-soluble fibers and nonwoven webs prepared therefrom are formed in a continuous melt blown process. In embodiments, the fibers comprise water-soluble fibers and nonwoven webs prepared therefrom are formed in a continuous spun bond process. It is standard in the art to refer to fibers and nonwoven webs by the process used to prepare the same. Thus, any reference herein to, for example, a "melt blown fiber" or a "carded nonwoven web" should not be understood to be a product-by-process limitation for a particular melt blown or carding method, but rather merely identifying a particular fiber or web. Processing terms may therefore be used to distinguish fibers and/or nonwovens, without limiting the recited fiber and/or nonwoven to preparation by any specific process.

The fibers to be treated can be formed as bicomponent fibers. As used herein, and unless specified otherwise, "bicomponent fibers" do not refer to a fiber including a blend of fiber forming materials but, rather, refer to fibers including two or more distinct regions of fiber forming materials, wherein the composition of the fiber forming materials differ by region. Examples of bicomponent fibers include, but are not limited to, core-sheath (or core-shell) bicomponent fibers, island in the sea bicomponent fibers, and side-by-side bicomponent fibers. Core-sheath bicomponent fibers generally include a core having a first composition of fiber forming materials (e.g., a single fiber forming material or a first blend of fiber forming materials) and a sheath having a second composition of fiber forming materials (e.g., a single fiber forming material that is different from the core material, or a second blend of fiber forming materials that is different from the first blend of fiber forming materials of the core). Island in the sea bicomponent fibers generally include a first, continuous, "sea" region having a first composition of fiber forming materials and discreet "island" regions dispersed therein having a second composition of fiber forming materials that is different from the first composition. Side-by-side bicomponent fibers generally include a first region running the length of the fiber and including a first composition of fiber forming materials adjacent to at least a second region running the length of the fiber and including second composition of fiber forming materials that is different from the first composition.

The shape of the fiber is not particularly limited and can have transverse cross-sectional shapes including, but is not limited to, round, oval (also referred to as ribbon), triangular (also referred to as delta), trilobal, and/or other multi-lobal shapes (FIG. 1). It will be understood that the shape of the fiber need not be perfectly geometric, for example, a fiber having a round transverse cross-sectional shape need not have a perfect circle as the transverse cross-sectional area, and a fiber having a triangular transverse cross-sectional shape generally has rounded corners.

It will be understood that the diameter of a fiber refers to the transverse cross-section diameter of the fiber along the longest transverse cross-sectional axis. When a fiber is described as having (or not having) a particular diameter, unless specified otherwise, it is intended that the specified diameter is the average diameter for the specific fiber type referenced, i.e., a plurality of fibers prepared from polyvinyl alcohol fiber forming material has an arithmetic average fiber diameter over the plurality of fibers. For shapes not typically considered to have a "diameter", e.g., a triangle or a multi-lobal shape, the diameter refers to the diameter of a circle circumscribing the fiber shape (FIG. 1).

The fibers of the disclosure may have a diameter in a range of about 10 micron to 300 micron, for example, at least 10 micron, at least 15 micron, at least 20 micron, at least 25 micron, at least 50 micron, at least 100 micron, or at least 125 micron and up to about 300 micron, up to about 275 micron, up to about 250 micron, up to about 225 micron, up to about 200 micron, up to about 100 micron, up to about 50 micron, up to about 45 micron, up to about 40 micron, or up to about 35 micron for example in a range of about 10 micron to about 300 micron, about 50 micron to about 300 micron, about 100 micron to about 300 micron, about 10 micron to about 50 micron, about 10 micron to about 45 micron, or about 10 micron to about 40 micron. In embodiments, the fibers can have a diameter greater than 100 micron to about 300 micron. In embodiments, the fibers comprise cellulose and have a diameter in a range of about 10 micron to about 50 micron, about 10 micron to about 30 micron, about 10 micron to about 25 micron, about 10 micron to about 20 micron, or about 10 micron to about 15 micron. In embodiments, the fibers comprise a water-soluble fiber forming material and have a diameter of about 50 micron to about 300 micron, about 100 micron to about 300 micron, about 150 micron to about 300 micron, or about 200 micron to about 300 micron. In embodiments, the diameters of a plurality of the water-soluble fibers used to prepare a nonwoven web of the disclosure have diameters that are substantially uniform. As used herein, fiber diameters are "substantially uniform" if the variance in diameter between fibers is less than 10%, for example 8% or less, 5% or less, 2% or less, or 1% or less. Fibers having substantially uniform diameters can be prepared by a wet cooled gel spinning process or a thermoplastic fiber spinning process. Further, when a blend of fiber types are used, the average diameter of the fiber blend can be determined using a weighted average of the individual fiber types.

The fibers of the disclosure can be of any length. In embodiments, the length of the fibers can be in a range of about 20 mm to about 100 mm, about 20 to about 90, about 30 mm to about 80 mm, about 10 mm to about 60 mm, or about 30 mm to about 60 mm, for example, at least about 30 mm, at least about 35 mm, at least about 40 mm, at least about 45 mm, or at least about 50 mm, and up to about 100 mm, up to about 95 mm, up to about 90 mm, up to about 80 mm, up to about 70 mm, or up to about 60 mm. In embodiments, the length of the fibers can be less than about 30 mm or in a range of about 0.25 mm to less than about 30 mm, for example, at least about 0.25 mm, at least about 0.5 mm, at least about 0.75 mm, at least about 1 mm, at least about 2.5 mm, at least about 5 mm, at least about 7.5 mm, or at least about 10 mm and up to about 29 mm, up to about 28 mm, up to about 27 mm, up to about 26 mm, up to about 25 mm, up to about 20 mm, or up to about 15 mm. The fibers can be prepared to any length by cutting and/or crimping an extruded polymer mixture. In embodiments, the fiber can be a continuous filament, for example, prepared by processes such as spun bonding, melt blowing, electro-spinning, and rotary spinning wherein a continuous filament is prepared and provided directly into a web form. Further, when a blend of fiber types are used, the average length of the fibers can be determined using a weighted average of the individual fiber types.

Figures 6A, 6B:
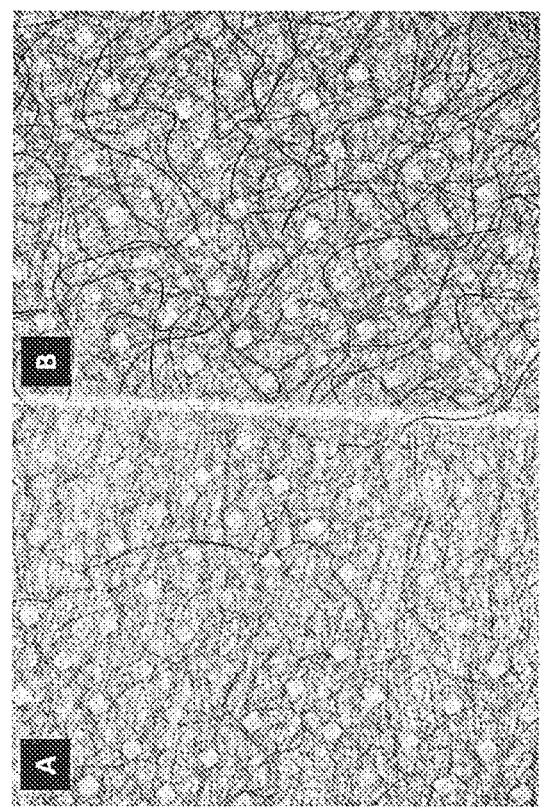
FIG. 6A is a micrograph image of a nonwoven web of the disclosure having a softness rating of 1.
FIG. 6B is a micrograph image of a nonwoven web of the disclosure having a softness rating of 5.

The fibers of the disclosure can have any length to diameter (L/D) ratio. In embodiments, length to diameter ratio of the fibers can be greater than about 2, greater than about 3, greater than about 4, greater than about 6, greater than about 10, greater than about 50, greater than about 60, greater than about 100, greater than about 200, greater than about 300, greater than about 400, or greater than about 1000. Advantageously, the tactility of a nonwoven web can be controlled using the L/D ratio of the fibers and the respective amounts of fibers having various L/D ratios in the nonwoven composition. In general, as the L/D of the fiber decreases, the stiffness and resistance to bending increases, providing a rougher hand feel. The fibers of the disclosure generally impart a rough feel to a nonwoven web including same, when the fibers have a low L/D ratio in a range of about 0.5 to about 15, or about 0.5 to about 25, or about 1 to about 5. Such low L/D fibers can be provided in a nonwoven web in an amount in a range of about 0 to about 50% by weight, based on the total weight of the fibers in the nonwoven web, for example, in a range of about 0.5 wt. % to about 25 wt. %, or about 1 wt. % to about 15 wt. %. If the amount of low L/D fibers in a nonwoven web is not known, the amount can be estimated by visual inspection of a micrograph of a nonwoven web. As shown in FIG. 6, the population of fibers having a visibly larger diameter and shorter cut rate, based on the total fiber population can be observed. FIG. 6A is a micrograph of a nonwoven web having 0% of low L/D fibers and a softness rating of 1, whereas FIG. 6B is a micrograph of a nonwoven web having 25% of low L/D fibers and a softness rating of 5.

The fibers of the disclosure can have any tenacity. The tenacity of the fiber correlates to the coarseness of the fiber. In general, as the tenacity of the fiber decreases the coarseness of the fiber increases. Fibers of the disclosure can have a tenacity in a range of about 1 to about 100 cN/dtex, or about 1 to about 75 cN/dtex, or about 1 to about 50 cN/dtex, or about 1 to about 45 cN/dtex, or about 1 to about 40 cN/dtex, or about 1 to about 35 cN/dtex, or about 1 to about 30 cN/dtex, or about 1 to about 25 cN/dtex, or about 1 to about 20 cN/dtex, or about 1 to about 15 cN/dtex, or about 1 to about 10 cN/dtex, or about 1 to about 5 cN/dtex, or about 3 to about 8 cN/dtex, or about 4 to about 8 cN/dtex, or about 6 to about 8 cN/dtex, or about 4 to about 7 cN/dtex, or about 10 to about 20, or about 10 to about 18, or about 10 to about 16, or about 1 cN/dtex, about 2 cN/dtex, about 3 cN/dtex, about 4 cN/dtex, about 5 cN/dtex, about 6 cN/dtex, about 7 cN/dtex, about 8 cN/dtex, about 9 cN/dtex, about 10 cN/dtex, about 11 cN/dtex, about 12 cN/dtex, about 13 cN/dtex, about 14 cN/dtex, or about 15 cN/dtex. In embodiments, the fibers can have a tenacity of about 3 cN/dtex to about 10 cN/dtex. In embodiments, the fibers can have a tenacity of about 7 cN/dtex to about 10 cN/dtex. In embodiments, the fibers can have a tenacity of about 4 cN/dtex to about 8 cN/dtex. In embodiments, the fibers can have a tenacity of about 6 cN/dtex to about 8 cN/dtex.

The fibers of the disclosure can have any fineness. The fineness of the fiber correlates to how many fibers are present in a transverse cross-section of a yarn of a given thickness. Fiber fineness is the ratio of fiber mass to length. The main physical unit of fiber fineness is 1 tex, which is equal to 1000 m of fiber weighing 1 g. Typically, the unit dtex is used, representing 1 g/10,000 m of fiber. The fineness of the fiber can be selected to provide a nonwoven web having suitable stiffness/hand-feel of the nonwoven web, torsional rigidity, reflection and interaction with light, absorption of dye and/or other actives/additives, ease of fiber spinning in the manufacturing process, and uniformity of the finished article. In general, as the fineness of the fibers increases the nonwovens resulting therefrom demonstrate higher uniformity, improved tensile strengths, extensibility and luster. Additionally, without intending to be bound by theory it is believed that finer fibers will lead to slower dissolution times as compared to larger fibers based on density. Further, without intending to be bound by theory, when a blend of fibers is used, the average fineness of the fibers can be determined using a weighted average of the individual fiber components. Fibers can be characterized as very fine (dtex 1.22), fine (1.22 dtex 1.54), medium (1.54 dtex 1.93), slightly coarse (1.93 dtex 2.32), and coarse (dtex 2.32). The nonwoven web of the disclosure can include fibers that are very fine, fine, medium, slightly coarse, or a combination thereof. In embodiments, the fibers have a fineness in a range of about 1 dtex to about 10 dtex, about 1 dtex to about 7 dtex, about 1 dtex to about 5 dtex, about 1 dtex to about 3 dtex, or about 1.7 dtex to about 2.2 dtex. In embodiments, fibers have a fineness of about 1.7 dtex. In embodiments, fibers have a fineness of about 2.2 dtex.

Wet Cooled Gel Spinning

In embodiments, the fibers of the disclosure are formed according to a wet cooled gel spinning process, the wet cooled gel spinning process including the steps of (a) dissolving the fiber forming material (polymers) in solution to form a polymer mixture, the polymer mixture optionally including auxiliary agents;

(b) extruding the polymer mixture through a spinneret nozzle to a solidification bath to form an extruded polymer mixture;

(c) passing the extruded polymer mixture through a solvent exchange bath;

(d) optionally wet drawing the extruded polymer mixture; and (e) finishing the extruded polymer mixture to provide the fibers.

The solvent in which the fiber forming polymer is dissolved can suitably be any solvent in which the polymer is soluble. In embodiments, the solvent in which the polymer is dissolved includes a polar aprotic solvent. In embodiments, the solvent in which the polymer is dissolved includes dimethyl sulfoxide (DMSO).

In general, the solidification bath includes a cooled solvent for gelling the extruded polymer mixture. The solidification bath can generally be at any temperature that facilitates solidification of the extruded polymer mixture. The solidification bath can include a mixture of a solvent in which the polymer is soluble and a solvent in which the polymer is not soluble. The solvent, in which the polymer is not soluble, is generally the primary solvent, wherein the solvent, in which the polymer is not soluble, makes up greater than 50% of the mixture.

After passing through the solidification bath, the extruded polymer mixture gel can be passed through one or more solvent replacement baths. The solvent replacement baths are provided to replace the solvent in which the polymer is soluble with the solvent in which the polymer is not soluble to further solidify the extruded polymer mixture and replace the solvent in which the polymer is soluble with a solvent that will more readily evaporate, thereby reducing the drying time. Solvent replacement baths can include a series of solvent replacement baths having a gradient of solvent in which the polymer is soluble with the solvent in which the polymer is not soluble, a series of solvent replacement baths having only the solvent in which the polymer is not soluble, or a single solvent replacement bath having only the solvent in which the polymer is not soluble.

Finished fibers are sometimes referred to as staple fibers, shortcut fibers, or pulp. In embodiments, finishing includes drying the extruded polymer mixture. In embodiments, finishing includes cutting or crimping the extruded polymer mixture to form individual fibers. Wet drawing of the extruded polymer mixture provides a substantially uniform diameter to the extruded polymer mixture and, thus, the fibers cut therefrom. Drawing is distinct from extruding, as is well known in the art. In particular, extruding refers to the act of making fibers by forcing the resin mixture through the spinneret head whereas drawing refers to mechanically pulling the fibers in the machine direction to promote polymer chain orientation and crystallinity for increased fiber strength and tenacity.

In embodiments wherein the fibers are prepared from a wet cooled gel spinning process, the fiber forming polymer can be generally any fiber forming polymer or blend thereof, e.g., two or more different polymers, as generally described herein. In refinements of the foregoing embodiments, the polymer(s) can have any degree of polymerization (DP), for example, in a range of 10 to 10,000,000, for example, at least 10, at least 20, at least 50, at least 100, at least 200, at least 300, at least 400, at least 500, at least 750, or at least 1000 and up to 10,000,000, up to 5,000,000, up to 2,500,00, up to 1,000,000, up to 900,000, up to 750,000, up to 500,000, up to 250,000, up to 100,000, up to 90,000, up to 75,000, up to 50,000, up to 25,000, up to 12,000, up to 10,000, up to 5,000, or up to 2,500, for example in a range of 1000 to about 50,000, 1000 to about 25,000, 1000 to about 12,000, 1000 to about 5,000, 1000 to about 2,500, about 50 to about 12,000, about 50 to about 10,000, about 50 to about 5,000, about 50 to about 2,500, about 50 to about 1000, about 50 to about 900, about 100 to about 800, about 150 to about 700, about 200 to about 600, or about 250 to about 500. In embodiments, the DP is at least 1,000. In embodiments, the fiber forming polymer comprises a polyvinyl alcohol polymer having a degree of polymerization (DP) in a range of 1000 to about 50,000, 1000 to about 25,000, 1000 to about 12,000, 1000 to about 5,000, 1000 to about 2,500, about 50 to about 12,000, about 50 to about 10,000, about 50 to about 5,000, about 50 to about 2,500, about 50 to about 1000, about 50 to about 900, about 100 to about 800, about 150 to about 700, about 200 to about 600, or about 250 to about 500. In embodiments, the fiber forming polymer comprises a polyvinyl alcohol polymer having a DP in a range of 1000 to about 50,000, 1000 to about 25,000, 1000 to about 12,000, 1000 to about 5,000, or 1000 to about 2,500.

The wet cooled gel spinning process advantageously provides one or more benefits such as providing a fiber that includes a blend of water-soluble polymers, providing control over the diameter of the fibers, providing relatively large diameter fibers, providing control over the length of the fibers, providing control over the tenacity of the fibers, providing high tenacity fibers, providing fibers from polymers having a large degree of polymerization, and/or providing fibers which can be used to provide a self-supporting nonwoven web. Continuous processes such as spun bond, melt blown, electro-spinning and rotary spinning generally do not allow for blending of water-soluble polymers (e.g., due to difficulties matching the melt index of various polymers), forming large diameter (e.g., greater than 50 micron) fibers, controlling the length of the fibers, providing high tenacity fibers, or the use of polymers having a high degree of polymerization. Further, the wet cooled gel spinning process advantageously is not limited to polymers that are only melt processable and, therefore, can access fibers made from fiber forming materials having very high molecular weights, high melting points, low melt flow index, or a combination thereof, providing fibers having stronger physical properties and different chemical functionalities compared to fibers prepared by a heat extrusion process.

Methods of preparing staple fibers and continuous fibers are well known in the art. Once the staple fibers or continuous fibers are carded, the nonwoven web is bonded. Methods of bonding staple fibers are well known in the art and can include through air bonding (thermal), calendar bonding (thermal with pressure), and chemical bonding. The nonwoven web of the disclosure can be thermally or chemically bonded. The nonwoven web can be generally porous with varying pore size, morphology and web heterogeneity. Fiber physical properties and the type of bonding can affect the porosity of the resulting nonwoven web. Calendar bonding is achieved by applying heat and pressure, and typically maintains the pore size, shape, and alignment produced by the carding process. The conditions for calendar bonding can be readily determined by one of ordinary skill in the art. In general, if the heat and/or pressure applied is too low, the fibers will not sufficiently bind to form a free-standing web and if the heat and/or pressure is too high, the fibers will begin to meld together. The fiber chemistry dictates the upper and lower limits of heat and/or pressure for calendar bonding. Without intending to be bound by theory, it is believed that at temperatures above 235° C., polyvinyl alcohol based fibers degrade. Methods of embossment for calendar bonding of fibers are known. The embossing can be a one-sided embossing or a double-sided embossing. Typically, embossing of water-soluble fibers includes one-sided embossing using a single embossing roll consisting of an ordered circular array and a steel roll with a plain surface. As embossing is increased (e.g., as surface features are imparted to the web), the surface area of the web is increased. Without intending to be bound by theory, it is expected that as the surface are of the web is increased, the solubility of the web is increased. Accordingly, the solubility properties of the nonwoven web can be advantageously tuned by changing the surface area through embossing.

In contrast to calendar bonding, chemical bonding uses a binder solution of the waste polymer left over from preparing the fibers to coat the carded fibers under pressure, which can result in smaller, less ordered pores relative to the pores as carded. The solvent can be any solvent that solubilizes the binder. The solvent of the chemical bonding solution is water in some embodiments. Without intending to be bound by theory, it is believed that if the polymer solution used for chemical bonding is sufficiently concentrated and/or sufficient pressure is applied, a nonporous water-dispersible nonwoven web can be formed. The solvent used in chemical bonding induces partial solubilization of the existing fibers in the web to weld and bond the fibers together. The polyvinyl alcohol binder provided in the solution assists in the welding process to provide a more mechanically robust web. The temperature of the polymer solution is not particularly limited and can be provided at room temperature (about 23° C.).

In some embodiments, a second layer of fibers can be used to bond the nonwoven web. Without intending to be bound by theory, it is believed that fibers prepared from by a melt blown process, for example, water-soluble fibers, can be used to bond the nonwoven web using an in-line process. In particular, a nonwoven web can be passed under a melt blown process station such that the melt blown fibers are deposited after melt extrusion and as the melt blown fibers cool and solidify, they bond to each other and to the nonwoven web on which they are deposited. Melt blown fibers can be micro- to nano-scale in length and can be provided on the nonwoven web such that the melt blown fibers make up about 15%, about 12%, about 10%, about 8%, about 6%, or about 5%, by weight of the final nonwoven web, based on the total weight of the fibers in the final nonwoven web. Without intending to be bound by theory, it is believed that the inclusion of about 5% to about 15% of melt blown fibers can increase the mechanical integrity of the nonwoven web, without substantially changing the solubility properties of the nonwoven web. In general, when a polyvinyl alcohol fiber forming material is used to prepare a melt blown fiber, the polyvinyl alcohol polymer will be a homopolymer or copolymer as melt blown processes require low viscosity and high melt flow index polymers.

Pore sizes can be determined using high magnification and ordered surface analysis techniques including, but not limited to Brunauer-Emmett-Teller theory (BET), small angle X-ray scattering (SAXS), and molecular adsorption.

In general, the fibers of the disclosure can be formed by any fiber process known in the art and are then post-process treated by hydrolysis.

The disclosure provides a method of treating a fiber including a hydrolyzable polymer such as a polymer comprising at least one of a vinyl acetate moiety or a vinyl alcohol moiety as described herein. In embodiments, the method includes admixing a fiber comprising such a polymer having a degree of hydrolysis less than 100% and a hydrolysis agent solution to increase the degree of hydrolysis of at least a portion of the fiber. The hydrolysis agent solution can include a hydrolysis agent and a solvent. The degree of hydrolysis of the fiber after admixing with the hydrolysis agent solution can be determined according to the Titration Method or Attenuated Total Reflection-Fourier-Transform Infrared (ATR-FTIR) Spectroscopy disclosed herein. The Titration Method determines an average degree of hydrolysis for a fiber. For a fiber characterized by a constant degree of hydrolysis across a transverse cross-section of the fiber, the constant degree of hydrolysis is the average degree of hydrolysis for the fiber. For a fiber characterized by a transverse cross-section of the fiber having a core-sheath type distribution or a gradient distribution of the degree of hydrolysis, the Titration test provides the average degree of hydrolysis across all sections of the fiber. As used herein, and unless specified otherwise, at least a portion of a fiber has an increased degree of hydrolysis if any portion of the fiber (e.g., exterior, sheath portion, interior) has an increased degree of hydrolysis after admixing, relative to the degree of hydrolysis of the starting fiber. It will be understood that an increase in degree of hydrolysis to any portion of the fiber will result in an increase in the average degree of hydrolysis of the fiber as determined by the Titration Method. Thus, it will be understood that the degree of hydrolysis of at least a portion of the polymer in the fiber will have increased if the average degree of hydrolysis of the fiber, as determined by the Titration Method, is greater after admixing the fiber with the hydrolysis agent solution, relative to the average degree of hydrolysis of the fiber prior to admixing. The technique of ATR-FTIR provides accurate measurements in a degree of hydrolysis on a surface of a sample based on the signals corresponding to chemical groups, such as a carbonyl group.

In general, admixing can include immersing the fibers in the hydrolysis agent solution. In embodiments, admixing can include stirring the mixture of the fibers and the hydrolysis agent solution.

In embodiments, the method comprises admixing the hydrolysis agent solution and the fiber under conditions sufficient to provide a predetermined degree of hydrolysis and/or a predetermined degree of hydrolysis increase to the fiber. In general, the degree of hydrolysis of the treated fiber and/or the increase in the degree of hydrolysis of the treated fiber can be designed and controlled by varying the reaction conditions. Reaction conditions that can be modified to provide a predetermined degree of hydrolysis and/or increase in degree of hydrolysis include the selection of the hydrolysis agent, selection of the concentration of the hydrolysis agent in the hydrolysis agent solution, reaction (admixing) time, reaction (admixing) temperature, selection of solvent for the hydrolysis agent solution, and optional inclusion of an activator.

In general, as the reaction time increases, the degree of hydrolysis will increase. Thus, the reaction time can be selected to provide a desired increase in the degree of hydrolysis of the polymer that makes up the fiber, e.g., a copolymer (or modified copolymer) having vinyl acetate and vinyl alcohol moieties. The reaction time can be from about 1 minute to about 48 hours, for example, about 1 minute to about 10 minutes (e.g., 1 minute, 2 minutes, 5 minutes, or 10 minutes), about 2 minutes to about 36 hours, about 2 minutes to about 24 hours, about 2 minutes to about 12 hours, about 2 minutes to about 6 hours, about 2 minutes to about 4 hours, about 2 minutes to about 2 hours, about 2 minutes to about 1 hour, about 5 minutes to about 1 hour, about 5 minutes to about 2 hours, about 5 minutes to about 5 hours, about 5 minutes to about 10 hours, about 5 minutes to about 12 hours, about 5 minutes to about 24 hours, about 10 minutes to about 24 hours, about 15 minutes to about 24 hours, about 30 minutes to about 24 hours, about 1 hour to about 24 hours, about 2 hours to about 24 hours, about 3 hours to about 24 hours, about 4 hours to about 24 hours, about 5 hours to about 24 hours, about 6 hours to about 24 hours, about 8 hours to about 24 hours, about 10 hours to about 24 hours, about 12 hours to about 24 hours, about 12 hours to about 18 hours, about 14 hours to about 20 hours, or about 16 hours to about 24 hours. In embodiments, the admixing can be for about 2 minutes to about 48 hours. In embodiments, the admixing can be for about 12 to about 36 hours. In embodiments, the admixing can be for about 18 to about 28 hours.

In general, as the temperature of the reaction is increased, the rate of hydrolysis will increase. Thus, the temperature of the reaction can be selected in combination with reaction time to provide a desired increase in the degree of hydrolysis of the polymer that makes up the fiber, e.g., a copolymer (or modified copolymer) having vinyl acetate and vinyl alcohol moieties. The temperature of the reaction is not particularly limited so long as the fiber does not dissolve or decompose and the solvent remains a liquid under the heating conditions. The reaction temperature can be from about 10° C. to about 200° C., about 10° C. to about 190° C., about 10° C. to about 180° C., about 10° C. to about 170° C., about 10° C. to about 160° C., about 10° C. to about 150° C., about 10° C. to about 140° C., about 10° C. to about 130° C., about 10° C. to about 120° C., about 10° C. to about 110° C., about 10° C. to about 100° C., about 10° C. to about 90° C., about 10° C. to about 80° C., about 10° C. to about 70° C., about 10° C. to about 60° C., about 10° C. to about 50° C., about 10° C. to about 40° C., about 10° C. to about 30° C., about 20° C. to about 100° C., about 20° C. to about 90° C., about 20° C. to about 80° C., about 30° C. to about 100° C., about 30° C. to about 90° C., about 30° C. to about 80° C., about 30° C. to about 70° C., about 30° C. to about 60° C., or about 30° C. to about 50° C. Without intending to be bound by theory, it is believed that at higher temperatures as the polarity of the solvent increases the fibers may begin to swell, gel, and/or dissolve. Accordingly, the temperature of the reaction can be selected in combination with the solvent such that the fiber will remain insoluble and will not decompose. In embodiments, the method further comprises heating the mixture of the fiber and the hydrolysis agent solution.

The selection of the hydrolysis agent can affect the rate of the hydrolysis reaction. Thus, the hydrolysis agent can be selected in combination with the reaction time and temperature to provide a desired increase in the degree of hydrolysis of the polymer that makes up the fiber, e.g., a copolymer (or modified copolymer) having vinyl acetate and vinyl alcohol moieties. In embodiments wherein the hydrolysis occurs by acid or base catalyzed transesterification of an ester or amide, the rate of the reaction can be modified based on the nucleophilic strength of the hydrolysis agent and, as a secondary factory, the solubility of the hydrolysis agent in the solvent of the hydrolysis agent solution. In embodiments wherein the hydrolysis occurs by reduction of a functional group to an —OH moiety, the rate of the reaction can be modified based on the reducing strength of the hydrolysis agent and, as a secondary factor, the solubility of the hydrolysis agent in the solvent of the hydrolysis agent solution.

The hydrolysis agent can be any agent that can hydrolyze or reduce a functional group on the polymer backbone to an —OH moiety, and/or catalyze same. Non-limiting examples of hydrolysis agents include, but are not limited to, a metallic hydroxide, a metal hydride, a sulfite, sulfur dioxide, a dithionate, a thiosulfate, a hydrazine, oxalic acid, formic acid, ascorbic acid, dithiothreitol, a phosphite, a hypophosphite, phosphorous acid, sulfuric acid, sulphonic acid, hydrochloric acid, ammonium hydroxide, water, and combinations thereof. In embodiments, the hydrolysis agent comprises a metallic hydroxide, a metal hydride, a sulfite, sulfur dioxide, a dithionate, a thiosulfate, a hydrazine, oxalic acid, formic acid, ascorbic acid, dithiothreitol, a phosphite, a hypophosphite, phosphorous acid, sulfuric acid, sulphonic acid, hydrochloric acid, ammonium hydroxide, water, or a combination thereof. In embodiments, the hydrolysis agent comprises a metallic hydroxide, a metal hydride, a sulfite, a sulfur dioxide, a dithionate, a thiosulfate, a hydrazine, oxalic acid, formic acid, ascorbic acid, dithiothreitol, a phosphite, a hypophosphite, phosphorous acid, sulfuric acid, sulphonic acid, hydrochloric acid, ammonium hydroxide, or a combination thereof. In embodiments, the hydrolysis agent comprises a metallic hydroxide, a metal hydride, a sulfite, a sulfur dioxide, a dithionate, a thiosulfate, a hydrazine, oxalic acid, formic acid, ascorbic acid, dithiothreitol, a phosphite, a hypophosphite, phosphorous acid, ammonium hydroxide, or a combination thereof. In embodiments, the hydrolysis agent comprises a metallic hydroxide, ammonium hydroxide, or a combination thereof. In embodiments, the hydrolysis agent comprises a metallic hydroxide. In embodiments, the metallic hydroxide hydrolysis agent comprises an alkali metal hydroxide, an alkaline earth metal hydroxide, a main group metal hydroxide, or a combination thereof. In embodiments, the metallic hydroxide hydrolysis agent comprises sodium hydroxide, potassium hydroxide, calcium hydroxide, barium hydroxide, trialkyltin hydroxide, or a combination thereof. In embodiments, the metallic hydroxide hydrolysis agent comprises sodium hydroxide, potassium hydroxide, or a combination thereof. In embodiments, the metallic hydroxide hydrolysis agent comprises sodium hydroxide.

In general, as the concentration of hydrolysis agent in the hydrolysis agent solution increases, the rate of reaction will increase. Thus, the concentration of the hydrolysis agent can be selected in combination with the reaction time, reaction temperature, and selection of the hydrolysis agent to provide a desired increase in the degree of hydrolysis of the polymer that makes up the fiber, e.g., copolymer of vinyl acetate and vinyl alcohol. In general, the concentration of the hydrolysis agent in the hydrolysis solution can be any concentration. Typically, the concentration will be selected such that all of the hydrolysis agent provided is in solution. In embodiments, the hydrolysis agent can be provided in an amount of about 0.2% to about 75% (w/w) based on the weight of the solvent, for example, about 0.2% to about 75%, about 0.2% to about 50%, about 0.2% to about 25%, about 0.5% to about 20%, about 1% to about 18%, about 2% to about 16%, about 5% to about 15%, about 8% to about 12%, or about 10%. In embodiments, the hydrolysis agent is provided in an amount of about 0.2% to about 25% (w/w), based on the weight of the solvent. In embodiments, the hydrolysis agent is provided in an amount of about 2% to about 25% (w/w), based on the weight of the solvent. In embodiments, the hydrolysis agent is provided in an amount of about 5% to about 15% (w/w), based on the weight of the solvent.

The solvent of the hydrolysis agent solution can generally be any solvent in which the hydrolysis agent is soluble and the fiber to be treated is insoluble at the temperature at which the treatment takes place for the duration of contact of the fiber with the solvent. In embodiments, the fiber is insoluble in the solvent prior to treatment. In embodiments, the fiber is insoluble in the solvent during treatment. In embodiments, the fiber is insoluble in the solvent after treatment. In general, the solvent can be selected in combination with the reaction time, reaction temperature, selection of the hydrolysis agent and concentration thereof to provide a desired increase in the degree of hydrolysis of the polymer that makes up the fiber, e.g., copolymer of vinyl acetate and vinyl alcohol. As the polarity of the solvent increases, the diffusion of the solvent into the polymer matrix of the fiber generally increases, resulting in an increase in the diffusion of the hydrolysis agent into the polymer matrix. Without intending to be bound by theory, it is believed that as the polarity of the solvent increases, the degree of hydrolysis of the inner/core section of the fiber can increase, such that the degree of hydrolysis can be increased across a transverse cross-section of the fiber. Further, without intending to be bound by theory, as the polarity of the solvent decrease, the diffusion of the solvent into the polymer matrix of the fiber generally decreases, such that the degree of hydrolysis can be increased only at the polymer at a portion of the surface/exterior/sheath/shell of the fiber. Hydrolysis of the polymer of the fiber at a portion of the surface/exterior/sheath/shell of the fiber also results in an average increase in the degree of hydrolysis across a transverse cross-section of the fiber. Further, without intending to be bound by theory, a combination of solvents can be used to provide a diffusion controlled radiant gradient of the degree of hydrolysis of the polymers of the treated fiber.

In embodiments, the solvent for the hydrolysis agent solution can be characterized by the Hansen Solubility Parameter (HSP). Without intending to be bound by theory, it is believed that the three HSP values, dispersion, molar volume, and hydrogen-bonding, are indicators of miscibility and, thus, solvation or swelling of polyvinyl alcohol by a particular solvent and further that it is believed hydrogen bonding is the largest predictor of these expected behavior, the summation of all the parameters, $H_{total}$, is also predictive. In general, when the HSP values of the solvent are less than the HSP values of the polyvinyl alcohol, the more dissimilar the HSP values are between the solvent and the polyvinyl alcohol, the lower the diffusivity of the solvent into the polyvinyl alcohol. Without intending to be bound by theory, it is believed that when the $H_{total}$ value of the solvent is about 4 to about 15 units lower than the $H_{total}$ value of the polyvinyl alcohol, the rate of solvent uptake and diffusivity of the solvent into the polyvinyl alcohol is such that a gradient of solvent uptake and, thus, hydrolysis agent uptake, will occur, providing a gradient in the degree of hydrolysis of the fiber across a transverse cross section with a higher degree of hydrolysis at a surface region, relative to an inner, core region. Without intending to be bound by theory, it is believed that when the $H_{total}$ value of the solvent is about 4 to about 15 units higher than the $H_{total}$ value of the polyvinyl alcohol, the rate of solvent uptake and diffusivity of the solvent into the polyvinyl alcohol is such that solvent uptake and, thus, hydrolysis agent uptake, will occur quickly providing a uniform degree of hydrolysis across a transverse cross-section of the polyvinyl alcohol fiber. Further, without intending to be bound by theory, it is believed that when the $H_{total}$ value of the solvent is more than 15 units lower than that of the polyvinyl alcohol of the fiber the diffusivity will be limited such that only an outer surface of the fiber will be treated with the hydrolysis agent and when the $H_{total}$ value of the solvent is more than 15 units higher than that of the polyvinyl alcohol of the fiber, the solvent will dissolve the polyvinyl alcohol of the fiber.

In embodiments, the solvent comprises a polar solvent. In embodiments, the solvent comprises octanol, heptanol, hexanol, pentanol, butanol, propanol, tetrahydrofuran, dichloromethane, acetone, ethanol, N-methylpyrrolidone, methanol, acetonitrile, ethylene glycol, N,N-dimethylformamide, glycerol, dimethyl sulfoxide, formic acid, water, or a combination thereof. In embodiments, the solvent comprises n-octanol, n-heptanol, n-hexanol, n-pentanol, n-butanol, isobutanol, sec-butanol, tert-butanol, n-propanol, isopropanol, acetone, ethanol, N-methylpyrrolidone, methanol, acetonitrile, N,N-dimethylformamide, dimethyl sulfoxide, formic acid, water, or a combination thereof. In embodiments, the solvent comprises n-propanol, acetone, ethanol, N-methylpyrrolidone, methanol, acetonitrile, N,N-dimethylformamide, dimethyl sulfoxide, formic acid, water, or a combination thereof. In embodiments, the solvent comprises an alcohol that is a liquid under the admixing conditions. In embodiments, the solvent comprises methanol. In embodiments, the solvent comprises methanol and at least one additional solvent. In embodiments, the solvent comprises methanol and water. In embodiments, the solvent comprises at least one of butanol, pentanol, hexanol, heptanol, and octanol in combination with water. In embodiments, the solvent comprises DMSO and water. In embodiments, the solvent comprises DMSO and water and the DMSO and water are provided in a weight ratio of about 40/60 to 80/20. Without intending to be bound by theory, it is believed that as the amount of water increases above 60% or the amount of DMSO increases above about 80%, the interaction of the respective solvents with polyvinyl alcohol increases, resulting in increased swelling and gelling of the polymer.

In embodiments, the solvent comprises a nonpolar solvent. In embodiments, the solvent comprises hexanes, cyclohexane, methylpentane, pentane, cyclopropane, dioxane, benzene, pyridine, xylene, toluene, diethyl ether, chloroform, or a combination thereof.

In embodiments, the solvent comprises a mixture of a first solvent and a second solvent. In embodiments, the first solvent comprises a polar solvent and the second solvent comprises a nonpolar solvent. In embodiments, the first solvent has a first dielectric constant and the second solvent has a second dielectric constant and the dielectric constant of the first solvent is higher than the dielectric constant of the second solvent. In embodiments, the first dielectric constant is 5 or less, 4 or less, 3 or less, or 2 or less. In embodiments, the second dielectric constant is greater than 5, greater than 7.5, greater than 10, greater than 15, greater than 18, greater than 20, greater than 25, or greater than 30. In embodiments, the difference between the first dielectric constant and the second dielectric constant is at least 3, at least 5, at least 8, or at least 10. In embodiments, wherein the solvent comprises a mixture of a first solvent and a second solvent, the first solvent and the second solvent can be provided in any ratio provided that the hydrolysis agent is soluble in the mixture and the fiber is not soluble in the mixture prior to treatment, during treatment, and after treatment. In embodiments, the first solvent and second solvent can be provided in a weight ratio of about 99/1 to about 1/99, about 95/5 to about 5/95, about 90/10 to 10/90, about 85/15 to about 15/85, about 80/20 to about 20/80, about 75/25 to about 25/75, about 70/30 to about 30/70, about 65/35 to about 35/65, about 60/40 to about 40/60, about 55/45 to about 45/55, or about 50/50.

In some embodiments, the first solvent is methanol and the second solvent is hexane. Methanol and hexane can be in any suitable ratio by weight or by volume. For example, a solvent including 10% of methanol and 90% hexane by weight catalyzes secondary saponification in at least one portion of a fiber comprising the polymer as described herein.

In embodiments, the methods of the disclosure further include admixing an activator with the fiber and the hydrolysis agent solution. The activator can be any additive that facilitates the treatment of the fiber by the hydrolysis agent. The activator can include a catalyst for reducing the activation energy of the reaction between the polymer of the fiber and the hydrolysis agent or a compound that facilitates diffusion of the hydrolysis agent into the polymer matrix, for example.

Figure 2C:
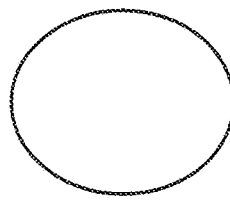
FIG. 2C shows the transverse cross-section of a round fiber characterized by the polymer having the same degree of hydrolysis across the transverse cross-section.
Figure 2B:
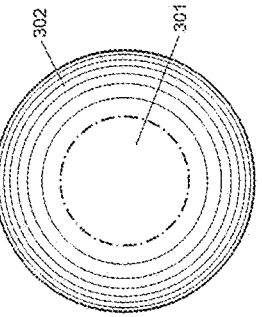
FIG. 2B shows the transverse cross-section of a round fiber characterized by an increasing gradient in the degree of hydrolysis of the polymer from an interior region 301 to a surface region 302.
Figure 2A:
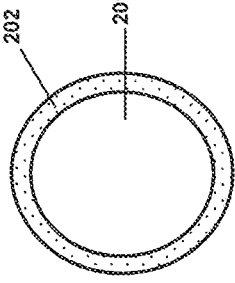
FIG. 2A shows the transverse cross-section of a round fiber characterized by a core-sheath structure, wherein the polymer of the sheath 202 has a higher degree of hydrolysis than the polymer of the core 201.
Figure 3:
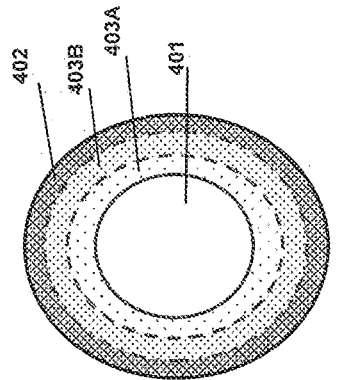
FIG. 3 shows the transverse cross-section of a round fiber having a first, core region 401, a second, sheath or shell region 402, and two intermediate regions 403A and 403B disposed between the first and second regions, the cross section of the fiber characterized by an increasing gradient in the degree of hydrolysis of the polymer from the first region to the second region.

The reaction conditions can also be selected to design and control the solubility mechanism and/or absorption capacity and retention of the treated fiber. For example, the reaction conditions can be selected to provide a fiber having a transverse cross-section characterized by (a) a core-sheath structure wherein the polymer of the sheath has a greater degree of hydrolysis than the polymer of the core (FIG. 2A), (b) an increasing radial gradient in the degree of hydrolysis of the polymer from an interior region to a surface region (FIG. 2B; FIG. 3), or (c) a consistent degree hydrolysis across the transverse cross-section (FIG. 2C) and the resulting fibers can have different solubility mechanisms (for example, immediate release, delayed release, or triggered release) and/or absorption capacity and retention properties. Reaction conditions that can be modified to provide a predetermined fiber structure include the selection of the hydrolysis agent, selection of the concentration of the hydrolysis agent in the hydrolysis agent solution, reaction (admixing) time, reaction (admixing) temperature, selection of solvent for the hydrolysis agent solution, and optional inclusion of an activator.

A fiber having a core-sheath structure can be prepared by treating a fiber having a polymer having a degree of hydrolysis of less than 100% as described herein with a hydrolysis agent solution under conditions sufficient to minimize the radial diffusion of the solvent and the hydrolysis agent into an inner core region of the fiber. Diffusion of the solvent and hydrolysis agent into an inner core region of the fiber can be minimized, for example, by selecting a short reaction time, a low reaction temperature, and/or including a nonpolar solvent. In embodiments, the admixing of the methods of the disclosure is performed under conditions sufficient to provide a polyvinyl alcohol fiber having a transverse cross-section characterized by a core-sheath structure, wherein the polymer of the sheath has a greater degree of hydrolysis than the polymer of the core. In embodiments, the conditions sufficient to provide a polyvinyl alcohol fiber having a transverse cross-section characterized by a core-sheath structure, wherein the polymer of the sheath has a greater degree of hydrolysis than the polymer of the core comprises including in the hydrolysis agent solution a solvent having a dielectric constant of 20 or less, 18 or less, 14 or less, or 10 or less. In embodiments, the conditions sufficient to provide a polyvinyl alcohol fiber having a transverse cross-section characterized by a core-sheath structure, wherein the polymer of the sheath has a greater degree of hydrolysis than the polymer of the core comprises admixing the fiber and the hydrolysis agent solution at a temperature in a range of about 10° C. to about 30° C., about 10° C. to about 25° C., or about 15° C. to about 25° C. In embodiments, the conditions sufficient to provide a polyvinyl alcohol fiber having a transverse cross-section characterized by a core-sheath structure, wherein the polymer of the sheath has a greater degree of hydrolysis than the polymer of the core comprises admixing the fiber and the hydrolysis agent solution for a time of about 2 minutes to about 6 hours, about 2 minutes to about 4 hours, about 5 minutes to about 3 hours, about 10 minutes to about 2 hours, or about 15 minutes to about 1 hour. In embodiments, the conditions sufficient to provide a polyvinyl alcohol fiber having a transverse cross-section characterized by a core-sheath structure, wherein the polymer of the sheath has a greater degree of hydrolysis than the polymer of the core comprises including in the hydrolysis agent solution a solvent having a dielectric constant of 20 or less, 18 or less, 14 or less, or 10 or less, admixing the fiber and the hydrolysis agent solution at a temperature in a range of about 10° C. to about 30° C., about 10° C. to about 25° C., or about 15° C. to about 25° C., and admixing the fiber and the hydrolysis agent solution for a time of about 2 minutes to about 6 hours, about 2 minutes to about 4 hours, about 5 minutes to about 3 hours, about 10 minutes to about 2 hours, or about 15 minutes to about 1 hour. Such fibers having a transverse cross-section characterized by a core-sheath structure wherein the polymer of the sheath has a greater degree of hydrolysis than the polymer of the core can provide delayed release properties of an active provided in the interior of the fiber, triggered release of an active provided in the interior of the fiber, increased absorbance relative to a fiber having a consistent degree of hydrolysis across a transverse cross-section, and/or improved retention of absorbed fluids relative to a fiber having a consistent degree of hydrolysis across a transverse cross-section.

As used herein and unless specified otherwise, "delayed release" of an active from a fiber means that the entirety of the active is not immediately released from the fiber when contacted with a solvent (usually water) under the conditions of an end use application of the fiber. For example, a fiber containing an active and used in a laundry application may not immediately release the entirety of the active under wash conditions. Rather, the active can diffuse from the fiber over time. As used herein and unless specified otherwise, "triggered release" of an active from a fiber means that none of the active is released from the fiber until a trigger condition is met. For example, a fiber containing an active and used in a laundry application may not release the active until the wash water reaches a predetermined temperature and/or pH.

Trigger conditions can include, but are not limited to, temperature, pH, UV/VIS radiation, IR radiation, presence of ions, presence of catalysts, or a combination thereof.

Without intending to be bound by theory, it is believed that fibers having a transverse cross-section characterized by a core-sheath structure wherein the polymer of the sheath has a greater degree of hydrolysis than the polymer of the core can have increased fluid absorption and/or retention relative to a fiber having a consistent degree of hydrolysis across a transverse cross-section because the presence of the sheath allows the core to swell when in contact with fluid, allowing increased absorbance capacity, without decomposition of the fiber, and will retain the fluid until the fiber is contacted with a triggering condition, such as immersion in hot water.

As the thickness of the sheath structure increases, the stability of a fiber having a core swollen and saturated with a fluid increases but the amount of polymer available in the core for absorbing a fluid decreases. The thickness of the sheath is can be controlled by controlling the diffusion of the hydrolysis agent into the polymer structure of the fiber. It will be understood that because treatment of the inner portions of the fiber is diffusion controlled, the sheath may have a variation in thickness around a perimeter of the fiber and the inner portion of the sheath may have a degree of hydrolysis that is less than the degree of hydrolysis of the polymer at the exterior surface of the sheath but greater than the degree of hydrolysis of the polymer at the center of the fiber. Thus in some embodiments, the transverse cross-section of the fiber can be characterized by a core-sheath structure and can also be characterized as having an increasing gradient from an inner portion of the fiber to an exterior portion of the fiber.

A fiber having a transverse cross-section characterized by an increasing radial gradient structure can be prepared by treating a fiber having a polymer such as a polyvinyl alcohol copolymer or a modified copolymer having a degree of hydrolysis of less than 100% with a hydrolysis agent solution under conditions sufficient to modify the radial diffusion of the solvent and the hydrolysis agent into an inner region of the fiber. In embodiments, a polyvinyl alcohol fiber having a transverse cross-section characterized by an increasing radial gradient structure from an inner region to an exterior region can be prepared using multiple solvents having different rates of diffusion (concurrently or stepwise), changing the temperature during admixing to modify the rate of diffusion of the solvent and hydrolysis agent into the fiber, and/or selecting the reaction time such that it is long enough to allow some hydrolysis agent diffuses into the inner region to modify the degree of hydrolysis of the polymer but is not so long as to allow the polymer of the inner portion to hydrolyze to the same extent as the polymer of the exterior/surface portion. In embodiments, the admixing of the methods of the disclosure is performed under conditions sufficient to provide a fiber having a transverse cross-section characterized by an increasing gradient in the degree of hydrolysis of the polymer from an interior region of the fiber to a surface region of the fiber. Such fibers having a transverse cross-section characterized by an increasing gradient of degree of hydrolysis can provide delayed release properties of an active provided in the interior of the fiber, triggered release of an active provided in the interior of the fiber, increased absorbance relative to a fiber having a consistent degree of hydrolysis across a transverse cross-section, and/or improved retention of absorbed fluids.

Fibers having a transverse cross-section characterized by a core-sheath structure and/or an increasing radial structure can have active agents loaded in the core/inner regions. Actives can be loaded to the core/inner regions by contacting a fiber with a solution of an active agent and allowing the active agent solution to diffuse into the polymer structure, resulting in the core/inner regions of the fiber to absorb the active agent solution and swell. The active agent can be any active agent disclosed herein that is soluble in the active agent solution solvent. The solvent can be any solvent disclosed herein. Without intending to be bound by theory, it is believed that as the polarity of the solvent increases, the rate of diffusion to the core/inner regions of the fiber increases. An exemplary solvent is water provided that the water of the active agent solution is maintained at a temperature below the solubility temperature of the polymer that makes up the core/inner region of the fiber and the sheath/shell/exterior region of the fiber.

A fiber having a transverse cross-section characterized by the polymer having the same degree of hydrolysis across (throughout) the transverse cross-section can be prepared by treating a fiber having a polymer such as a polyvinyl alcohol copolymer or a modified copolymer having a degree of hydrolysis of less than 100% with a hydrolysis agent solution under conditions sufficient to maximize the radial diffusion of the solvent and the hydrolysis agent into an inner core region of the fiber. Diffusion of the solvent and hydrolysis agent into an inner core region of the fiber can be maximized, for example, by selecting a long reaction time, a high reaction temperature, and/or including a highly polar solvent. In embodiments, the admixing of the methods of the disclosure is performed under conditions sufficient to provide a fiber having a transverse cross-section characterized by the polymer having the same degree of hydrolysis across the transverse cross-section.

Without intending to be bound by theory, it is believed that for a fiber comprising a polyvinyl alcohol copolymer or a modified copolymer as the fiber forming material, the average degree of hydrolysis across a transverse cross-section of the fiber informs on the solubility mechanism of the fiber and the absorbance capacity of the fiber. In particular, without intending to be bound by theory, it is believed that as the average degree of hydrolysis across the transverse cross-section of the fiber increases the longer the fiber is expected to survive in water as the temperature of the water increases. Additionally, without intending to be bound by theory, it is believed that as the average degree of hydrolysis across the transverse cross-section of the fiber increases, the absorbance capacity of the fiber decreases.

Advantageously, as the degree of hydrolysis of the polymer at the surface region of a fiber increases, relative to the degree of hydrolysis of the polymer in the inner region of the fiber, the bulk solubility of the fiber decreases, allowing for more precise tuning of the solubility parameters of the fibers and different solubility characteristics of the fibers, relative to merely selecting a fiber having a consistent degree of hydrolysis throughout the fiber.

The disclosure further provides a method of treating a fiber comprising a hydrolyzable polymer, comprising contacting a surface of a fiber comprising a hydrolyzable polymer such as a polymer comprising at least one of a vinyl acetate moiety or a vinyl alcohol moiety as described herein (e.g., a polyvinyl alcohol copolymer or a modified copolymer) having a degree of hydrolysis less than 100% with a hydrolysis agent solution to increase the degree of hydrolysis of the hydrolyzable polymer in a region of the fiber comprising at least the surface of the fiber. In embodiments, the contacting can be by immersion, spraying, transfer coating, wicking, foaming, brushing, rolling, humidification, vapor deposition, printing, or a combination thereof. The hydrolyzable polymer can be any hydrolyzable polymer disclosed herein. In embodiments, the hydrolyzable polymer comprises a polymer comprising at least one of a vinyl acetate moiety or a vinyl alcohol moiety, which can be selected from the group consisting of a polyvinyl acetate homopolymer, a polyvinyl alcohol copolymer, a modified polyvinyl alcohol copolymer, or a combination thereof. The hydrolysis agent solution can include any hydrolysis agent disclosed herein and any solvent disclosed herein. In embodiments, the method can further comprise contacting the surface of the fiber with the hydrolysis agent solution after formation of the fiber as part of a continuous inline process. For example, the fiber can be formed from a polymer mixture at a first station and then transferred to a second station where the surface of the fibers can be treated. In another example, the fiber can treated on an apparatus including a polyvinyl alcohol fiber supply station, a polyvinyl alcohol fiber treating station, and a polyvinyl alcohol fiber collection station. In embodiments, the fiber is in motion during the contacting of the surface of the fibers. In embodiments, the contacting the surface of the fiber with the hydrolysis agent solution is performed in a batch by batch process. For example, the fibers can be prepared in bulk and can be treated with the hydrolysis agent prior to formation of the fibers into nonwoven webs. In embodiments, the fiber comprises staple fiber, staple yarn, fiber fill, needle punch fabrics, bonding fibers, or a combination thereof. In embodiments, the fiber comprises staple fiber. In embodiments, the method further comprises washing and drying the fiber after contacting the surface of the fiber with the hydrolysis agent solution. The washing can be by rinsing the fiber with a non-solvent. The drying the fiber can be by air jet drying, agitating, vortexing, or centrifuging.

Although the methods disclosed herein describe treating a fiber such that the degree of hydrolysis of at least a portion of the polymer that makes up the fiber is increased, it will be understood that the fibers can be treated such that the degree of hydrolysis of at least a portion of the polymer that makes up the fiber is decreased. Thus, the disclosure further provides methods of acylation at least a portion of a polyvinyl alcohol polymer comprising admixing a fiber comprising a polyvinyl alcohol polymer with an acylation agent solution to decrease the degree of hydrolysis of at least a portion of the polyvinyl alcohol polymer in the fiber.

The admixing conditions can be any of the conditions described herein for admixing the fiber with the hydrolysis agent solution. Instead of a hydrolysis agent, the acylation agent solution will include an acylation agent. The admixing conditions can be selected to provide a predetermined degree of hydrolysis or predetermined degree of hydrolysis decrease as described herein for the methods for increasing the degree of hydrolysis. Fibers treated with the acylation agent solution can have a transverse cross-section characterized by a core-sheath structure, wherein the polymer of the sheath has a smaller degree of hydrolysis than the polymer of the core, a transverse cross-section characterized by a decreasing gradient in the degree of hydrolysis of the polymer from an interior region to a surface region, or a transverse cross-section characterized by the polymer having the same degree of hydrolysis across the cross-section.

The acylation agent can be any agent that when contacted with a polymer having a pendant hydroxyl (—OH) or amine (—NR$_2$) converts a hydrogen of the pendant hydroxyl or amine to an acyl group (R—C(O)—). Suitable acylation agents include, but are not limited to aldehydes, acyl anhydrides, acyl chlorides, and acyl-coenzymes. In embodiments, the acylation agent comprises an aldehyde in the presence of an acid catalyst such as hydrochloric acid. In embodiments, the acylation agent comprises acetic anhydride and/or acetyl chloride, optionally in the presence of a tertiary or aromatic amine base. In embodiments the acylation agent comprises acetyl coenzyme A (acetyl-CoA) in the presence of the enzyme acetyltransferases.

The disclosure provides a fiber treated according to the methods of the disclosure.

The disclosure provides a fiber having a surface region and an interior region, the fiber comprising a hydrolyzable polymer, the fiber having a transverse cross-section characterized by the hydrolyzable polymer of the surface region having a greater degree of hydrolysis than the hydrolyzable polymer of the interior region. In embodiments, the disclosure provides a fiber having a surface region and an interior region, the fiber comprising a polymer comprising at least one of a vinyl acetate moiety or a vinyl alcohol moiety, the fiber having a transverse cross-section characterized by the polymer of the surface region having a greater degree of hydrolysis than the polymer of the interior region.

The fiber of the disclosure can have a transverse cross-section of the fiber characterized by an increasing gradient in the degree of hydrolysis of the hydrolyzable polymer from the interior region to the surface region. In embodiments, the fiber of the disclosure can have a transverse cross-section of the fiber characterized by an increasing gradient in the degree of hydrolysis of the polymer from the interior region to the surface region.

As shown in FIG. 3, the disclosure provides a fiber comprising a transverse cross-section characterized by a core-sheath structure, the fiber comprising a first, core region (denoted 401 in FIG. 3), comprising a hydrolyzable polymer having a degree of hydrolysis less than 100%, and a second, sheath region (denoted 402 in FIG. 3), comprising a hydrolyzable polymer having a degree of hydrolysis greater than the hydrolyzable polymer of the first region. In embodiments, the fiber can comprise a transverse cross-section characterized by a core-sheath structure, the fiber comprising a first, core region, comprising a polyvinyl alcohol polymer having a degree of hydrolysis less than 100%, and a second, sheath region, comprising a polymer having a degree of hydrolysis greater than the polymer of the first region. In embodiments, the fiber further comprises a third, intermediate region (denoted 403 in FIG. 3), disposed between the first and second regions and comprising a hydrolyzable polymer having a degree of hydrolysis greater than the hydrolyzable polymer of the first region and less than the hydrolyzable polymer of the second region. In embodiments, the hydrolyzable polymer of the first, second, and third regions can comprise a polyvinyl alcohol polymer. In embodiments, the fiber can comprise a plurality of third, intermediate regions (denoted 403A, 403B in FIG. 3), disposed between the first and second regions, the transverse cross-section of the fiber characterized by an increasing gradient in the degree of hydrolysis of the hydrolyzable polymer from the first region to the second region. In embodiments, the plurality of third, intermediate regions, can include a polyvinyl alcohol polymer, the transverse cross-section of the fiber characterized by an increasing gradient in the degree of hydrolysis of the polymer from the first region to the second region.

In embodiments, the fibers of the disclosure can have a difference in the degree of hydrolysis of the polymers in the first and second regions of about 1%, about 2%, about 3%, about 5%, about 7%, about 10%, about 11%, about 12%, about 15%, about 18%, about 20%, about 23%, about 25%, about 27%, or about 29%, for example, in a range of 1% to 29%, about 1% to about 25%, about 1% to about 20%, about 2% to about 18%, about 2% to about 15%, about 3% to about 12%, or about 3% to about 11%. In embodiments, the transverse cross-section of the fiber can be characterized by a mean radius and the second region can comprise about 0.5% of the mean radius of the fiber, for example, about 1%, about 2%, about 3%, about 5%, about 7%, about 9%, about 10%, about 12%, about 15%, about 20%, about 25%, about 50%, about 75%, about 80%, about 85%, about 90%, about 92%, about 94%, about 96%, or about 98%, for example in a range of about 1% to about 98%, about 1% to about 90%, about 1% to about 75%, about 1% to about 50%, about 1% to about 25%, about 1% to about 20% about 1% to about 15%, about 1% to about 12% about 1% to about 10%, about 1% to about 8%, about 1% to about 6%, about 1% to about 5%, about 1% to about 4%, about 2% to about 25%, about 4% to about 25%, about 6% to about 35%, or about 8% to about 20%.

In embodiments, the hydrolyzable polymers in the first, second, and optional third regions have the same degree of polymerization. In embodiments, the hydrolyzable polymers in the first, second, and optional third regions comprise polyvinyl alcohol polymers having the same degree of polymerization. In embodiments, the hydrolyzable polymers in the first, second, and optional third regions comprise modified polyvinyl alcohol polymers having the same degree of modification.

Although the fibers disclosed herein having a transverse cross-section characterized by a core-sheath structure or gradient degree of hydrolysis are described as having a greater degree of hydrolysis in the sheath and/or surface region of the fiber, it will be understood that the fibers can be prepared (i.e., with an acylation agent) such that the degree of hydrolysis in the polymer of the sheath and/or surface region of the fiber is less than the degree of hydrolysis of the polymer of the core and/or inner surface region. Thus, the disclosure further provides a fiber having a surface region and an interior region, the fiber comprising a hydrolyzable polymer, the fiber having a transverse cross-section characterized by the hydrolyzable polymer of the surface region having a lesser degree of hydrolysis than the hydrolyzable polymer of the interior region. In embodiments, the disclosure provides a fiber having a surface region and an interior region, the fiber comprising a polyvinyl alcohol polymer, the fiber having a transverse cross-section characterized by the polyvinyl alcohol polymer of the surface region having a lesser degree of hydrolysis than the polyvinyl alcohol polymer of the interior region.

The fiber of the disclosure can have a transverse cross-section of the fiber characterized by a decreasing gradient in the degree of hydrolysis of the hydrolyzable polymer from the interior region to the surface region. In embodiments, the fiber of the disclosure can have a transverse cross-section of the fiber characterized by a decreasing gradient in the degree of hydrolysis of the polymer from the interior region to the surface region.

In the fiber having a surface region and an interior region provided in the present disclosure, the polymer in the interior region has a first degree of hydrolysis and the polymer in the surface region has a second degree of hydrolysis greater than the first degree of hydrolysis. In some embodiments, the first degree of hydrolysis is in a range of from about 79% to about 96% and the second degree of hydrolysis is in a range of from about 88% to 100%, for example, from about 90% to 100%, from about 88% to 99%, or from about 90% to about 99%. In some embodiments, the first degree of hydrolysis is in a range of from about 79% to about 92% and the second degree of hydrolysis is in a range of from about 88% to about 96%.

The fiber has a dissolution time of less than 200 seconds in water at 23° C. The fiber has a shrinkage along a longitudinal axis of the fiber in a range of from 20% to 70% while contacting water at a temperature in a range of from 10° C. to 23° C. In embodiments, the polymer in the interior region has a glass transition temperature ($T_g$) in a range of from about 72° C. to about 72.9° C. and the polymer in the surface region has a $T_g$ in a range of from about 73° C. to about 85° C.

In some embodiments, the fiber provided in the present disclosure has a longitudinal axis and a transverse cross-section perpendicular to the longitudinal axis of the fiber. The fiber further has a core and sheath structure along at least a portion of the longitudinal axis. The fiber comprises a core region of the core and sheath structure comprising a polymer comprising at least one of a vinyl acetate moiety or a vinyl alcohol moiety having a first degree of hydrolysis less than 100%.

The fiber has a sheath region of the core and sheath structure disposed radially outward from the core region in the transverse cross-section. The sheath region comprises the polymer comprising at least one of a vinyl acetate moiety or a vinyl alcohol moiety having a second degree of hydrolysis greater than the first degree of hydrolysis. As described herein, in embodiments, the polymer comprising at least one of a vinyl acetate moiety or a vinyl alcohol moiety comprises a polyvinyl alcohol homopolymer, a polyvinyl acetate homopolymer, a vinyl acetate and vinyl alcohol copolymer, a modified polyvinyl alcohol copolymer, or combinations thereof. A difference between the first degree of hydrolysis and the second degree of hydrolysis is at least 1%. The difference between the first degree of hydrolysis and the second degree of hydrolysis may be in a range of 1% to 29%. The first and the second degrees of hydrolysis may be within the ranges as described above. For example, with the sheath region having a second degree of hydrolysis in a range of from about 88% to about 96%, the fiber has a dissolution time of less than 200 seconds in water at 23° C., the fiber has a drying shrinkage in a range of from about 20% to about 70% after soaking in water at a temperature in a range of from 10° C. to 23° C., and the polymer in the sheath region has a glass transition temperature in a range of from about 73° C. to about 85° C. The core and sheath (or shell) structure may include at least one intermediate layer as described above.

The present disclosure also provides a fiber comprising a first region and a second region. The first region comprises a polymer comprising at least one of a vinyl acetate moiety or a vinyl alcohol moiety having a first degree of hydrolysis less than 100%. The second region comprises the polymer comprising at least one of a vinyl acetate moiety or a vinyl alcohol moiety having a second degree of hydrolysis greater than the first degree of hydrolysis. In embodiments, such a polymer comprises a polyvinyl alcohol homopolymer, a polyvinyl acetate homopolymer, a vinyl acetate and vinyl alcohol copolymer, a modified polyvinyl alcohol copolymer, or a combination thereof. The fiber has a longitudinal axis. The first region forms a core region of the fiber along the longitudinal axis and the second region forms a sheath region of the fiber surrounding at least a portion of the core region. The fiber has a transverse cross-section perpendicular to the longitudinal axis.

The fiber may further comprise an intermediate region disposed between the first region and the second region in the transverse cross-section. The intermediate region comprises the polymer having a third degree of hydrolysis greater than the first degree of hydrolysis and less than the second degree of hydrolysis. The fiber has a transverse cross-section perpendicular to the longitudinal axis. The fiber may further comprise a plurality of intermediate regions comprising the polymer and disposed between the first region and the second region, and the transverse cross-section has an increasing gradient in a degree of hydrolysis from the first region to the second region. As described above, the difference between the first degree of hydrolysis and the second degree of hydrolysis is at least 1%; for example, in a range of from 1% to 29%. The polymer in each of the first region, the second region, and the third region may have a same degree of polymerization, for example, the polymer comprises a modified polyvinyl alcohol polymer having a same degree of modification.

Nonwoven Webs

Figure 7:
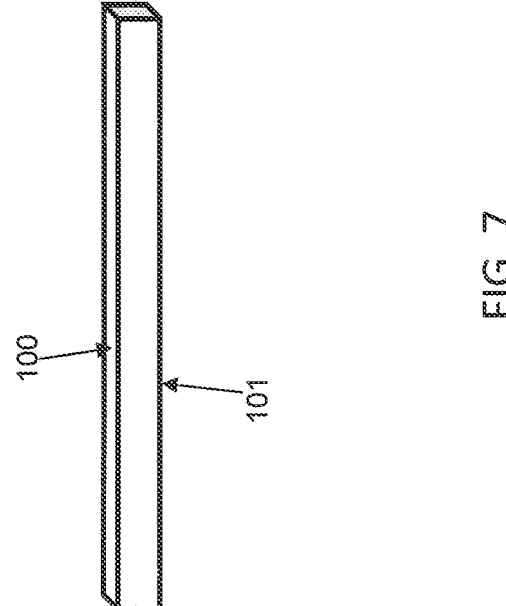
FIG. 7 shows a nonwoven web noting the exterior surfaces of the web as 100 and 101.

The nonwoven webs of the disclosure are generally sheet-like structures having two exterior surfaces, the nonwoven webs including a plurality of fibers. As used herein, and unless specified otherwise, the "exterior surface" of a nonwoven web refers to the faces of the sheet-like structure, denoted 100 and 101 in FIG. 7. A nonwoven web generally refers to an arrangement of fibers bonded to one another, wherein the fibers are neither woven nor knitted. In general, the plurality of fibers can be arranged in any orientation. In embodiments, the plurality of fibers are arranged randomly (i.e., do not have an orientation). In embodiments, the plurality of fibers are arranged in a unidirectional orientation. In embodiments, the plurality of fibers are arranged in a bidirectional orientation. In some embodiments, the plurality of fibers are multi-directional, having different arrangements in different areas of the nonwoven web. In embodiments, the nonwoven web can include a single type of water-soluble fiber. In embodiments, the nonwoven web can include a single type of water-insoluble fiber. In embodiments, the nonwoven web can include a single type of water-soluble fiber and one or more different types of water-insoluble fibers. In embodiments, the nonwoven web can include one or more different types of water-soluble fibers and one or more different types of water-insoluble fibers. In embodiments, the nonwoven web can consist of or consist essentially of water-soluble fibers. In embodiments, the nonwoven web can consist of or consist essentially of water-insoluble fibers. In some embodiments, the nonwoven web can include a single type of fiber forming material (i.e., all fibers have the same composition of fiber forming material), but can include fibers prepared by one or more fiber forming processes, e.g., wet cooled gel spinning, thermoplastic fiber spinning, melt blowing, spun bonding, or a combination thereof. In some embodiments, the nonwoven web can include a single type of fiber forming material and the fibers are made from a single fiber forming process. In some embodiments, the nonwoven web can include two or more fiber forming materials (e.g., blends of fibers having different compositions of fiber forming materials, fibers including blends of fiber forming materials, or both) and the fibers can be prepared by one or more fiber forming processes, e.g., wet-cool gel spinning, thermoplastic fiber spinning, melt blowing, spun bonding, or a combination thereof. In some embodiments, the nonwoven web can include two or more fiber forming materials and the fibers are made from a single fiber forming process. In embodiments, the fibers of the nonwoven web can have substantially the same diameters or different diameters.

In embodiments wherein the nonwoven webs of the disclosure include a blend of fibers including a first fiber and a second fiber, the first and second fibers can have a difference in length to diameter (L/D ratio, tenacity, shape, rigidity, elasticity, solubility, melting point, glass transition temperature ($T_g$), fiber forming material, color, or a combination thereof.

As is well understood in the art, the term machine-direction (MD) refers to the direction of web travel as the nonwoven web is produced, for example on commercial nonwoven making equipment. Likewise, the term cross-direction (CD) refers to the direction in the plane of the web perpendicular to the machine-direction. With respect to nonwoven composite articles, wipes, absorbent articles or other article comprising a nonwoven composite article of the disclosure, the terms refer to the corresponding directions of the article with respect to the nonwoven web used to produce the article.

The tenacity of the nonwoven web can be the same or different from the tenacity of the fibers used to prepare the web. Without intending to be bound by theory, it is believed that the tenacity of the nonwoven web is related to the strength of the nonwoven web, wherein a higher tenacity provides a higher strength to the nonwoven web. In general, the tenacity of the nonwoven web can be modified by using fibers having different tenacities. The tenacity of the nonwoven web may also be affected by processing. In general, water-dispersible webs of the disclosure can have relatively high tenacities, i.e., the water-dispersible nonwoven web is a self-supporting web that can be used as the sole material for preparing an article and/or pouch. In embodiments, the nonwoven web is a self-supporting web. In contrast, the nonwoven webs that are prepared according to melt blowing, electro-spinning, and/or rotary spinning processes typically have low tenacities, and may not be self-supporting or capable of being used as a sole web for forming an article or pouch. Thus, in some embodiments, the nonwoven web is not self-supporting and is used in combination with a second nonwoven web and/or water-soluble film.

In embodiments, the nonwoven webs of the disclosure can have a ratio of tenacity in the machine direction to the tenacity in the cross direction (MD:CD) of in a range of about 0.5 to about 1.5, about 0.75 to about 1.5, about 0.80 to about 1.25, about 0.90 to about 1.1, or about 0.95 to about 1.05, or about 1. In embodiments, the nonwoven webs of the disclosure have a tenacity ratio MD:CD of about 0.8 to about 1.25. In embodiments the nonwoven webs of the disclosure have a tenacity ratio MD:CD of about 0.9 to about 1.1. In embodiments, the nonwoven webs of the disclosure have a tenacity of about 1. Without intending to be bound by theory, it is believed that as the tenacity ratio MD:CD approaches 1, the durability of the nonwoven is increased, providing superior resistance to breakdown of the nonwoven when stress is applied to the nonwoven during use, e.g., scrubbing with a flushable wipe comprising a nonwoven web of the disclosure, or pulling/tugging on the nonwoven caused by movement while wearing a wearable absorbent article.

The nonwoven webs of the disclosure can have a rougher surface relative to a water-soluble film, which provides decreased contact between a surface and the nonwoven web than between a surface and the water-soluble film. Advantageously, this surface roughness can provide an improved feel to the consumer (i.e., a cloth-like hand-feel instead of a rubbery hand-feel), improved aesthetics (i.e., less glossy than a water-soluble film), and/or facilitate processability in preparing thermoformed, and/or vertical formed, filled, and sealed, and/or multichamber packets which require drawing the web along a surface of the processing equipment/mold. Accordingly, the fibers should be sufficiently coarse to provide a surface roughness to the resulting nonwoven web without being so coarse as to produce drag.

Nonwoven webs can be characterized by basis weight. The basis weight of a nonwoven is the mass per unit area of the nonwoven. Basis weight can be modified by varying manufacturing conditions, as is known in the art. A nonwoven web can have the same basis weight prior to and subsequent to bonding. Alternatively, the bonding method can change the basis weight of the nonwoven web. For example, wherein bonding occurs through the application of heat and pressure, the thickness of the nonwoven (and, thus, the area of the nonwoven) can be decreased, thereby increasing the basis weight. Accordingly, as used herein and unless specified otherwise, the basis weight of a nonwoven refers to the basis weight of the nonwoven subsequent to bonding.

The nonwoven webs of the disclosure can have any basis weight in a range of about 0.1 $g/m^2$ to about 700 $g/m^2$, about 0.5 $g/m^2$ to about 600 $g/m^2$, about 1 $g/m^2$ to about 500 $g/m^2$, about 1 $g/m^2$ to about 400 $g/m^2$, about 1 $g/m^2$ to about 300 $g/m^2$, about 1 $g/m^2$ to about 200 $g/m^2$, about 1 $g/m^2$ to about 100 $g/m^2$, about 30 $g/m^2$ to about 100 $g/m^2$, about 20 $g/m^2$ to about 100 $g/m^2$, about 20 $g/m^2$ to about 80 $g/m^2$, or about 25 $g/m^2$ to about 70 $g/m^2$.

In embodiments, the nonwoven web can be carded and have a basis weight of about 5 $g/m^2$ to about 15 $g/m^2$, about 7 $g/m^2$ to about 13 $g/m^2$, about 9 $g/m^2$ to about 11 $g/m^2$, or about 10 $g/m^2$. In embodiments, the nonwoven web can be carded and can have a basis weight of 30 $g/m^2$ or more, for example in a range of 30 $g/m^2$ to about 70 $g/m^2$, about 30 $g/m^2$ to about 60 $g/m^2$, about 30 $g/m^2$ to about 50 $g/m^2$, about 30 $g/m^2$ to about 40 $g/m^2$, or about 30 $g/m^2$ to about 35 $g/m^2$. In embodiments, the nonwoven web can be melt-spun and have a basis weight in a range of about 1 $g/m^2$ to about 20 $g/m^2$, about 2 $g/m^2$ to about 15 $g/m^2$, about 3 $g/m^2$ to about 10 $g/m^2$, about 5 $g/m^2$ to about 15 $g/m^2$, about 7 $g/m^2$ to about 13 $g/m^2$, about 9 $g/m^2$ to about 11 $g/m^2$, or about 10 $g/m^2$. In embodiments, the nonwoven web can be melt-spun and can have a basis weight of about 0.1 $g/m^2$ to about 10 $g/m^2$, about 0.1 $g/m^2$ to about 8 $g/m^2$, about 0.2 $g/m^2$ to about 6 $g/m^2$, about 0.3 $g/m^2$ to about 4 $g/m^2$, about 0.4 $g/m^2$ to about 2 $g/m^2$, or about 0.5 $g/m^2$ to about 1 $g/m^2$.

Related to the basis weight is the fiber volume density and porosity of a nonwoven. Nonwoven webs, as prepared and prior to bonding, generally have a fiber density of about 30% or less by volume, i.e., for a given volume of nonwoven, 30% or less of the volume is made up of the fibers and the remaining volume is air. Thus, the nonwoven webs are generally highly porous. Fiber volume density and porosity of the nonwoven are inversely related characteristics of a nonwoven, for example, a nonwoven having a fiber volume density of about 30% by volume would have a porosity of about 70% by volume. It is well understood in the art that as the fiber volume density increases, the porosity decreases. Fiber volume density can be increased by increasing the basis weight of a nonwoven, for example, by bonding through the application of heat and pressure, potentially reducing the thickness (and, thus, the volume) of the nonwoven. Accordingly, as used herein and unless specified otherwise, the fiber volume density and porosity of a nonwoven refers to the fiber volume density and porosity of the nonwoven subsequent to bonding.

The nonwoven webs of the disclosure can have any porosity in a range of about 50% to about 95%, for example, at least about 50%, at least about 60%, at least about 70%, at least about 75%, or at least about 80% and up to about 95%, up to about 90%, up to about 85%, up to about 80%, up to about 75%, up to about 70%, or in a range of about 50% to about 95%, about 50% to about 80%, about 50% to about 70%, about 60% to about 75%, about 60% to about 80%, about 60% to about 90%, about 75% to about 85%, about 75% to about 90%, or about 75% to about 95%.

Pore sizes can be determined using high magnification and ordered surface analysis techniques including, but not limited to Brunauer-Emmett-Teller theory (BET), small angle X-ray scattering (SAXS), and molecular adsorption.

The nonwoven webs of the disclosure can have any thickness. Suitable thicknesses can include, but are not limited to, about 5 to about 10,000 μm (1 cm), about 5 to about 5,000 μm, about 5 to about 1,000 μm, about 5 to about 500 μm, about 200 to about 500 μm, about 5 to about 200 μm, about 20 to about 100 μm, or about 40 to about 90 μm, or about 50 to 80 μm, or about or about 60 to 65 μm for example 50 μm, 65 μm, 76 μm, or 88 μm. The nonwoven webs of the disclosure can be characterized as high loft or low loft. In general, loft refers to the ratio of thickness to basis weight. High loft nonwoven webs can be characterized by a high ratio of thickness to basis weight. As used herein, "high loft" refers to a nonwoven web of the disclosure having a basis weight as defined herein and a thickness exceeding 200 μm. The thickness of the nonwoven web can be determined by according to ASTM D5729-97, ASTM 05736, and ISO 9073-2:1995 and can include, for example, subjecting the nonwoven web to a load of 2 N and measuring the thickness. High loft materials can be used according to known methods in the art, for example, thru-air bonding or cross-lapping, which uses a cross-lapper to fold the unbounded web over onto itself to build loft and basis weight. Without intending to be bound by theory, in contrast to water-soluble films wherein the solubility of the film can be dependent on the thickness of the film; the solubility of a nonwoven web including water-soluble fibers is not believed to be dependent on the thickness of the web. In this regard, it is believed that because the individual fibers provide a higher surface area than a water soluble film, regardless of the thickness of the film, the parameter that limits approach of water to the fibers and, thereby, dissolution of the fibers in a water-soluble nonwoven web is the basis weight.

The water-solubility of the nonwoven webs of the disclosure is generally a function of the type of fiber(s) used to prepare the web as well as the basis weight of the water-dispersible web. Without intending to be bound by theory, for a nonwoven web comprising a sole fiber type comprising a sole fiber forming material, it is believed that the solubility profile of a nonwoven web follows the same solubility profile of the fiber(s) used to prepare the nonwoven web, and the solubility profile of the fiber generally follows the same solubility profile of the fiber forming polymer(s) from which the fiber is prepared. For example, for nonwoven webs comprising PVOH fibers, the degree of hydrolysis of the polymer can be chosen such that the water-solubility of the nonwoven web is also influenced. In general, at a given temperature, as the degree of hydrolysis of the polymer increases from partially hydrolyzed (88% DH) to fully hydrolyzed (≥98% DH), water solubility of the polymer generally decreases. Thus, in one option, the nonwoven web can be cold water-soluble. For a co-poly(vinyl acetate vinyl alcohol) polymer that does not include any other monomers (e.g., not copolymerized with an anionic monomer) a cold water-soluble web, soluble in water at a temperature of less than 10° C., can include fibers of the PVOH copolymer with a degree of hydrolysis in a range of about 75% to about 90%, or in a range of about 80% to about 90%, or in a range of about 85% to about 90%. In another option the nonwoven web can be hot water-soluble. For a co-poly(vinyl acetate vinyl alcohol) polymer that does not include any other monomers (e.g., not copolymerized with an anionic monomer) a hot water-soluble web, soluble in water at a temperature of at least about 60° C., can include fibers of the PVOH copolymer with a degree of hydrolysis of at least about 98%.

Modification of the PVOH copolymer increases the solubility of the PVOH copolymer. Thus, it is expected that at a given temperature the solubility of a water-dispersible nonwoven web prepared from a modified PVOH copolymer, would be higher than that of a nonwoven web prepared from a PVOH copolymer without modification having the same degree of hydrolysis as the PVOH copolymer. Following these trends, a water-dispersible nonwoven web having specific solubility characteristics can be designed.

Surprisingly, for a nonwoven web including a blend of fiber types, each fiber type having a sole fiber forming material, the solubility of the nonwoven web does not follow the rule of mixtures as would be expected for a blend of fiber types. Rather, for a nonwoven web including blend of two fiber types, when the two fiber types were provided in a ratio other than 1:1, the solubility of the nonwoven tended toward the solubility of the less soluble fiber (i.e., the fiber that requires higher temperatures to completely dissolve, and dissolves more slowly at temperatures below the complete dissolution temperature). For nonwoven webs including 1:1 blends of fibers, the solubility of the nonwoven web was generally lower than the solubility of the nonwoven webs including blends other than 1:1 blends (i.e., at a given temperature, the nonwoven webs including the 1:1 blends took longer to rupture, disintegrate, and dissolve than the nonwoven webs including, e.g., 3:1 and 1:3 ratios of fiber types). This trend was especially pronounced at temperatures lower than the complete dissolution tempera of the less soluble fiber.

Inclusion of a water-insoluble fiber in a nonwoven web can also be used to design a nonwoven web having specific solubility and/or delayed release properties (e.g., when the nonwoven web is included in a water-dispersible pouch). Without intending to be bound by theory, it is believed that as the weight percent of water-insoluble fiber included in a nonwoven web is increased (based on the total weight of the nonwoven web), the solubility of the nonwoven web generally decreases and the delayed release properties of a pouch comprising a nonwoven web generally increase. Upon contact with water at a temperature at or above the solubility temperature of the water-soluble fiber, a nonwoven web comprising a water-soluble fiber and water-insoluble fiber will begin to thin as the water-soluble fiber dissolves, thereby breaking down the web structure and/or increasing the pore size of the pores of the nonwoven web. In general, the larger the break-down of the web structure or increase in the pore size, the faster the water can access the contents of the pouch and the faster the contents of the pouch will be released. Similarly, delayed release of the contents of a pouch comprising the nonwoven web of the disclosure can be achieved by using a blend of water-soluble fibers having different solubility properties and/or different solubility temperatures. In general, for nonwoven webs including water-soluble fibers comprising a polyvinyl alcohol fiber forming materials, at water temperatures of 50% or more of the complete dissolution temperature of the water-soluble fibers (e.g., at 40° C. for a fiber having a complete dissolution temperature of 70° C.), the fibers will undergo polymer network swelling and softening, but the overall structure will remain intact. In embodiments wherein the nonwoven web includes a water-soluble fiber and a water-insoluble fiber, the ratio of soluble fiber to insoluble fiber is not particularly limited. The water-soluble fiber can comprise about 1% to about 99%, about 20% to about 80%, about 40% to about 90%, about 50% to about 90%, or about 60% to about 90% by weight of the total weight of the fibers and the water-insoluble fiber can comprise about 1% to about 99%, about 20% to about 80%, about 10% to about 60%, about 10% to about 50%, or about 10% to about 40% by weight of the total weight of the fibers.

Further, as the basis weight of the nonwoven web increases the rate of dissolution of the web decreases, provided the fiber composition and bonding parameters remain constant, as there is more material to be dissolved. For example, at a given temperature, a water-soluble web prepared from fibers comprising PVOH polymer(s) and having a basis weight of, e.g., 40 $g/m^2$, is expected to dissolve slower than an otherwise-identical nonwoven web having a basis weight of, e.g., 30 $g/m^2$. This relationship was especially prominent when the temperature of the water for dissolution was lower than the complete dissolution temperature of the fibers that made up the nonwoven web. Accordingly, basis weight can also be used to modify the solubility characteristics of the water-dispersible nonwoven web. The nonwoven web can have any basis weight in a range of about 1 g/m$^2$ to about 700 g/m$^2$, about 1 g/m$^2$ to about 600 g/m$^2$, about 1 g/m$^2$ to about 500 g/m$^2$, about 1 g/m$^2$ to about 400 g/m$^2$, about 1 g/m$^2$ to about 300 g/m$^2$, about 1 g/m$^2$ to about 200 g/m$^2$, about 1 g/m$^2$ to about 100 g/m$^2$, about 30 g/m$^2$ to about 100 g/m$^2$, about 20 g/m$^2$ to about 100 g/m$^2$, about 20 g/m$^2$ to about 80 g/m$^2$, about 25 g/m$^2$ to about 70 g/m$^2$, or about 30 g/m$^2$ to about 70 g/m$^2$.

Additionally, calendar settings have a secondary impact on the solubility profile of a nonwoven web of the disclosure. For example, for nonwoven webs having identical fiber chemistry and similar basis weights, at a given calendar pressure, the solubility time of a nonwoven web generally increases with increasing calendar temperature. This relationship was especially prominent when the temperature of the water for dissolution was lower than the complete dissolution temperature of the fibers that made up the nonwoven web.

Without intending to be bound by theory, it is believed that solubility (in terms of time to dissolution, for example according to MSTM-205) of a water-soluble nonwoven web is expected to surpass that of a water-soluble film of the same size (L×W) and/or mass, prepared from the same PVOH polymer. This is due to the higher surface area found in the nonwoven compared to a film, leading to faster solubilization.

The nonwoven web of the disclosure can include any of the auxiliary agents disclosed herein. Auxiliary agents can be dispersed throughout the web, e.g., between fibers, or applied to one of more surfaces of the nonwoven web. Auxiliary agents can be added to the nonwoven web during the melt-spun process, using a "co-form" process developed by Kimberly Clark, as is well known in the art. Auxiliary agents can also be added to one or more faces of a nonwoven web or article prepared therefrom, by any suitable means.

In embodiments, the nonwoven webs of the disclosure are substantially free of auxiliary agents. As used herein and unless specified otherwise, "substantially free of auxiliary agents" means that the nonwoven web includes less than about 0.01 wt. %, less than about 0.005 wt. %, or less than about 0.001 wt. % of auxiliary agents, based on the total weight of the nonwoven web.

In a one embodiment, one or more stationary powder spray guns are used to direct an auxiliary agent powder stream towards the web or article, from one or more than one direction, while the web or article is transported through the coating zone by means of a belt conveyor. In an alternative embodiment, an article is conveyed through a suspension of an auxiliary agent powder in air. In yet another alternative embodiment the articles are tumble-mixed with the auxiliary agent powder in a trough-like apparatus. In another embodiment, which can be combined with any other embodiment, electrostatic forces are employed to enhance the attraction between the auxiliary agent powder and the article. This type of process is typically based on negatively charging the powder particles and directing these charged particles to the grounded articles. In other alternative embodiments, the auxiliary agent powder is applied to the article by a secondary transferring tool including, but not limited to rotating brushes which are in contact with the powder or by powdered gloves which can transfer the powder from a container to the article. In yet another embodiment the auxiliary agent powder is applied by dissolving or suspending the powder in a non-aqueous solvent or carrier which is then atomized and sprayed onto the nonwoven or article. In one type of embodiment, the solvent or carrier subsequently evaporates, leaving the auxiliary agent powder behind. In one class of embodiments, the auxiliary agent powder is applied to the nonwoven or article in an accurate dose. This class of embodiments utilizes closed-system dry lubricant application machinery, such as PekuTECH's powder applicator PM 700 D. In this process the auxiliary agent powder, optionally batch-wise or continuously, is fed to a feed trough of application machinery. The nonwoven webs or articles are transferred from the output belt of a standard rotary drum pouch machine onto a conveyor belt of the powder application machine, wherein a controlled dosage of the auxiliary agent is applied to the nonwoven web or article.

Liquid auxiliary agents can be applied to a nonwoven web or article, for example, by spin casting, spraying a solution such as an aerosolized solution, roll coating, flow coating, curtain coating, extrusion, knife coating, and combinations thereof.

In embodiments, the nonwoven web can be colored, pigmented, and/or dyed to provide an improved aesthetic effect relative to water-soluble films. Suitable colorants can include an indicator dye, such as a pH indicator (e.g., thymol blue, bromothymol, thymolphthalein, and thymolphthalein), a moisture/water indicator (e.g., hydrochromic inks or leuco dyes), or a thermochromic ink, wherein the ink changes color when temperature increases and/or decreases. Suitable colorants include, but are not limited to a triphenylmethane dye, an azo dye, an anthraquinone dye, a perylene dye, an indigoid dye, a food, drug and cosmetic (FD&C) colorant, an organic pigment, an inorganic pigment, or a combination thereof. Examples of colorants include, but are not limited to, FD&C Red #40; Red #3; FD&C Black #3; Black #2; Mica-based pearlescent pigment; FD&C Yellow #6; Green #3; Blue #1; Blue #2; titanium dioxide (food grade); brilliant black; and a combination thereof.

When included in a water-soluble fiber, the colorant can be provided in an amount of 0.01% to 25% by weight of the water-soluble polymer mixture, such as, 0.02%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, and 24% by weight of the water-soluble polymer mixture.

Advantageously, the nonwoven webs of the disclosure can demonstrate preferential shrinking in the presence of heat and/or water (e.g., humidity). Accordingly, the nonwoven webs can be heat and/or water shrunk when formed into packets. Further advantageously, the nonwoven webs of the disclosure can demonstrate increased robustness (i.e., mechanical properties) and improved solubility performance after storage in high heat and moisture environments (e.g., 38° C. and 80% relative humidity (RH)). Such increased robustness and improved solubility performance is surprising as the expectation based on compositionally similar water-soluble films is that the robustness and solubility performance would be unaffected by storage in high heat and moisture conditions. In particular, after removal of comparable water-soluble films from a conditioning environment, the water-soluble films will re-equilibrate with the surrounding environment leading to no long term or permanent changes in the performance properties of the films.

The nonwoven web of the disclosure can be used as a single layer or can be layered with other nonwoven webs and/or water-soluble films. In some embodiments, the nonwoven web includes a single layer of nonwoven web. In some embodiments, the nonwoven web is a multilayer nonwoven web comprising two or more layers of nonwoven webs. The one or more layers can be laminated to each other. In refinements of the foregoing embodiment, the two or more layers can be the same (e.g., be prepared from the same fibers and having the same basis weight). In refinements of the foregoing embodiment, the two or more layers can be different (e.g., be prepared from different types of fibers and/or have different basis weights). In embodiments, the nonwoven web can be laminated to a water-soluble film. In refinements of the foregoing embodiments, the nonwoven web and water-soluble film can be prepared from the same polymer (e.g., a PVOH copolymer or a modified copolymer having a specific viscosity, degree of hydrolysis, and amount of modification if a modified polymer). In refinements of the foregoing embodiments, the nonwoven web and water-soluble film can be prepared from different polymers (e.g., the polymer used to prepare the fibers of the nonwoven web can have different fiber chemistries (e.g., modifications), viscosities, degree of polymerization, degree of hydrolysis and/or solubility than the polymer that makes up the water-soluble film). Advantageously, multilayered nonwoven webs and laminates can be used to tune the moisture vapor transmission rate (MVTR) of a pouch or packet made therefrom. Multilayer materials can be prepared according to various processes known in the art, for example, melt extrusion, coating (e.g., solvent coating, aqueous coating, or solids coating), spray adhesion, material transfer, hot lamination, cold lamination, and combinations thereof.

A multilayer nonwoven web can have a basis weight that is the sum of the basis weights of the individual layers. Accordingly, a multilayer nonwoven web will take longer to dissolve than any of the individual layers provided as a single layer. In embodiments, the multilayer nonwoven can have a basis weight in a range of about 1 $g/m^2$ to about 100 $g/m^2$. Additionally, without intending to be bound by theory, it is believed that when pore sizes and pore arrangements are heterogeneous between layers, the pores in each layer will not align, thereby providing a multilayer nonwoven web having smaller pores than the individual layers. Accordingly, a nonporous water-dispersible nonwoven web can be prepared by layering multiple porous water-dispersible nonwoven webs.

The nonwoven web can also be laminated to a water-soluble film. The laminate can be formed using any known methods in the art including, but not limited to heat and pressure, chemical bonding, and/or solvent welding. Chemical bonding can include ionically or covalently functionalizing a surface of the nonwoven web and/or a surface of the water-soluble film such that when the surface of the nonwoven web comes in contact with the surface of the water-soluble film a chemical reaction occurs and covalently bonds the nonwoven web and water-soluble film together. The multilayer nonwoven web can include three or more layers. In embodiments, the multilayer nonwoven web can include a first layer comprising a water-soluble film, a second layer comprising a nonwoven web, and a third layer comprising a water-soluble film. In embodiments, the multilayer nonwoven web can include a first layer comprising a nonwoven web, a second layer comprising a water-soluble film, and a third layer comprising a nonwoven web.

Advantageously, the laminate can be prepared concurrently with pouch formation, e.g., using the heat applied during thermoforming to bond the nonwoven web and water-soluble film layers together. The water-soluble film can have the same solubility and/or chemical compatibility characteristics as the nonwoven web or the water-soluble film can have different solubility and/or chemical compatibility characteristics from the nonwoven web. In embodiments, the water-soluble film has the same solubility and/or chemical compatibility characteristics as the nonwoven web.

In some embodiments, the water-soluble film has different solubility and/or chemical compatibility characteristics from the nonwoven web. Advantageously, when the water-soluble film has different solubility and/or chemical compatibility characteristics from the nonwoven web the laminate can be used to form a pouch having an interior surface with a first solubility and/or chemical compatibility and an exterior surface having a second solubility and/or chemical compatibility.

The water-soluble film used for a laminate can be any water-soluble film, e.g., one previously known in the art. The polymer used to form the water-soluble film can be any water-soluble polymer, or combination thereof, e.g., one described herein. The water-soluble film can contain at least about 50 wt. %, 55 wt. %, 60 wt. %, 65 wt. %, 70 wt. %, 75 wt. %, 80 wt. %, 85 wt. %, or 90 wt. % and/or up to about 60 wt. %, 70 wt. %, 80 wt. %, 90 wt. %, 95 wt. %, or 99 wt. % of a water-soluble polymer, e.g., a PVOH polymer or polymer blend.

The water-soluble film can contain other auxiliary agents and processing agents, such as, but not limited to, plasticizers, plasticizer compatibilizers, surfactants, lubricants, release agents, fillers, extenders, cross-linking agents, antiblocking agents, antioxidants, detackifying agents, antifoams, nanoparticles such as layered silicate-type nanoclays (e.g., sodium montmorillonite), bleaching agents (e.g., sodium metabisulfite, sodium bisulfite or others), aversive agents such as bitterants (e.g., denatonium salts such as denatonium benzoate, denatonium saccharide, and denatonium chloride; sucrose octaacetate; quinine; flavonoids such as quercetin and naringen; and quassinoids such as quassin and brucine) and pungents (e.g., capsaicin, piperine, allyl isothiocyanate, and resinferatoxin), and other functional ingredients, in amounts suitable for their intended purposes. Embodiments including plasticizers are preferred. The amount of such agents can be up to about 50 wt. %, 20 wt %, 15 wt %, 10 wt %, 5 wt. %, 4 wt % and/or at least 0.01 wt. %, 0.1 wt %, 1 wt %, or 5 wt % of the film, individually or collectively.

The disclosure further provides a method of treating a nonwoven web comprising a plurality of fibers comprising hydrolyzable polymers such as a polymer comprising at least one of a vinyl acetate moiety or a vinyl alcohol moiety and having a degree of hydrolysis less than 100%, the method comprising contacting at least a portion of the nonwoven web with a hydrolysis agent solution as described herein to increase the degree of hydrolysis of the hydrolyzable polymer of the fibers of the portion of the nonwoven web. In embodiments, the portion of the nonwoven web contacted with the hydrolysis agent can be a face of the nonwoven web. In embodiments, the contacting can be by immersion, spraying, transfer coating, wicking, foaming, brushing, rolling, humidification, vapor deposition, printing, or a combination thereof. In embodiments, the contacting occurs concurrently with bonding of the plurality of the fibers into the nonwoven web. In embodiments, the contacting and bonding comprises chemical bonding. In embodiments, the contacting and bonding comprises heat activated catalysis. The hydrolyzable polymer can be any hydrolyzable polymer disclosed herein. In embodiments, the hydrolyzable polymer comprises a polymer comprising at least one of a vinyl acetate moiety or a vinyl alcohol moiety, which can be selected from a polyvinyl acetate homopolymer, a polyvinyl alcohol homopolymer, a polyvinyl alcohol copolymer, a modified polyvinyl alcohol copolymer, and a combination thereof. In embodiments, the polyvinyl alcohol copolymer comprises an anionically modified copolymer. In embodiments, the anionically modified copolymer comprises a carboxylate, a sulfonate, or a combination thereof. In embodiments, the fiber further comprises an additional polymer. The hydrolysis agent solution can comprise any hydrolysis agent disclosed herein and any solvent disclosed herein. In embodiments, the hydrolysis agent comprises a metallic hydroxide, a metal hydride, a sulfite compound, a sulfur dioxide, a dithionate, a thiosulfate, a hydrazine, oxalic acid, formic acid, ascorbic acid, dithiothreitol, a phosphite, a hypophosphite, phosphorous acid, sulfuric acid, sulphonic acid, hydrochloric acid, ammonium hydroxide, water, or a combination thereof. In embodiments, the hydrolysis agent is provided in an amount of about 0.2% to about 75% (w/w) based on the weight of the solvent. In embodiments, the fiber is not soluble in the solvent prior to treatment, during treatment, and after treatment. In embodiments, the hydrolysis agent solution further comprises an activator.

The disclosure further provides a method of treating a nonwoven web comprising a plurality of fibers comprising polymers such as a polymer comprising at least one of a vinyl acetate moiety or a vinyl alcohol moiety and having a degree of hydrolysis of 100% or less and greater than 0%, the method comprising contacting at least a portion of the nonwoven web with an acylation agent solution to decrease the degree of hydrolysis of the polymer of the fibers of the portion of the nonwoven web. In embodiments, the portion of the nonwoven web contacted with the acylation agent can be a face of the nonwoven web. In embodiments, the contacting can be by immersion, spraying, transfer coating, wicking, foaming, brushing, rolling, humidification, vapor deposition, printing, or a combination thereof. In embodiments, the contacting occurs concurrently with bonding of the plurality of the fibers into the nonwoven web. In embodiments, the contacting and bonding comprises chemical bonding. In embodiments, the contacting and bonding comprises heat activated catalysis. The polymer can be any hydrolyzable polymer disclosed herein that includes hydroxide or amine groups that can be acylated. In embodiments, the hydrolyzable polymer comprises a polyvinyl alcohol polymer such as a polyvinyl alcohol copolymer, a modified polyvinyl alcohol copolymer, and a combination thereof. In embodiments, the polyvinyl alcohol copolymer comprises an anionically modified copolymer. In embodiments, the anionically modified copolymer comprises a carboxylate, a sulfonate, or a combination thereof. In embodiments, the fiber further comprises an additional polymer. The acylation agent solution can comprise any acylation agent disclosed herein and any solvent disclosed herein. In embodiments, the fiber is not soluble in the solvent prior to treatment, during treatment, and after treatment The disclosure further provides a nonwoven web treated according to the method of the disclosure. The disclosure provides a nonwoven web comprising the fibers of the disclosure. The disclosure provides a multilayer nonwoven web comprising a first layer comprising a nonwoven web treated according to the method of the disclosure or a nonwoven web comprising the fibers of the disclosure.

Biodegradability

Polyvinyl alcohol polymers are generally biodegradable as they decompose in the presence of water and enzymes under aerobic, anaerobic, soil, and compost conditions (in the presence of water). In general, as the degree of hydrolysis of a polyvinyl alcohol polymer increases up to about 80%, the biodegradation activity of the polyvinyl alcohol polymer increases. Without intending to be bound by theory, it is believed that increasing the degree of hydrolysis above 80% does not appreciably affect biodegradability. Additionally, the stereoregularity of the hydroxyl groups of polyvinyl alcohol polymers has a large effect on the biodegradability activity level and the more isotactic the hydroxyl groups of the polymer sequence, the higher degradation activity becomes. Without intending to be bound by theory, for soil and/or compost biodegradation it is believed that a nonwoven web prepared from a polyvinyl alcohol fiber will have higher biodegradation activity levels relative to a water-soluble film prepared from a similar polyvinyl alcohol polymer, due to the increase in the polymer surface area provided by the nonwoven web, relative to a film. Further, without intending to be bound by theory, it is believed that while the degree of polymerization of the polyvinyl alcohol polymer has little to no effect on the biodegradability of a film or nonwoven web prepared with the polymer, the polymerization temperature may have an effect on the biodegradability of a film or nonwoven because the polymerization temperature can affect the crystallinity and aggregating status of a polymer. In particular, as the crystallinity decreases, the polymer chain hydroxyl groups become less aligned in the polymer structure and the polymer chains become more disordered allowing for chains to accumulate as amorphous aggregates, thereby decreasing availability of ordered polymer structures such that the biodegradation activity is expected to decrease for soil and/or compost biodegradation mechanisms wherein the polymer is not dissolved. Without intending to be bound by theory, it is believed that because the stereoregularity of the hydroxyl groups of polyvinyl alcohol polymers has a large effect on biodegradability activity levels, the substitution of functionalities other than hydroxyl groups (e.g., anionic AMPS functional groups, carboxylate groups, or lactone groups) is expected to decrease the biodegradability activity level, relative to a polyvinyl alcohol homopolymer or copolymer having the same degree of hydrolysis, unless the functional group itself is also biodegradable, in which case biodegradability of the polymer can be increased with substitution. Further, it is believed that while the biodegradability activity level of a substituted polyvinyl alcohol (or a modified polyvinyl alcohol copolymer) can be less than that of the corresponding homopolymer or copolymer, the substituted polyvinyl alcohol will still exhibit biodegradability.

Methods of determining biodegradation activity are known in the art, for example, as described in Chiellini et al., Progress in Polymer Science, Volume 28, Issue 6, 2003, pp. 963-1014, which is incorporated herein by reference in its entirety. Further methods and standards can be found in ECHA's Annex XV Restriction Report—Microplastics, Version number 1, Jan. 11, 2019, which is incorporated herein by reference in its entirety. Suitable standards include OECD 301B (ready biodegradability), OECD 301B (enhanced biodegradation), OECD 302B (inherent biodegradability), OECD 311 (anaerobic), ASTM D5988 (soil).

In embodiments, the fibers and nonwoven webs of the disclosure can be of the standard ready biodegradation, enhanced biodegradation, or inherent biodegradation. As used herein, the term "ready biodegradation" refers to a standard that is met if the material (e.g., a fiber) reached 60% biodegradation (mineralization) within 28 days of the beginning of the test, according to the OECD 301B test as described in said ECHA's Annex XV. As used herein, the term "enhanced biodegradation" refers to a standard that is met if the material (e.g., a fiber) reaches 60% biodegradation within 60 days from the beginning of the test, according to the OECD 301B test as described in said ECHA's Annex XV. In embodiments, the fibers and nonwoven webs of the disclosure meet the standards of ready biodegradation. In embodiments, the fibers and nonwoven webs of the disclosure meet the standards of ready biodegradation or enhanced degradation. In embodiments, the fibers and nonwoven webs of the disclosure meet the standards of inherent biodegradation. In embodiments, the fibers and nonwoven webs of the disclosure meet the standards of enhanced degradation. In embodiments, the fibers and nonwoven webs of the disclosure meet the standards of inherent biodegradation, enhanced biodegradation, or ready biodegradation. In embodiments, the laminate (nonwoven and film) of the disclosure meet the standards of ready biodegradation or enhanced biodegradation.

Uses

The nonwoven webs of the disclosure are suitable for a variety of commercial applications. Suitable commercial applications for the nonwoven webs of the disclosure can include, but are not limited to, water-dispersible or flushable pouches and packets; medical uses such as surgical masks, medical packaging, shoe covers, wound dressing, and drug delivery; filtration systems such as for gasoline and oil, mineral processing, vacuum bags, air filters, and allergen membranes or laminates; personal care products such as for baby wipes, makeup removing wipes, exfoliating clothes, makeup applicators, and wearable absorbent articles such as diapers and adult incontinence products; office products such as shopping bags or envelopes; and others such as lens cleaning wipes, cleanroom wipes, potting material for plants, antibacterial wipes, agricultural seed strips, fabric softener sheets, garment/laundry bags, food wrapping, floor care wipes, pet care wipes, polishing tools, dust removal, and hand cleaning.

Sealed Pouches

The disclosure further provides a pouch comprising a nonwoven web according to the disclosure in the form of a pouch defining an interior pouch volume. In some embodiments, the pouch can include a laminate comprising a water-soluble film and a nonwoven web of the disclosure. The pouch can be a water-dispersible pouch, optionally a water-soluble pouch and/or a flushable pouch. The disclosure further provides a method of preparing a packet comprising a nonwoven web of the disclosure, the method comprising forming a nonwoven web into the form of a pouch, filling the pouch with a composition to be enclosed therein, and sealing the pouch to form a packet. In some embodiments, sealing includes heat sealing, solvent welding, adhesive sealing, or a combination thereof.

The nonwoven webs and laminates disclosed herein are useful for creating a sealed article in the form of a pouch defining an interior pouch volume to contain a composition therein for release into an aqueous environment. A "sealed article" optionally encompasses sealed compartments having a vent hole, for example, in embodiments wherein the compartment encloses a solid that off-gasses, but more commonly will be a completely sealed compartment.

The pouches may comprise a single compartment or multiple compartments. A pouch can be formed from two layers of nonwoven web or laminate sealed at an interface, or by a single nonwoven web or laminate that is folded upon itself and sealed. The nonwoven web or laminate forms at least one side wall of the pouch, optionally the entire pouch, and preferably an outer surface of the at least one sidewall. In another type of embodiment, the nonwoven web or laminate forms an inner wall of the packet, e.g., as a dividing wall between compartments. The nonwoven web or laminate can also be used in combination with a water-soluble film, e.g., as an exterior wall, inner wall, and/or compartment lid.

The composition enclosed in the pouch is not particularly limited, for example including any of the variety of compositions described herein. In embodiments comprising multiple compartments, each compartment may contain identical and/or different compositions. In turn, the compositions may take any suitable form including, but not limited to liquid, solid, gel, paste, mull, pressed solids (tablets) and combinations thereof (e.g., a solid suspended in a liquid).

In some embodiments, the pouches comprise multiple compartments. The multiple compartments are generally superposed such that the compartments share a partitioning wall interior to the pouch. The compartments of multi-compartment pouches may be of the same or different size(s) and/or volume(s). The compartments of the present multi-compartment pouches can be separate or conjoined in any suitable manner. In embodiments, the second and/or third and/or subsequent compartments are superimposed on the first compartment. In one embodiment, the third compartment may be superimposed on the second compartment, which is in turn superimposed on the first compartment in a sandwich configuration. Alternatively, the second and third compartments may be superimposed on the first compartment. However, it is also equally envisaged that the first, the second and/or third and/or subsequent compartments are orientated side-by-side or in concentric orientations. The compartments may be packed in a string, each compartment being individually separable by a perforation line. Hence each compartment may be individually torn-off from the remainder of the string by the end-user. In some embodiments, the first compartment may be surrounded by at least the second compartment, for example in a tire-and-rim configuration, or in a pouch-in-a-pouch configuration.

The geometry of the compartments may be the same or different. In embodiments the optionally third and subsequent compartments each have a different geometry and shape as compared to the first and second compartment. In these embodiments, the optionally third and subsequent compartments are arranged in a design on the first or second compartment. The design may be decorative, educative, or illustrative, for example to illustrate a concept or instruction, and/or used to indicate origin of the product.

Methods of Making Pouches

Pouches and packets may be made using any suitable equipment and method. For example, single compartment pouches may be made using vertical form filling, horizontal form filling, or rotary drum filling techniques commonly known in the art. Such processes may be either continuous or intermittent. The nonwoven web, layered nonwoven web and film, or laminate structure may be dampened, and/or heated to increase the malleability thereof. The method may also involve the use of a vacuum to draw the nonwoven web, layered nonwoven web and film, or laminate structure into a suitable mold. The vacuum drawing the nonwoven web or laminate into the mold can be applied for about 0.2 to about 5 seconds, or about 0.3 to about 3, or about 0.5 to about 1.5 seconds, once the nonwoven web, layered nonwoven web and film, or laminate structure is on the horizontal portion of the surface. This vacuum can be such that it provides an under-pressure in a range of 10 mbar to 1000 mbar, or in a range of 100 mbar to 600 mbar, for example.

The molds, in which packets may be made, can have any shape, length, width and depth, depending on the required dimensions of the pouches. The molds may also vary in size and shape from one to another, if desirable. For example, the volume of the final pouches may be about 5 ml to about 300 ml, or about 10 ml to 150 ml, or about 20 ml to about 100 ml, and that the mold sizes are adjusted accordingly.

Thermoforming

A thermoformable nonwoven web or laminate is one that can be shaped through the application of heat and a force. Thermoforming a nonwoven web, layered nonwoven web and film, or laminate structure is the process of heating the nonwoven web, layered nonwoven web and film, or laminate structure, shaping it (e.g., in a mold), and then allowing the resulting nonwoven web or laminate to cool, whereupon the nonwoven web or laminate will hold its shape, e.g., the shape of the mold. The heat may be applied using any suitable means. For example, the nonwoven web or laminate may be heated directly by passing it under a heating element or through hot air, prior to feeding it onto a surface or once on a surface. Alternatively, it may be heated indirectly, for example by heating the surface or applying a hot item onto the nonwoven web or laminate. In embodiments, the non-woven web or laminate is heated using an infrared light. The nonwoven web or laminate may be heated to a temperature in a range of about 50° C. to about 200° C., about 50° C. to about 170° C., about 50° C. to about 150° C., about 50° C. to about 120° C., about 60° C. to about 130° C., about 70° C. to about 120° C., or about 60° C. to about 90° C. Thermoforming can be performed by any one or more of the following processes: the manual draping of a thermally softened nonwoven web or laminate over a mold, or the pressure induced shaping of a softened nonwoven web or laminate to a mold (e.g., vacuum forming), or the automatic high-speed indexing of a freshly extruded sheet having an accurately known temperature into a forming and trimming station, or the automatic placement, plug and/or pneumatic stretching and pressuring forming of a nonwoven web or laminate.

Alternatively, the nonwoven web or laminate can be wetted by any suitable means, for example directly by spraying a wetting agent (including water, a polymer composition, a plasticizer for the nonwoven web or laminate composition, or any combination of the foregoing) onto the nonwoven web or laminate, prior to feeding it onto the surface or once on the surface, or indirectly by wetting the surface or by applying a wet item onto the nonwoven web or laminate.

Once a nonwoven web or laminate has been heated and/or wetted, it may be drawn into an appropriate mold, preferably using a vacuum. The filling of the molded nonwoven web or laminate can be accomplished by utilizing any suitable means. In embodiments, the most preferred method will depend on the product form and required speed of filling. In embodiments, the molded nonwoven web or laminate is filled by in-line filling techniques. The filled, open packets are then closed forming the pouches, using a second non-woven web or laminate, by any suitable method. This may be accomplished while in horizontal position and in con-tinuous, constant motion. The closing may be accomplished by continuously feeding a second nonwoven web or lami-nate, preferably water-soluble nonwoven web or laminate, over and onto the open packets and then preferably sealing the first and second nonwoven web or laminate together, typically in the area between the molds and thus between the packets.

Sealing the Pouches

Any suitable method of sealing the pouch and/or the individual compartments thereof may be utilized. Non-limiting examples of such means include heat sealing, solvent welding, solvent or wet sealing, and combinations thereof. Typically, only the area which is to form the seal is treated with heat or solvent. The heat or solvent can be applied by any method, typically on the closing material, and typically only on the areas which are to form the seal. If solvent or wet sealing or welding is used, it may be preferred that heat is also applied. Preferred wet or solvent sealing/welding methods include selectively applying sol-vent onto the area between the molds, or on the closing material, by for example, spraying or printing this onto these areas, and then applying pressure onto these areas, to form the seal. Sealing rolls and belts (optionally also providing heat) can be used, for example.

In embodiments, an inner nonwoven web or laminate is sealed to outer nonwoven web(s) or laminate(s) by solvent sealing. The sealing solution is generally an aqueous solu-tion. In embodiments, the sealing solution includes water. In embodiments, the sealing solution includes water and fur-ther includes one or more polyols, diols and/or glycols such as 1,2-ethanediol (ethylene glycol), 1,3-propanediol, 1,2-propanediol, 1,4-butanediol (tetramethylene glycol), 1,5-pantanediol (pentamethylene glycol), 1,6-hexanediol (hex-amethylene glycol), 2,3-butanediol, 1,3-butanediol, 2-methyl-1,3-propanediol, various polyethylene glycols (e.g., diethylene glycol, triethylene glycol), and combina-tions thereof. In embodiments, the sealing solution includes erythritol, threitol, arabitol, xylitol, ribitol, mannitol, sorbi-tol, galactitol, fucitol, iditol, inositol, volemitol, isomal, maltitol, lactitol. In embodiments, the sealing solution includes a water-soluble polymer.

The sealing solution can be applied to the interfacial areas of the inner nonwoven web or laminate in any amount suitable to adhere the inner and outer nonwoven webs or laminates. As used herein, the term "coat weight" refers to the amount of sealing solution applied to the nonwoven web or laminate in grams of solution per square meter of non-woven web or laminate. In general, when the coat weight of the sealing solvent is too low, the nonwoven webs or laminates do not adequately adhere and the risk of pouch failure at the seams increases. Further, when the coat weight of the sealing solvent is too high, the risk of the solvent migrating from the interfacial areas increases, increasing the likelihood that etch holes may form in the sides of the pouches. The coat weight window refers to the range of coat weights that can be applied to a given film while maintaining both good adhesion and avoiding the formation of etch holes. A broad coat weight window is desirable as a broader window provides robust sealing under a broad range of operations. Suitable coat weight windows are at least about 3 $g/m^2$, or at least about 4 $g/m^2$, or at least about 5 $g/m^2$, or at least about 6 $g/m^2$.

Cutting the Packets

Formed packets may be cut by a cutting device. Cutting can be accomplished using any known method. It may be preferred that the cutting is also done in continuous manner, and preferably with constant speed and preferably while in horizontal position. The cutting device can, for example, be a sharp item, or a hot item, or a laser, whereby in the latter cases, the hot item or laser 'burns' through the film/sealing area.

Forming and Filling Multi-Compartment Pouches

The different compartments of a multi-compartment pouches may be made together in a side-by-side style or concentric style wherein the resulting, cojoined pouches may or may not be separated by cutting. Alternatively, the compartments can be made separately.

In embodiments, pouches may be made according to a process comprising the steps of: a) forming a first compart-ment (as described above); b) forming a recess within or all of the closed compartment formed in step (a), to generate a second molded compartment superposed above the first compartment; c) filling and closing the second compartments by means of a third nonwoven web, laminate, or film; d) sealing the first, second and third nonwoven web, laminate, or film; and e) cutting the nonwoven webs or laminates to produce a multi-compartment pouch. The recess formed in step (b) may be achieved by applying a vacuum to the compartment prepared in step (a).

In embodiments, second, and/or third compartment(s) can be made in a separate step and then combined with the first compartment as described in European Patent Application Number 08101442.5 or U.S. Patent Application Publication No. 2013/240388 A1 or WO 2009/152031.

In embodiments, pouches may be made according to a process comprising the steps of: a) forming a first compartment, optionally using heat and/or vacuum, using a first nonwoven web or laminate on a first forming machine; b) filling the first compartment with a first composition; c) optionally filling the second compartment with a second composition; d) sealing the first and optional second compartment with a second nonwoven web or laminate to the first nonwoven web or laminate; and e) cutting the nonwoven webs or laminates to produce a multi-compartment pouch.

In embodiments, pouches may be made according to a process comprising the steps of: a) forming a first compartment, optionally using heat and/or vacuum, using a first nonwoven web or laminate on a first forming machine; b) filling the first compartment with a first composition; c) on a second forming machine, deforming a second nonwoven web or laminate, optionally using heat and vacuum, to make a second and optionally third molded compartment; d) filling the second and optionally third compartments; e) sealing the second and optionally third compartment using a third nonwoven web or laminate; f) placing the sealed second and optionally third compartments onto the first compartment; g) sealing the first, second and optionally third compartments; and h) cutting the nonwoven web or laminate to produce a multi-compartment pouch.

The first and second forming machines may be selected based on their suitability to perform the above process. In embodiments, the first forming machine is preferably a horizontal forming machine, and the second forming machine is preferably a rotary drum forming machine, preferably located above the first forming machine.

It should be understood that by the use of appropriate feed stations, it may be possible to manufacture multi-compartment pouches incorporating a number of different or distinctive compositions and/or different or distinctive liquid, gel or paste compositions.

In embodiments, the nonwoven web or laminate and/or pouch is sprayed or dusted with a suitable material, such as an active agent, a lubricant, an aversive agent, or mixtures thereof. In embodiments, the nonwoven web or laminate and/or pouch is printed upon, for example, with an ink and/or an active agent.

Vertical Form, Fill and Seal

In embodiments, the nonwoven web or laminate of the disclosure can be formed into a sealed article. In embodiments, the sealed article is a vertical form, filled, and sealed article. The vertical form, fill, and seal (VFFS) process is a conventional automated process. VFFS includes an apparatus such as an assembly machine that wraps a single piece of the nonwoven web or laminate around a vertically oriented feed tube. The machine heat seals or otherwise secures the opposing edges of the nonwoven web or laminate together to create the side seal and form a hollow tube of nonwoven web or laminate. Subsequently, the machine heat seals or otherwise creates the bottom seal, thereby defining a container portion with an open top where the top seal will later be formed. The machine introduces a specified amount of flowable product into the container portion through the open top end. Once the container includes the desired amount of product, the machine advances the nonwoven web or laminate to another heat sealing device, for example, to create the top seal. Finally, the machine advances the nonwoven web or laminate to a cutter that cuts the film immediately above the top seal to provide a filled package.

During operation, the assembly machine advances the nonwoven web or laminate from a roll to form the package. Accordingly, the nonwoven web or laminate must be able to readily advance through the machine and not adhere to the machine assembly or be so brittle as to break during processing.

Pouch Contents

In any embodiment, the pouch can contain (enclose) a composition in the defined interior volume of the pouch. The composition can be selected from a liquid, solid or combination thereof. In embodiments wherein the composition includes a liquid, the nonwoven web can be a nonporous nonwoven web or a porous nonwoven web laminated with a water-soluble film, the water-soluble film forming the inner surface of the pouch. In embodiments wherein the composition is a solid, the pouch can comprise a nonporous nonwoven web, a porous nonwoven web laminated with a water-soluble film, or a porous nonwoven web. In embodiments wherein the pouch includes a porous nonwoven web, the particle size of the solid composition is smaller than the pore size of the nonwoven web.

In embodiments, the sealed articles of the disclosure can enclose in the interior pouch volume a composition comprising a liquid laundry detergent, an agricultural composition, an automatic dish washing composition, household cleaning composition, a water-treatment composition, a personal care composition, a food and nutritive composition, an industrial cleaning composition, a medical composition, a disinfectant composition, a pet composition, an office composition, a livestock composition, an industrial composition, a marine composition, a mercantile composition, a military composition, a recreational composition, or a combination thereof. In embodiments, the water-dispersible sealed articles of the disclosure can enclose in the interior pouch volume a composition comprising a liquid laundry detergent, an agricultural composition, an automatic dish washing composition, a household cleaning composition, a water-treatment composition, a personal care composition, a food and nutritive composition, an industrial cleaning composition, or a combination thereof. In embodiments, the water-dispersible sealed articles of the disclosure can enclose in the interior pouch volume a composition comprising a liquid laundry detergent, an agricultural composition, an automatic dish washing composition, a household cleaning composition, a water-treatment composition, a personal care composition, or a combination thereof. In embodiments, the water-dispersible sealed articles of the disclosure can enclose in the interior pouch volume a composition comprising an agricultural composition or a water-treatment composition.

As used herein, "liquid" includes free-flowing liquids, as well as pastes, gels, foams and mousses. Non-limiting examples of liquids include light duty and heavy duty liquid detergent compositions, dish detergent for hand washing and/or machine washing; hard surface cleaning compositions, fabric enhancers, detergent gels commonly used for laundry, bleach and laundry additives, shaving creams, skin care, hair care compositions (shampoos and conditioners), and body washes. Such detergent compositions may comprise a surfactant, a bleach, an enzyme, a perfume, a dye or colorant, a solvent and combinations thereof. Optionally, the detergent composition is selected from the group consisting of a laundry detergent, a dishwashing detergent, a hard surface cleaning composition, fabric enhancer compositions, shaving creams, skin care, hair care compositions (shampoos and conditioners), and body washes, and combinations thereof.

Non-limiting examples of liquids include agricultural compositions, automotive compositions, aviation compositions, food and nutritive compositions, industrial compositions, livestock compositions, marine compositions, medical compositions, mercantile compositions, military and quasi-military compositions, office compositions, recreational and park compositions, pet compositions, and water-treatment compositions, including cleaning and detergent compositions applicable to any such use.

Gases, e.g., suspended bubbles, or solids, e.g., particles, may be included within the liquids. A "solid" as used herein includes, but is not limited to, powders, agglomerates, and mixtures thereof. Non-limiting examples of solids include: granules, micro-capsules, beads, noodles, and pearlised balls. Solid compositions may provide a technical benefit including, but not limited to, through-the-wash benefits, pre-treatment benefits, and/or aesthetic effects.

The composition may be a non-household care composition. For example, a non-household care composition can be selected from agricultural compositions, aviation compositions, food and nutritive compositions, industrial compositions, livestock compositions, marine compositions, medical compositions, mercantile compositions, military and quasi-military compositions, office compositions, recreational and park compositions, pet compositions, and water-treatment compositions, including cleaning and detergent compositions applicable to any such use while excluding fabric and household care compositions In one type of embodiment, the composition can include an agrochemical, e.g., one or more insecticides, fungicides, herbicides, pesticides, miticides, repellants, attractants, defoliaments, plant growth regulators, fertilizers, bactericides, micronutrients, and trace elements. Suitable agrochemicals and secondary agents are described in U.S. Pat. Nos. 6,204,223 and 4,681,228 and EP 0989803 A1. For example, suitable herbicides include paraquat salts (for example paraquat dichloride or paraquat bis(methylsulphate), diquat salts (for example diquat dibromide or diquat alginate), and glyphosate or a salt or ester thereof (such as glyphosate isopropylammonium, glyphosate sesquisodium or glyphosate trimesium, also known as sulfosate). Incompatible pairs of crop protection chemicals can be used in separate chambers, for example as described in U.S. Pat. No. 5,558,228. Incompatible pairs of crop protection chemicals that can be used include, for example, bensulfuron methyl and molinate; 2,4-D and thifensulfuron methyl; 2,4-D and methyl 2-[[[[N-4-methoxy-6-methyl-1,3,5-triazine-2-yl)-N-methylamino]carbonyl]amino]-sulfonyl]benzoate; 2,4-D and metsulfuron methyl; maneb or mancozeb and benomyl; glyphosate and metsulfuron methyl; tralomethrin and any organophosphate such as monocrotophos or dimethoate; bromoxynil and N-[[4,6-dimethoxypyrimidine-2-yl)-amino]carbonyl]-3-(ethylsulfonyl)-2-pyridine-sulfonamide; bromoxynil and methyl 2-[[[[(4-methyl-6-methoxy)-1,3,5-triazin-2-yl)amino]carbonyl]amino]sulfonyl]-benzoate; bromoxynil and methyl 2-[[[[N-(4-methoxy-6-methyl-1,3,5-triazin-2-yl)-N-methylamino]carbonyl]amino]-sulfonyl]

benzoate. In another, related, type of embodiment, the composition can include one or more seeds, optionally together with soil, and further optionally together with one or more additional components selected from mulch, sand, peat moss, water jelly crystals, and fertilizers, e.g., including types of embodiments described in U.S. Pat. No. 8,333,033.

In another type of embodiment, the composition is a water-treatment agent. Such agents can include harsh chemicals, such as aggressive oxidizing chemicals, e.g., as described in U.S. Patent Application Publication No. 2014/0110301 and U.S. Pat. No. 8,728,593. For example, sanitizing agents can include hypochlorite salts such as sodium hypochlorite, calcium hypochlorite, and lithium hypochlorite; chlorinated isocyanurates such as dichloroisocyanuric acid (also referred to as "dichlor" or dichloro-s-triazinetrione, 1,3-dichloro-1,3,5-triazinane-2,4,6-trione) and trichloroisocyanuric acid (also referred to as "trichlor" or I,3,5-trichloro-I,3,5-triazinane-2,4,6-trione). Salts and hydrates of the sanitizing compounds are also contemplated. For example, dichloroisocyanuric acid may be provided as sodium dichloroisocyanurate, sodium dichloroisocyanurate acid dihydrate, among others. Bromine containing sanitizing agents may also be suitable for use in unit dose packaging applications, such as I,3-dibromo-5,5-dimethylhydantoin (DBDMH), 2,2-dibromo-3-nitrilopropionamide (DBNPA), dibromocyano acetic acid amide, 1-bromo-3-chloro-5,5-dimethylhydantoin; and 2-bromo-2-nitro-1,3-propanediol, among others. The oxidizing agent can be one described in U.S. Pat. No. 7,476,325, e.g., potassium hydrogen peroxymonosulfate. The composition can be a pH-adjusting chemical, e.g., as described in U.S. Patent Application Publication No. 2008/0185347, and can include, for example, an acidic component and an alkaline component such that the composition is effervescent when contacted with water, and adjusts the water pH. Suitable ingredients include sodium bicarbonate, sodium bisulfate, potassium hydroxide, sulfamic acid, organic carboxylic acids, sulfonic acids, and potassium dihydrogen phosphate. A buffer blend can include boric acid, sodium carbonate, glycolic acid, and oxone monopersulfate, for example.

A water-treatment agent can be or can include a flocculant, e.g., as described in U.S. Patent Application Publication No. 2014/0124454. The flocculant can include a polymer flocculant, e.g., polyacrylamide, a polyacrylamide copolymer such as an acrylamide copolymers of diallydimethylammonium chloride (DADMAC), dimethylaminoethylacrylate (DMAEA), dimethylaminoethylmethacrylate (DMAEM), 3-methylamidepropyltrimethylammonium chloride (MAPTAC) or acrylic acid; a cationic polyacrylamide; an anionic polyacrylamide; a neutral polyacrylamide; a polyamine; polyvinylamine; polyethylene imine; polydimethyldiallylammonium chloride; poly oxyethylene; polyvinyl alcohol; polyvinyl pyrrolidone; polyacrylic acid; polyphosphoric acid; polystyrene sulfonic acid; or any combination thereof. A flocculant can be selected from chitosan acetate, chitosan lactate, chitosan adipate, chitosan glutamate, chitosan succinate, chitosan malate, chitosan citrate, chitosan fumarate, chitosan hydrochloride, and combinations thereof. The water-treating composition can include a phosphate removing substance, e.g., one or more selected from a zirconium compound, a rare earth lanthanide salt, an aluminum compound, an iron compound, or any combination thereof.

The composition can be a limescale removing composition, e.g., citric or maleic acid or a sulfate salt thereof, or any mixture thereof, e.g., as described in U.S. Patent Application No. 2006/0172910.

Various other types of compositions are contemplated for use in the packets described herein, including particulates, for example down feathers, e.g., as described in U.S. RE29059 E; super absorbent polymers, e.g., as described in U.S. Patent Application Publication Nos. 2004/0144682 and 2006/0173430; pigments and tinters, e.g., as described in U.S. Pat. No. 3,580,390 and U.S. Patent Application Publication No. 2011/0054111; brazing flux (e.g., alkali metal fluoroaluminates, alkali metal fluorosilicates and alkali metal fluorozincates), e.g., as described in U.S. Pat. No. 8,163,104; food items (e.g., coffee powder or dried soup) as described in U.S. Patent Application Publication No. 2007/0003719; and wound dressings, e.g., as described in U.S. Pat. No. 4,466,431.

In pouches comprising laundry, laundry additive and/or fabric enhancer compositions, the compositions may comprise one or more of the following non-limiting list of ingredients: fabric care benefit agent; detersive enzyme; deposition aid; rheology modifier; builder; bleach; bleaching agent; bleach precursor; bleach booster; bleach catalyst; perfume and/or perfume microcapsules (see for example U.S. Pat. No. 5,137,646); perfume loaded zeolite; starch encapsulated accord; polyglycerin esters; whitening agent; pearlescent agent; enzyme stabilizing systems; scavenging agents including fixing agents for anionic dyes, complexing agents for anionic surfactants, and mixtures thereof; optical brighteners or fluorescers; polymer including but not limited to soil release polymer and/or soil suspension polymer; dispersants; antifoam agents; non-aqueous solvent; fatty acid; suds suppressors, e.g., silicone suds suppressors (see: U.S. Publication No. 2003/0060390 A1, ¶65-77); cationic starches (see: U.S. 2004/0204337 A1 and US 2007/0219111 A1); scum dispersants (see: U.S. 2003/0126282 A1, ¶89-90); substantive dyes; hueing dyes (see: U.S. 2014/0162929 A1); colorants; opacifier; antioxidant; hydrotropes such as toluenesulfonates, cumenesulfonates and naphthalenesulfonates; color speckles; colored beads, spheres or extrudates; clay softening agents; anti-bacterial agents. Any one or more of these ingredients is further described in described in US Patent Application Publication Number U.S. 2010/305020 A1, U.S. Publication Number 2003/0139312A1 and U.S. Patent Application Publication Number U.S. 2011/0023240 A1. Additionally, or alternatively, the compositions may comprise surfactants, quaternary ammonium compounds, and/or solvent systems. Quaternary ammonium compounds may be present in fabric enhancer compositions, such as fabric softeners, and comprise quaternary ammonium cations that are positively charged polyatomic ions of the structure $NR_4^+$, where R is an alkyl group or an aryl group.

Composite Articles

Composite articles of the disclosure include at least two layers of nonwoven webs. The composite articles of the disclosure can have a first layer of a first nonwoven web including a first plurality of fibers having a first diameter, a second layer of a second nonwoven web comprising a second plurality of fibers having a second diameter, and a first interface comprising at least a portion of the first nonwoven web and at least a portion of the second nonwoven web, wherein the portion of the first nonwoven web and the portion of the second nonwoven web are fused, and wherein the second diameter is smaller than the first diameter. Any nonwoven layer of the composite article can include a water-soluble film laminated thereto.

Composite articles of the disclosure can provide one or more advantages, including but not limited to, increased mechanical strength relative to a nonwoven web identical to a single layer of the composite article alone, enhanced liquid acquisition function relative to a nonwoven web identical to a single layer of the composite article alone (e.g., for a liquid acquisition layer of a diaper, or for a spill absorbing wipe), and/or enhanced retention of fluids and/or active compositions relative to a nonwoven web identical to a single layer of the composite article alone (e.g., an active lotion for a wet wipe).

The first interface including at least a portion of the first nonwoven web and at least a portion of the second nonwoven web is the area of the composite where the first and second nonwoven webs overlap and the first plurality of fibers and the second plurality of fibers are intermingled. In general, the portion of the first nonwoven web that forms the first interface is an exterior surface of the first nonwoven web. In embodiments, the first interface comprises 50% or less of the thickness of the first nonwoven web, 40% or less, 30% or less, 25% or less, 20% or less, 10% or less, 5% or less, 2.5% or less, or 1% or less of the thickness of the first nonwoven web. In embodiments, the first interface comprises at least 0.1%, at least 0.5%, at least 1%, or at least 5% of the thickness of the first nonwoven. In embodiments, the first interface comprises about 0.1% to about 25% of the thicknesses of the first nonwoven. In general, the portion of the second nonwoven web that forms the interface is an exterior surface of the second nonwoven web. In embodiments, the interface comprises 75% or less, 70% or less, 60% or less, 50% or less, 40% or less, 30% or less, 25% or less, 20% or less, or 15% or less of the thickness of the second nonwoven web. In embodiments, the first interface comprises at least 1%, at least 5%, at least 10%, at least 20%, at least 25%, at least 30%, or at least 40% of the thickness of the second nonwoven web. In embodiments, the first interface comprises from about 1% to about 75% of the thickness of the second nonwoven web.

As used herein, and unless specified otherwise, two layers of nonwoven webs are "fused" if at least a portion of the fibers from each web are bonded to fibers from the other web. As described herein, bonding of the fibers includes entangling of the fibers. The two layers of nonwoven webs can be fused using any suitable method. In embodiments, the portion of the first nonwoven web and the portion of the second nonwoven web are thermally fused, solvent fused, or both. In embodiments, the portion of the first nonwoven web and the portion of the second nonwoven web are thermally fused. Thermal fusion can include the use of heat and/or pressure. In embodiments, one or both of two discrete nonwoven webs can be heated until the fibers are soft and the webs can then be pressed together such that when the fibers cool at least a portion of fibers from each web are bonded to at least a portion of fibers from the other web. In embodiments, one or both of the first and second nonwoven webs can be melt-spun and applied in an inline process such that heated, soft fibers are applied directly to a pre-formed nonwoven web after passing through the die assembly and fuse to the fibers of the pre-formed nonwoven forming a fused interface. In embodiments, the portion of the first nonwoven web and the portion of the second nonwoven web are solvent fused. Solvent fusion can include the application of a binder solution to one or both of the nonwoven webs followed by contacting the nonwoven webs such that upon drying, at least a portion of fibers from each web are bonded to at least a portion of fibers from the other web. Solvent fusion can occur as a discrete process including two discrete pre-formed webs or can be an inline process wherein a binder solution is applied to a pre-formed nonwoven web and a second nonwoven web is formed on the pre-formed nonwoven web in a continuous process. The binder solution for solvent fusion of the nonwoven web can be any binder solution described herein for binding. As used herein, and unless specified otherwise, a "pre-formed nonwoven web" encompasses nonwoven webs formed but not bonded and nonwoven webs that have been formed and bonded. As used herein, and unless specified otherwise, a "discrete nonwoven web" encompasses nonwoven webs formed by carding or airlaying staple fibers, or by continuous processes, and the nonwoven webs may or may not be bonded. In embodiments, the fusing of two nonwoven webs can also be used to bond one or both of the nonwoven webs.

In embodiments, the first interface is solvent fused and the solvent is selected from the group consisting of water, ethanol, methanol, DMSO, glycerin, and a combination thereof. In embodiments, the first interface is solvent fused and the solvent is selected from the group consisting of water, glycerin, and a combination thereof. In embodiments, the first interface is solvent fused using a binder solution comprising polyvinyl alcohol and water, glycerin, or a combination thereof. In embodiments, the first interface is solvent fused using a binder solution comprising polyvinyl alcohol, latex, or a combination thereof and water, glycerin, or a combination thereof.

As used herein, and unless specified otherwise, a first type of fiber has a diameter that is "smaller than" the diameter of a second type of fiber if the average fiber diameter for the first type of fiber is less than the average fiber diameter of the second type of fiber. For example, the first type of fiber can have an overlapping diameter size distribution with the second type of fiber and still have a smaller diameter as long as the average fiber diameter for the first type of fiber is smaller than the average fiber diameter of the second type of fiber. In embodiments, the smaller fiber type has an average fiber diameter that is smaller than the smallest diameter of the diameter size distribution of the larger fiber type. A difference in diameter is present if the difference can be visualized using projection microscope imaging as outlined in SO137:2015. In embodiments, the difference in diameter between the smaller fiber type and the larger fiber type can be submicron, for example, if multiple melt-spun layers are used. In embodiments, the difference in the diameter between the smaller fiber type and the larger fiber type can be about 1 micron to about 300 micron, about 5 micron to about 300 micron, about 5 micron to about 250 micron, about 5 micron to about 200 micron, about 10 micron to about 150 micron, about 10 micron to about 100 micron, about 10 micron to about 90 micron, about 15 micron to about 80 micron, about 15 micron to about 70 micron, about 20 micron to about 60 micron, about 20 micron to about 50 micron, or about 25 micron to about 45 micron. In embodiments, the difference in diameter between the smaller fiber type and the larger fiber type can be about 5 micron to about 75 micron. In embodiments, the difference in diameter between the smaller fiber type and the larger fiber type can be about 20 micron to about 80 micron. Without intending to be bound by theory, it is believed that providing a composite of two nonwoven webs wherein the nonwoven webs are fused and the second nonwoven web has a fiber diameter that is smaller than the first nonwoven web advantageously can improve the adsorption/absorption rate and fluid capacity of the composite article, direct adsorption/absorption from larger diameter fibers to smaller diameter fibers to move the fluid preferentially; increase the surface to volume ratio of a nonwoven composite article as compared to single diameter materials resulting in increased loading capacity, and/or improved dispersion and/or total dissolution of the nonwoven composite article as compared to a nonwoven having a single diameter material. The average diameters of the fibers in the individual web layers can be any diameters provided herein. In embodiments, the first plurality of fibers in the first layer of first nonwoven can have a diameter of about 10 micron to about 300 micron, about 50 micron to about 300 micron, or about greater than about 100 micron to about 300 micron. In embodiments, the first plurality of fibers can have an average diameter of greater than about 100 micron to about 300 micron. In embodiments wherein a nonwoven layer of the nonwoven composite material includes a blend of fiber types having different diameters, if the distribution of fiber diameters is monomodal, the average fiber diameter refers to the average fiber diameter of the blend. The blend of fiber types can have distribution of fiber diameters in the nonwoven layer that bimodal or higher. When a blend of fibers has a bimodal or higher-modal diameter distribution, a fiber has a smaller diameter than the fibers of said blend when the fiber has an average fiber diameter less than the average for the distribution of the smallest diameter fibers of the blend, and a fiber is larger than the fibers of said blend when the fiber has an average fiber diameter that is greater than the average for the distribution of the larger diameter fibers of the blend.

In embodiments, the composite article further comprises a third layer of a third nonwoven web comprising a third plurality of fibers. In embodiments wherein the nonwoven composite article includes a third layer of a third nonwoven web, the second layer can be provided between the first layer and the third layer and at least a second portion of the second nonwoven web and at least a portion of the third nonwoven web can be fused, providing a second interface. The second interface including at least a second portion of the second nonwoven web and at least a portion of the third nonwoven web is the area of the composite where the second and third nonwoven webs overlap and the second plurality of fibers and the third plurality of fibers are intermingled. In some embodiments, and depending on the thickness of the second layer of second nonwoven web, the first plurality of fibers and the third plurality of fibers may become intermingled and/or fused such that there is no clear delineation between the first interface and the second interface. In general, the portion of the second nonwoven web that forms the second interface is an exterior surface of the second nonwoven web opposite from the exterior surface of the second nonwoven web fused to the first nonwoven web. In embodiments, the second interface comprises 75% or less, 70% or less, 60% or less, 50% or less, 40% or less, 30% or less, 25% or less, 20% or less, or 15% or less of the thickness of the second nonwoven web. In embodiments, the second interface comprises at least 1%, at least 5%, at least 10%, at least 20%, at least 25%, at least 30%, or at least 40% of the thickness of the second nonwoven web. In embodiments, the second interface comprises from about 1% to about 75% of the thickness of the second nonwoven web. In embodiments, the portion of the third nonwoven web that forms the second interface is an exterior surface of the third nonwoven web. In embodiments, the second interface comprises 50% or less of the thickness of the third nonwoven web, 40% or less, 30% or less, 25% or less, 20% or less, 10% or less, 5% or less, 2.5% or less, or 1% or less of the thickness of the first nonwoven web. In embodiments, the second interface comprises at least 0.1%, at least 0.5%, at least 1%, or at least 5% of the thickness of the third nonwoven. In embodiments, the second interface comprises about 0.1% to about 25% of the thicknesses of the third nonwoven.

In embodiments, the second portion of the second non-woven web and the portion of the third nonwoven web are thermally fused, solvent fused, or both. In embodiments, the second portion of the second nonwoven web and the portion of the third nonwoven web are thermally fused. In embodiments, the second portion of the second nonwoven web and the portion of the third nonwoven web are solvent fused.

In embodiments, the second interface is solvent fused and the solvent is selected from the group consisting of water, ethanol, methanol, DMSO, glycerin, and a combination thereof. In embodiments, the second interface is solvent fused and the solvent is selected from the group consisting of water, glycerin, and a combination thereof. In embodiments, the second interface is solvent fused using a binder solution comprising polyvinyl alcohol and water, glycerin, or a combination thereof. In embodiments, the second interface is solvent fused using a binder solution comprising polyvinyl alcohol, latex, or a combination thereof and water, glycerin, or a combination thereof.

In embodiments, the first layer of first nonwoven web and the second layer of second nonwoven web have different porosities. As used herein, and unless specified otherwise, two nonwoven webs have "different porosities" when the difference in porosities of the nonwoven web is at least about 1%. In embodiments, the difference in porosities between two layers of nonwoven webs in the composite articles can be about 1% to about 20%. For example, one layer of nonwoven web in a composite article can have a porosity of about 80% and a second layer of nonwoven web in the composite article can have a porosity of about 85%, a 5% difference in porosity. In embodiments, the porosity of the second nonwoven web is less than the porosity of the first nonwoven web. In embodiments, the porosity of the second nonwoven web is the same as the porosity of the first nonwoven web. As used herein, and unless specified otherwise, two nonwoven webs have the "same porosity" if the difference in porosity values between the two nonwoven webs is less than 1%.

In embodiments wherein the composite article comprises a third layer of a third nonwoven web, the third nonwoven web can have a porosity that is the same or different from the first nonwoven web. In embodiments, the third nonwoven web can have the same porosity as the first nonwoven web. In embodiments, the third nonwoven web can have a different porosity than the first nonwoven web. In embodiments, the third nonwoven web can be less porous than the first nonwoven web. In embodiments, the third nonwoven web can have the same porosity as the second nonwoven web. In embodiments, the third nonwoven web can have a different porosity than the second nonwoven web. In embodiments, the third nonwoven web can be less porous than the second nonwoven web. In embodiments, the second nonwoven web can be less porous than the first nonwoven web and the third nonwoven web can be less porous than the second nonwoven web. In embodiments, the nonwoven composite article can have a gradient of porosity between the layers of nonwoven web, wherein one exterior surface of the composite structure can have the largest porosity and the other exterior surface of the composite structure can have the smallest porosity. In embodiments, the composite structure can have a gradient of porosity between the layers of nonwoven web, wherein the exterior surfaces of the composite structure can have the largest porosity and the middle layer(s) of the composite structure can have the smallest porosity. In embodiments, the composite structure can include a fourth or higher layer of nonwoven webs such that a middle layer(s) can include the second and third layers of nonwoven webs (for a four layer composite structure), or the third layer of nonwoven web (for a five layer composite structure).

Without intending to be bound by theory, it is believed that when the porosity of the composite structure comprises a gradient, the composite structure advantageously has enhanced wicking of liquid from the more porous exterior surface to the less porous exterior surface or less porous middle layer(s).

The plurality of fibers in any given nonwoven layer of the composite article can be any of the fibers disclosed herein, and can be the same or different. In embodiments, the composition of the fiber forming materials in the first plurality, second plurality, and third plurality of fibers can be the same or different, for example, having any difference in diameter, length, tenacity, shape, rigidness, elasticity, solubility, melting point, glass transition temperature ($T_g$), fiber forming material, color, or a combination thereof. The following Table 1 demonstrates contemplated composite articles where the nonwoven layers can include fibers having three different fiber compositions, wherein each letter "A", "B", and "C" refers to a specific fiber composition and "-" means that the contemplated composite article does not include a third layer of nonwoven web. Each of the fiber compositions A, B, and C can be (a) a single fiber type including a single fiber forming material, (b) a single fiber type including a blend of fiber forming materials, (c) a blend of fiber types, each fiber type including a single fiber forming material, (d) a blend of fiber types, each fiber type including a blend of fiber forming materials, or (e) a blend of fiber types, each fiber type including a single fiber forming material or a blend of fiber forming materials.

TABLE 1

| | Composite 1 | Composite 2 | Composite 3 | Composite 4 | Composite 5 | Composite 6 | Composite 7 | Composite 8 | Composite 9 |
|---|---|---|---|---|---|---|---|---|---|
| 1st plurality | A | A | A | B | B | B | C | C | C |
| 2nd plurality | A | B | C | A | B | C | A | B | C |
| 3rd plurality | — | — | — | — | — | — | — | — | — |

| | Composite 10 | Composite 11 | Composite 12 | Composite 13 | Composite 14 | Composite 15 | Composite 16 | Composite 17 | Composite 18 |
|---|---|---|---|---|---|---|---|---|---|
| 1st plurality | A | A | A | A | A | A | A | A | A |
| 2nd plurality | A | A | A | B | B | B | C | C | C |
| 3rd plurality | A | B | C | A | B | C | A | B | C |

TABLE 1-continued

| | Composite 19 | Composite 20 | Composite 21 | Composite 22 | Composite 23 | Composite 24 | Composite 25 | Composite 26 | Composite 27 |
|---|---|---|---|---|---|---|---|---|---|
| 1st plurality | B | B | B | B | B | B | B | B | B |
| 2nd plurality | A | A | A | B | B | B | C | C | C |
| 3rd plurality | A | B | C | A | B | C | A | B | C |

| | Composite 28 | Composite 29 | Composite 30 | Composite 31 | Composite 32 | Composite 33 | Composite 34 | Composite 35 | Composite 36 |
|---|---|---|---|---|---|---|---|---|---|
| 1st plurality | C | C | C | C | C | C | C | C | C |
| 2nd plurality | A | A | A | B | B | B | C | C | C |
| 3rd plurality | A | B | C | A | B | C | A | B | C |

In embodiments, the first plurality of fibers includes water-soluble polyvinyl alcohol fiber forming material. In embodiments, the second plurality of fibers includes water-soluble polyvinyl alcohol fiber forming material. In embodiments, the first plurality of fibers and the second plurality of fibers include water-soluble polyvinyl alcohol fiber forming material. In embodiments including a third layer of nonwoven web having a third plurality of fibers, the third plurality of fibers can include a water-soluble polyvinyl alcohol fiber forming material. In embodiments, the polyvinyl alcohol fiber forming material can be present in one or more fiber types in the plurality of fibers. The water-soluble polyvinyl alcohol fiber forming materials of any of the first plurality, second plurality, or third plurality of fibers can be any water-soluble polyvinyl alcohol fiber forming material disclosed herein. In embodiments wherein two or more of the first plurality of fibers, the second plurality of fibers, and/or the third plurality of fibers include a polyvinyl alcohol fiber forming material, the polyvinyl alcohol can be the same or different in each plurality, can be the sole fiber forming material or part of blend of fiber forming material in each plurality, and if each plurality includes a different polyvinyl alcohol fiber, the difference can be in length to diameter ratio (L/D), tenacity, shape, rigidness, elasticity, solubility, melting point, glass transition temperature ($T_g$), fiber chemistry, color, or a combination thereof.

In embodiments, the fibers of the first plurality of fibers, the second plurality of fibers, and/or third plurality of fibers can include a fiber forming material other than a polyvinyl alcohol fiber forming material.

In embodiments, the first nonwoven web has a tenacity ratio (MD:CD) of about 0.5 to about 1.5. In embodiments, the first nonwoven web has a MD:CD of about 0.8 to about 1.25. In embodiments, the first nonwoven web has a MD:CD of about 0.9 to about 1.1. In embodiments, the second nonwoven web has a tenacity ratio (MD:CD) of about 0.5 to about 1.5. In embodiments, the second nonwoven web has a MD:CD of about 0.8 to about 1.25. In embodiments, the second nonwoven web has a MD:CD of about 0.9 to about 1.1. In embodiments, the third nonwoven web has a tenacity ratio (MD:CD) of about 0.5 to about 1.5. In embodiments, the third nonwoven web has a MD:CD of about 0.8 to about 1.25. In embodiments, the third nonwoven web has a MD:CD of about 0.9 to about 1.1. In embodiments, the nonwoven composite article has a tenacity ratio (MD:CD) in a range of about 0.5 to about 1.5, about 0.8 to about 1.25, about 0.9 to about 1.1, or about 0.95 to about 1.05. In embodiments, the nonwoven composite article has a MD:CD of about 0.8 to about 1.5. In embodiments, the nonwoven composite article has a MD:CD of about 0.9 to about 1.1. The MD:CD of the nonwoven composite article is related to the MD:CD ratio of each individual of layer of nonwoven web present in the composite article. Without intending to be bound by theory, it is believed that the MD:CD of the composite article cannot be determined by considering the MD and CD of each layer of nonwoven web individually, but the MD and CD of the nonwoven composite article must be measured. Without intending to be bound by theory, it is believed that as the tenacity ratio MD:CD of the nonwoven composite article approaches 1, the durability of the composite article is increased, providing superior resistance to breakdown of the nonwoven when stress is applied to the nonwoven during use. Further, without intending to be bound by theory, it is believed that the MD:CD ratio of a composite article including at least one layer of a melt-spun nonwoven web will have an MD:CD ratio closer to 1:1 than an identical composite article except including all carded layers.

The basis weights of the nonwoven composite articles of the disclosure are not particularly limiting and can be in a range of about 5 $g/m^2$ to about 150 $g/m^2$, about 5 $g/m^2$ to about 125 $g/m^2$, about 5 $g/m^2$ to about 100 $g/m^2$, about 5 $g/m^2$ to about 70 $g/m^2$, about 5 $g/m^2$ to about 50 $g/m^2$, about 5 $g/m^2$ to about 30 $g/m^2$. In embodiments, the nonwoven composite articles of the disclosure can have a basis weight of about 5 $g/m^2$ to about 50 $g/m^2$. In embodiments, the nonwoven composite articles of the disclosure can have a basis weight of about 50 $g/m^2$ to about 150 $g/m^2$. In embodiments, the first layer of nonwoven web can have a basis weight of about 30 $g/m^2$ to about 70 $g/m^2$ and the nonwoven composite article can have a basis weight of about 60 $g/m^2$ to about 150 $g/m^2$. In embodiments, the first layer of nonwoven web can have a basis weight of about 5 $g/m^2$ to about 15 $g/m^2$. In embodiments, the first layer of nonwoven web can have a basis weight of about 5 $g/m^2$ to about 15 $g/m^2$ and the nonwoven composite article can have a basis weight in a range of about 15 $g/m^2$ to about 50 $g/m^2$. In embodiments, the third layer of nonwoven web can have a basis weight of about 5 $g/m^2$ to about 15 $g/m^2$. In embodiments, the first layer of nonwoven web can have a basis weight of about 5 $g/m^2$ to about 15 $g/m^2$ and the third layer of nonwoven web can have a basis weight of about 5 $g/m^2$ to about 15 $g/m^2$. In embodiments, the second layer of nonwoven web can be included in the composite article in about 2.5 wt. % to about 10 wt. %, based on the total weight of the composite article. In embodiments, the second layer of nonwoven web can be included in the composite article in about 2.5 wt. % to about 10 wt. %, based on the total weight of the composite article and the first layer of nonwoven web can be included in the composite article in about 90 wt. % to about 97.5 wt. %, based on the total weight of the composite article. In embodiments, the second layer of nonwoven web can be included in the composite article in about 2.5 wt. % to about 10 wt. %, based on the total weight of the composite article and the first layer of nonwoven web and the third layer of nonwoven web together are included in an about 90 wt. % to about 97.5 wt. %, based on the total weight of the composite article. In embodiments, the third layer of nonwoven web can be included in the composite article in about 2.5 wt. % to about 10 wt. %, based on the total weight of the composite article and the first layer of nonwoven web and second layer of nonwoven web together are included in about 45 wt. % to about 48 wt. %, based on the total weight of the composite article.

In embodiments, the fiber diameters of the first plurality of fibers can be substantially uniform. In embodiments, the fiber diameters of the second plurality of fibers can be substantially uniform. In embodiments, the fiber diameters of the third plurality of fibers can be substantially uniform. In embodiments, the fiber diameters of the first plurality of fibers and third plurality of fibers can be substantially uniform. In embodiments, the fiber diameters of each of the first plurality of fibers, second plurality of fibers, and third plurality of fibers can be substantially uniform.

In embodiments, the nonwoven composite article can have an improved modulus, tensile strength, elongation, tenacity, or a combination thereof in the machine direction, cross direction, or both, relative to an identical article comprising only the first layer. In embodiments, the non-woven composite article can have an improved modulus, tensile strength, elongation, tenacity, or a combination thereof in the machine direction, relative to an identical article comprising only the first layer. In embodiments, the nonwoven composite article can have an improved modulus, tensile strength, elongation, or a combination thereof in the cross direction, relative to an identical article comprising only the first layer. In embodiments, the nonwoven composite article can have an improved modulus, tensile strength, elongation, tenacity or a combination thereof in the machine direction and the cross direction, relative to an identical article comprising only the first layer.

Methods of Preparing Composite Articles

In general, the composite articles can be made using any process known in the art suitable for combining two or more layers of nonwoven webs such that at least a portion of the first layer and a portion of the second layer are fused, thereby forming an interface.

In embodiments, the method of forming the nonwoven composite articles of the disclosure can include the steps of:

(a) depositing on a first layer including a first nonwoven web, a second layer comprising a second nonwoven web under conditions sufficient to fuse at least a portion of the first nonwoven web to at least a portion of the second nonwoven web, thereby forming a first interface; and (b) optionally, depositing on the second layer comprising the second nonwoven web, the third layer comprising the third nonwoven web under conditions sufficient to fuse at least a second portion of the second nonwoven web to at least a portion of the third nonwoven web, thereby forming a second interface.

In embodiments, steps (a) and (b) can be repeated to include additional nonwoven layers to the composite structure, e.g., a fourth nonwoven layer, a fifth nonwoven layer, etc.

In general, the conditions sufficient to fuse at least a portion of the first nonwoven web to at least a portion of the second nonwoven web and/or to fuse at least a second portion of the second nonwoven web to at least a portion of the third nonwoven web can include thermal fusion and/or solvent fusion, as described herein.

In embodiments of the foregoing methods, the first layer can comprise a carded nonwoven web. In embodiments of the foregoing methods, the third layer can comprise a carded nonwoven web or a melt-spun nonwoven web. In embodiments of the foregoing methods, the second layer can include a melt-spun nonwoven web or an airlaid nonwoven web. In embodiments, the first layer can include a carded nonwoven web, the second layer can include a melt-spun nonwoven web, and the third layer can include a carded nonwoven web. In embodiments, the first layer can include a carded nonwoven web, the second layer can include a melt blown nonwoven web, and the third layer can include a carded nonwoven web. In embodiments, the second layer can include an airlaid nonwoven web. In embodiments, the first layer can include a carded nonwoven web, the second layer can include an airlaid nonwoven web, and the third layer can include a melt-spun nonwoven web. In embodiments, the first layer can include a carded nonwoven web, the second layer can include an airlaid nonwoven web, and the third layer can include a melt blown nonwoven web. In embodiments, the nonwoven composite article can include five layers of nonwoven web wherein the first layer can include a carded nonwoven web, the second layer can include an airlaid nonwoven web, the third layer can include a melt-spun nonwoven web, the fourth layer can include an airlaid nonwoven web, and the fifth layer can included a carded nonwoven web. In embodiments, the nonwoven composite article can include five layers of nonwoven web wherein the first layer can include a carded nonwoven web, the second layer can include an airlaid nonwoven web, the third layer can include a melt blown nonwoven web, the fourth layer can include an airlaid nonwoven web, and the fifth layer can included a carded nonwoven web. In embodiments, the second nonwoven web can include a cellulose fiber forming material.

Flushable Wipes

Flushable wipes of the disclosure can include a nonwoven web of the disclosure and/or a composite article according to the disclosure.

Flushable wipes can include a plurality of fibers of the disclosure, wherein the plurality of fibers can include water soluble fibers and, optionally, water-insoluble fibers.

In embodiments wherein the flushable wipe includes a nonwoven web comprising water-soluble fibers and water-insoluble fibers, the ratio of water-insoluble fiber to water-soluble fiber can range from about 1:18 to about 4:1, about 1:10 to about 3:1, about 1:5 to about 2:1, or about 1:2 to about 2:1, for example about 1:18, 1:16, 1:14, 1:12, 1:10, 1:5, 1:3, 1:2, 1:1, 2:1, 3:1, or 4:1.

The flushable wipes of the disclosure can include a cleaning lotion. Flushable wipes of the disclosure generally include fibers having a surface energy that is high enough to allow the fibers to be readily wet by the cleaning lotion during the wetting step of the wipe manufacturing process. Thus, in embodiments, at least a portion of at least one exterior layer of the nonwoven composite article of the flushable wipe includes a hydrophilic fiber. In embodiments, at least a portion of each exterior layer of the nonwoven composite article used to prepare the flushable wipe includes a hydrophilic fiber. As used herein, and unless specified otherwise, a "hydrophilic fiber" refers to any fiber having a surface thereof that is hydrophilic. A fiber can have a hydrophilic surface when the fiber includes, for example, a hydrophilic fiber forming material, the fiber is a core-sheath type bicomponent fiber including a hydrophilic fiber forming material in the sheath, and/or the fiber has been surface treated to include a hydrophilic material on the surface thereof. Without intending to be bound by theory, it is believed that a hydrophilic fiber of a nonwoven can facilitate capillary action/wicking of a liquid from a surface of the nonwoven, providing improved liquid acquisition relative to an identical nonwoven that does not include a hydrophilic fiber.

Non-limiting examples of applications for wipes include cleaning surfaces, cleaning skin, automotive uses, baby care, feminine care, hair cleansing, and removing or applying makeup, skin conditioners, ointments, sun-screens, insect repellents, medications, varnishes or industrial and institutional cleaning.

Lotion Composition

The flushable wipes of the disclosure can comprise a lotion composition to wet a substrate to facilitate cleaning. In embodiments wherein the flushable wipe is a personal care wipe, the lotion composition may also include ingredients to soothe, soften, or care for the skin, to improve the feel of the lotion, to improve the removal of residues from the skin, to provide pleasant scents, and/or to prevent bacterial growth, for example.

Lotion compositions can have a pH at or near about 5.5, close to the physiological skin pH. Low pH lotion compositions can have a pH at or near about 3.8 and can be useful in cases where a wipe is being used to remove alkaline residues, such as residues from fecal matter, and help restore a healthy acidic skin pH of approximately 5 and/or render irritants from fecal matter non-irritating, as by inactivating fecal enzymes. Low pH lotions may also inhibit microbial growth. In embodiments wherein the pH of the lotion composition is about 4 or less, the fibers of the first plurality of fibers, second plurality of fibers, and/or third plurality of fibers can include a polyvinyl alcohol copolymer. The copolymer can be provided as the sole fiber forming material in a fiber of a fiber blend or as one component of a fiber forming material in a fiber including a blend of fiber forming materials. In refinements of the foregoing embodiment, the fibers can include a blend of polyvinyl alcohol copolymers and homopolymers. The polyvinyl alcohol copolymers and homopolymers can be provided in a ratio of about 1:1 to about 4:1. In further refinements of the foregoing embodiments, the polyvinyl alcohol copolymer containing fibers can be blended with non-water-soluble fibers.

Lotion compositions can comprise a superwetter, a rheology modifier, an emollient and/or an emulsifier. The superwetter can be present in an amount of about 0.01% to 0.2% by weight of the superwetter to the total weight of the lotion composition. The superwetter can be selected from the group consisting of trisiloxanes, polyether dimethicones wherein the polyether functionality is PEG, PPG, or a mixture thereof, and a mixture of the foregoing.

The rheology modifier can be present in an amount of about 0.01% to 0.5% by weight of the rheology based on the total weight of the lotion composition. The rheology modifier can be selected from the group consisting of xanthan gum, modified xanthan gum, and a combination thereof.

The emollient, if present, may be a thickening emollient. Suitable emollients include, but are not limited to, PEG-10 sunflower oil glycerides, sunflower oil, palm oil, olive oil, emu oil, babassu oil, evening primrose oil, palm kernel oil, cod liver oil, cottonseed oil, jojoba oil, meadowfoam seed oil, sweet almond oil, canola oil, soybean oil, avocado oil, safflower oil, coconut oil, sesame oil, rice bran oil, grape seen oil, mineral oil, isopropyl stearate, isostearyl isononanoate, diethylhexyl fumarate, diisostearyl malate, triisocetyl citrate, stearyl stearate, methyl palmitate, methylheptyl isostearate, petrolatum, lanolin oil and lanolin wax, long chain alcohols like cetyl alcohol, stearyl alcohol, behenyl alcohol, isostearyl alcohol, and 2-hexyl-decanol, myristyl alcohol, dimethicone fluids of various molecular weights and mixtures thereof, PPG-15 stearyl ether (also known as arlatone E), shea butter, olive butter, sunflower butter, coconut butter, jojoba butter, cocoa butter, squalene and squalene, isoparaffins, polyethylene glycols of various molecular weights, polypropylene glycols of various molecular weights, or mixtures thereof.

The emulsifier, if present, may be solid at room temperature. Suitable emulsifiers include, but are not limited to, laureth-23, ceteth-2, ceteth-10, ceteth-20, ceteth-21, ceteareth-20, steareth-2, steareth-10, steareth-20, oleth-2, oleth-10, oleth-20, steareth-100, steareth-21, PEG-40 sorbitan peroleate, PEG-8 stearate, PEG-40 stearate, PEG-50 stearate, PEG-100 stearate, sorbitan laurate, sorbitan palmitate, sorbitan stearate, sorbitan tristearate, sorbitan oleate, sorbitan trioleate, polysorbate 20, polysorbate 21, polysorbate 40, polysorbate 60, polysorbate 61, polysorbate 65, polysorbate 80, polysorbate 81, polysorbate 85, PEG-40 hydrogenated castor oil, citric acid ester, microcrystalline wax, paraffin wax, beeswax, carnauba wax, ozokerite wax, cetyl alcohol, stearyl alcohol, cetearyl alcohol, myristyl alcohol, behenyl alcohol, and mixtures thereof.

In embodiments, the cleaning lotion includes an aqueous emulsion including an emollient and an emulsifier.

The cleaning lotion can further comprise humectants including, but not limited to glycerin, propylene glycol, and phospholipids; fragrances such as essential oils and perfumes as described herein; preservatives; enzymes; colorants; oil absorbers; pesticides; fertilizer; activators; acid catalysts; metal catalyst; ion scavengers; detergents; disinfectants; surfactants; bleaches; bleach components; and fabric softeners. In embodiments, the cleaning lotion includes a fragrance, preservative, enzyme, colorant, oil absorber, pesticide, ion scavenger, detergent, disinfectant, or a combination thereof.

Preservatives prevent the growth of micro-organisms in the liquid lotion, the flushable wipe, and/or the substrate on which the wipe is used. Preservatives can be hydrophobic or hydrophilic. Suitable preservatives include, but are not limited to parabens, such as methyl parabens, propyl parabens, alkyl glycinates, iodine derivatives and combinations thereof.

The lotion load can be between 150% and 480%. As used herein, "load" refers to combining a nonwoven web or composite article with a lotion composition, i.e., a lotion composition is loaded onto or into a nonwoven web or composite article, without regard to the method used to combine the nonwoven web or composite article with the lotion composition, i.e., immersion, spraying, kissrolling, etc. A "lotion load" refers to the amount of lotion loaded onto or into a nonwoven web or composite article, and is expressed as weight of the lotion to weight of the dry (unloaded) nonwoven web or composite article, as a percentage. It may be desirable for the flushable wipe to be loaded with lotion to a degree that some of the lotion can be easily transferred to a substrate (e.g., skin or another surface to be cleaned) during use. The transfer may facilitate cleaning, provide a pleasant sensation for a user (such as a smooth skin feeling or coolness from evaporation), and/or allow for the transfer of compounds to provide beneficial functions on substrate.

The flushable wipes can be nonwoven webs or composite articles having a high density of interstitial spaces between the fibers making up the wipe. In order to maintain enough lotion available on the surface of a wipe to transfer to the substrate, much of the interstitial space in the wipe can be filled with lotion. The lotion in the interstitial space may not be readily available for transfer to a substrate, such that excess lotion can be loaded into the wipe in an amount sufficient to signal to the user that the lotion is available for transfer to a substrate, for example, by providing an adequate sense of wetness. Advantageously, nonwoven composite articles used in the flushable wipes can have a gradient of porosity as described herein, which can facilitate loading of the lotion to the wipe.

The flushable wipe can be made by wetting a nonwoven web or composite article with at least 1 gram of liquid cleaning lotion per gram of dry fibrous composite. Suitable methods of delivering the cleaning lotion to the nonwoven web or composite article include but are not limited to submersion, spraying, padding, extrusion coating and dip coating. After wetting, the wetted composite article can be folded, stacked, cut to length, and packaged as desired. The flushable wipes are generally of sufficient dimension to allow for a convenient handling while being small enough to be easily disposed to the sewage system. The wetted composite article can be cut or folded to such dimensions during the manufacturing process or can be larger in size and having a means such as perforations to allow individual wipes to be separated from the web, in a desired size, by a user.

In embodiments, the flushable wipes of the disclosure comprise a nonwoven web of the disclosure and a cleaning lotion. In embodiments, the flushable wipes of the disclosure comprise a nonwoven composite article of the disclosure and a cleaning lotion. In embodiments, the flushable wipes of the disclosure consist of a nonwoven composite article of the disclosure and a cleaning lotion.

Absorbent Articles

The nonwoven webs and nonwoven composite articles of the disclosure can be used as a liquid acquisition layer for absorbent articles. The absorbent articles can include bibs, breast pads, care mats, cleaning pads (e.g., floor cleaning pads), diapers, diaper pants, incontinence liners, pads, and other articles (e.g., adult incontinence diapers, adult incontinence pads, adult incontinence pants, potty training liners, potty training pads, potty training pants, and pet training pads e.g., puppy pads), interlabial devices, menstrual pads, panty liners, sanitary napkins, tampons, spill absorbing mats, spill absorbing pads, spill absorbing rolls, wound dressings, and the like. In one aspect, any of the foregoing articles can be disposable items. The term "disposable" refers to articles which are designed or intended to be discarded after a single use. That is, disposable articles are not intended to be laundered or otherwise restored or reused, and in embodiments may be incapable of laundering, restoration or reuse.

As used herein, the term "absorbent article" includes articles which absorb and contain liquids such as body exudates. The term "absorbent article" is intended to include diapers, incontinent articles, sanitary napkins, and the like. The term "incontinent articles" is intended to include pads, undergarments (pads held in place by a suspension system of some type, such as a belt, or the like), inserts for absorbent articles, capacity boosters for absorbent articles, briefs, bed pads, and the like, regardless of whether they be worn by adults or other incontinent persons. At least some of such absorbent articles are intended for the absorption of body liquids, such as menses or blood, vaginal discharges, urine, sweat, breast milk, and fecal matter.

As used herein "diapers" refers to devices which are intended to be placed against the skin of a wearer to absorb and contain the various exudates discharged from the body. Diapers are generally worn by infants and incontinent persons about the lower torso so as to encircle the waist and legs of the wearer. Examples of diapers include infant or adult diapers and pant-like diapers such as training pants. "Training pant", as used herein, refers to disposable garments having a waist opening and leg openings designed for infant or adult wearers. A pant may be placed in position on the wearer by inserting the wearer's legs into the leg openings and sliding the pant into position about a wearer's lower torso. A pant may be pre-formed by any suitable technique including, but not limited to, joining together portions of the article using refastenable and/or non-refastenable bonds (e.g., seam, weld, adhesive, cohesive bond, fastener, etc.). A pant may be pre-formed anywhere along the circumference of the article (e.g., side fastened, front waist fastened).

Absorbent articles of the disclosure will typically comprise a liquid pervious topsheet, a liquid impervious backsheet joined to the topsheet, and a liquid acquisition layer and an absorbent core between the topsheet and backsheet. In embodiments wherein the absorbent article is a wearable article (e.g., incontinent articles, sanitary napkins, and the like), the article can have a wearer facing side and an outer facing side. In general, the liquid pervious topsheet is on the wearer facing side and the liquid impervious backsheet is on the outer facing side of the absorbent article. The absorbent core is generally a sheet like structure and, when provided as a wearable, has a wearer facing side and an outer facing side.

In general, the liquid pervious topsheet can be any liquid pervious topsheet known in the art. For a wearable article, the topsheet can be fully or partially elasticized or can be foreshortened to provide a void space between the topsheet and the absorbent core. In general, the liquid impervious backsheet can be any liquid impervious backsheet known in the art. The backsheet prevents exudates absorbed by the absorbent core and contained within the article form contacting any substrate the absorbent article may be in contact with. The backsheet can be impervious to liquids and include a laminate of a nonwoven and a thin plastic film, such as a thermoplastic film. Suitable backsheet films include those manufactured by Tredegar Industries Inc. of Terre Haute, Ind. and sold under the trade names X15306, X10962, and X10964. Other suitable backsheet materials can include breathable materials that permit vapors to escape from the absorbent article, while still preventing liquid from passing through the backsheet. Exemplary breathable materials can include materials such as woven webs, nonwoven webs, and composite materials such as manufactured by Mitsui Toatsu Col, of Japan under the designation ESPOIR NO and by EXXON Chemical Co., of Bay City, Tex., under the designation EXXAIRE.

The absorbent core is disposed between the topsheet and the backsheet. The absorbent core can comprise any absorbent material that is generally capable of absorbing and retaining liquids such as urine and other body exudates. The absorbent core can include a wide variety of liquid-absorbent materials commonly used in disposable diapers and other absorbent articles such as super absorbent polymer, comminuted wood pulp (air felt), creped cellulose wadding; absorbent foams, absorbent sponges, absorbent gelling materials, or any other known absorbent material or combinations of materials. The absorbent core can include minor amounts (less than about 10%) of non-liquid absorbent materials, such as adhesives, waxes, oils and the like.

In general, the liquid acquisition layer includes a nonwoven web of the disclosure including a plurality of fibers including a water-soluble polyvinyl alcohol fiber forming material. The plurality of fibers can include a single fiber type or a blend of fiber types, and the fibers can include a sole polyvinyl alcohol fiber forming material or a blend of fiber forming materials including a polyvinyl alcohol fiber forming material.

In embodiments, the liquid acquisition layer can be provided between the absorbent core and the topsheet. In wearable embodiments, the liquid acquisition layer can be provided on the wearer facing side of the absorbed core. In embodiments, the liquid acquisition layer can be provided between the absorbent core and the backsheet. In wearable embodiments, the liquid acquisition layer can be provided on the outer facing side of the absorbent core. In embodiments, the liquid acquisition layer is wrapped around the absorbent core. The liquid acquisition layer can be a single sheet that is wrapped around the absorbent core or can be provided as two individual layers that are joined. Without intending to be bound by theory, it is believed that by including the liquid acquisition layer between the absorbent core and the backsheet or on the outer facing side of the absorbent core advantageously prevents leakage of the liquid from the absorbent article by providing additional liquid acquisition material to catch any overflow of liquid from the topsheet side and/or wearer facing side.

In general, the liquid acquisition layer can be directly in contact with the absorbent core, there can include a space between the absorbent core and the liquid acquisition layer, or there can include an intervening layer between the absorbent core and the liquid acquisition layer. In embodiments, the liquid acquisition layer is in contact with the absorbent core. In embodiments, the absorbent article includes an intervening layer provided between the acquisition layer and the absorbent core. In embodiments, the liquid acquisition layer is in contact with the absorbent core on the topsheet side/wearer facing side and an intervening layer is provided between the acquisition layer and the absorbent core on the backsheet side/outer facing side. In embodiments, the liquid acquisition layer is in contact with the absorbent core on the backsheet side/outer facing side and an intervening layer is provided between the acquisition layer and the absorbent core on the topsheet side/wearer facing side. The intervening layer can be, for example, a second liquid pervious layer or liquid acquisition layer included to help facilitate spread of the liquid from the point of deposition to cover the full area of the absorbent core.

In embodiments, the absorbent article includes a liquid acquisition layer that is a nonwoven web of the disclosure. In embodiments, the wearable absorbent article includes a liquid acquisition layer that is a nonwoven web of the disclosure. In embodiments, the absorbent article includes a liquid acquisition layer that is a nonwoven composite article of the disclosure. In embodiments, the wearable absorbent article includes a liquid acquisition layer that is a nonwoven composite article of the disclosure.

Dissolution and Disintegration Test (MSTM-205)

A nonwoven web, water-soluble film, or laminate structure can be characterized by or tested for Dissolution Time and Disintegration Time according to the MonoSol Test Method 205 (MSTM 205), a method known in the art. See, for example, U.S. Pat. No. 7,022,656. The description provided below refers to a nonwoven web, while it is equally applicable to a water-soluble film or laminate structure.

Apparatus and Materials Include:
- 600 mL Beaker,
- Magnetic Stirrer (Labline Model No. 1250 or equivalent),
- Magnetic Stirring Rod (5 cm),
- Thermometer (0 to 100° C.±1° C.),
- Template, Stainless Steel (3.8 cm×3.2 cm),
- Timer (0-300 seconds, accurate to the nearest second),
- Polaroid 35 mm slide Mount (or equivalent),
- MonoSol 35 mm Slide Mount Holder (or equivalent), and
- Distilled water.

For each nonwoven web to be tested, three test specimens are cut from a nonwoven web sample that is a 3.8 cm×3.2 cm specimen. Specimens should be cut from areas of web evenly spaced along the traverse direction of the web. Each test specimen is then analyzed using the following procedure.

Lock each specimen in a separate 35 mm slide mount.

Fill beaker with 500 mL of distilled water. Measure water temperature with thermometer and, if necessary, heat or cool water to maintain the temperature at the temperature for which dissolution is being determined, e.g., 20° C. (about 68° F.).

Mark height of column of water. Place magnetic stirrer on base of holder. Place beaker on magnetic stirrer, add magnetic stirring rod to beaker, turn on stirrer, and adjust stir speed until a vortex develops which is approximately one-fifth the height of the water column. Mark depth of vortex.

Secure the 35 mm slide mount in the alligator clamp of the 35 mm slide mount holder such that the long end of the slide mount is parallel to the water surface. The depth adjuster of the holder should be set so that when dropped, the end of the clamp will be 0.6 cm below the surface of the water. One of the short sides of the slide mount should be next to the side of the beaker with the other positioned directly over the center of the stirring rod such that the nonwoven web surface is perpendicular to the flow of the water.

In one motion, drop the secured slide and clamp into the water and start the timer. Rupture occurs when the sample has become compromised within the slide, for example, when a hole is created. Disintegration occurs when the nonwoven web breaks apart and no sample material is left in the slide. When all visible nonwoven web is released from the slide mount, raise the slide out of the water while continuing to monitor the solution for undissolved nonwoven web fragments. Dissolution occurs when all nonwoven web fragments are no longer visible and the solution becomes clear. Rupture and dissolution can happen concurrently for nonwoven samples wherein the fibers are prepared from polyvinyl alcohol having a low degree of hydrolysis (e.g., about 65-88%). Dissolution times are recorded independently of rupture times when there is a 5 second or greater difference between rupture and dissolution.

Thinning time can also be determined using MSTM-205. Thinning of a nonwoven web occurs when some of the fibers making up the nonwoven web dissolve, while other fibers remain intact. The thinning of the web occurs prior to disintegration of the web. Thinning is characterized by a decrease in opacity, or increase in transparency, of the nonwoven web. The change from opaque to increasingly transparent and can be visually observed. During MSTM-205, after the secured slide and clamp have been dropped into the water the opacity/transparency of the nonwoven web is monitored. At the time point wherein no change in opacity/transparency is observed (i.e., the web does not become any less opaque or more transparent), the time is recorded as the thinning time.

The results should include the following: complete sample identification; individual and average disintegration and dissolution times; and water temperature at which the samples were tested.

Method for Determining Single Fiber Solubility

The solubility of a single fiber can be characterized by the water breaking temperature. The fiber breaking temperature can be determined as follows. A load of 2 mg/dtex is put on a fiber having a fixed length of 100 mm. Water temperature starts at 1.5° C. and is then raised by 1.5° C. increments every 2 minutes until the fiber breaks. The temperature at which the fiber breaks is denoted as the water breaking temperature.

The solubility of a single fiber can also be characterized by the temperature of complete dissolution. The temperature of complete dissolution can be determined as follows. 0.2 g of fibers having a fixed length of 2 mm are added to 100 mL of water. Water temperature starts at 1.5° C. and is then raised by 1.5° C. increments every 2 minutes until the fiber completely dissolves. The sample is agitated at each temperature. The temperature at which the fiber completely dissolves in less than 30 seconds is denoted as the complete dissolution temperature.

Diameter Test Method

The diameter of a discrete fiber or a fiber within a nonwoven web is determined by using a scanning electron microscope (SEM) or an optical microscope and an image analysis software. A magnification of 200 to 10,000 times is chosen such that the fibers are suitably enlarged for measurement. When using the SEM, the samples are sputtered with gold or a palladium compound to avoid electric charging and vibrations of the fiber in the electron beam. A manual procedure for determining the fiber diameters is used from the image (on monitor screen) taken with the SEM or the optical microscope. Using a mouse and a cursor tool, the edge of a randomly selected fiber is sought and then measured across its width (i.e., perpendicular to the fiber direction at that point) to the other edge of the fiber. A scaled and calibrated image analysis tool provides the scaling to get an actual reading in microns. For fibers within a nonwoven web, several fibers are randomly selected across the sample of nonwoven web using the SEM or the optical microscope. At least two portions of the nonwoven web material are cut and tested in this manner. Altogether at least 100 such measurements are made and then all data are recorded for statistical analysis. The recorded data are used to calculate average (mean) of the fibers, standard deviation of the fibers, and median fiber diameters.

Tensile Strength, Modulus, and Elongation Test

A nonwoven web, water-soluble film, or laminate structure characterized by or to be tested for tensile strength according to the Tensile Strength (TS) Test, modulus (or tensile stress) according to the Modulus (MOD) Test, and elongation according to the Elongation Test is analyzed as follows. The description provided below refers to a nonwoven web, while it is equally applicable to a water-soluble film or laminate structure. The procedure includes the determination of tensile strength and the determination of modulus at 10% elongation according to ASTM D 882 ("Standard Test Method for Tensile Properties of Thin Plastic Sheeting") or equivalent. An INSTRON tensile testing apparatus (Model 5544 Tensile Tester or equivalent) is used for the collection of nonwoven web data. A minimum of three test specimens, each cut with reliable cutting tools to ensure dimensional stability and reproducibility, are tested in the machine direction (MD) (where applicable) for each measurement. Tests are conducted in the standard laboratory atmosphere of 23±2.0° C. and 35±5% relative humidity. For tensile strength or modulus determination, 1"-wide (2.54 cm) samples of a nonwoven web are prepared. The sample is then transferred to the INSTRON tensile testing machine to proceed with testing while minimizing exposure in the 35% relative humidity environment. The tensile testing machine is prepared according to manufacturer instructions, equipped with a 500 N load cell, and calibrated. The correct grips and faces are fitted (INSTRON grips having model number 2702-032 faces, which are rubber coated and 25 mm wide, or equivalent). The samples are mounted into the tensile testing machine and analyzed to determine the 100% modulus (i.e., stress required to achieve 100% film elongation), tensile strength (i.e., stress required to break film), and elongation % (sample length at break relative to the initial sample length). In general, the higher the elongation % for a sample, the better the processability characteristics for the nonwoven web (e.g., increased formability into packets or pouches).

Determination of Basis Weight

Basis weight is determined according to ASTM D3776/D3776M-09a (2017). Briefly, a nonwoven specimen having an area of at least 130 cm$^2$ or a number of smaller die cut specimens taken from different locations in the sample and having a total area of at least 130 cm$^2$ are cut. The specimen(s) are weighed to determine mass on a top loading analytical balance with a resolution of ±0.001 g. The balance is protected from air drafts and other disturbances using a draft shield. Specimens of fabric may be weighed together. The mass is calculated in ounces per square yard, ounces per linear yard, linear yards per pound, or grams per square meter to three significant figures.

Determination of Moisture Vapor Transmission Rate

Moisture Vapor Transmission Rate (MVTR) is determined according to MSTM-136. The MVTR defines how much moisture per day moves through a sample. The description provided below refers to a nonwoven web, while it is equally applicable to a water-soluble film or laminate structure.

Apparatus and Materials Include:
Permatran-W Model 3/34 (or equivalent),
Compressed Gas Cylinder of Nitrogen (99.7% or above),
Regulator-Tee (part number 027-343),
Main Line Supply regulator,
HPLC Grade Water (or equivalent),
10 cc Syringe with Luerlok Tip (part number 800-020),
Powder-free gloves,
High vacuum grease (part number 930-022),
(2) Test Cells,
Cutting template,
Cutting board,
Razor blade with handle, and
Cut-resistant glove.

Preparation of the Permatran W-Model 3/34: Make sure nitrogen pressure level is above 300 psi, the pressure on the carrier gas regulator-tee reads 29 psi (must not exceed 32 psi) and the main line supply regulator pressure is set to 35 psi. Open the door on the instrument panel to access humidifier to check the water level. If water level is low, fill a syringe with HPLC-grade water and insert the luer fitting on the syringe into the "fill Port" for the reservoir. Open the "Fill Valve" by turning it 2-3 turns counterclockwise then push in the plunger on the syringe to force the water into the reservoir. Close the 'Fill Valve' and remove syringe. Note: do not allow water level to exceed line marked adjacent to reservoir.

Preparation and Testing of Samples: For each nonwoven web to be tested, take the sample web and lay it flat on the cutting board. Place the template on top of the web and use the razor blade with a handle to cut out the sample. Make sure cut-resistant glove is worn when cutting the sample out. Set the sample aside. Grease around the sealing surfaces of the test cell's top piece with high vacuum grease. Mount the film sample on top of the test cell's top piece. Note: Orientation can be important. If a homogeneous material, orientation is not critical. If a multi-layered and laminated material, place the multilayered film or laminate with barrier coating or laminate up, towards the top of the cell. For example, a one-side, wax coated PVOH web should be mounted with the wax side up, placing the wax towards the carrier gas (Nitrogen). Place the test cell's top piece on top of the test cell's bottom piece. Make sure the test cell is clamped together with a good seal. Press the cell load/unload button to open cell tray. Grasp the test cell by the front and back edges and lower it straight down. Close the cell tray completely by gently pushing straight towards panel. Press the cell load/unload button to clamp the cell. Note: You should hear a click. Repeat for second sample.

After the samples are loaded and the instrument is ready, the test parameters must be set. Note: There are two types of test parameters, cell parameters and instrument parameters. Cell parameters are specific to each cell while instrument parameters are common for all cells. Touch the "Test Button" on the screen. Under "Auto Test" select "Tab A". Touch "Cell Tab". Fill out the following by touching each bubble: ID, Area ($cm^2$), Thickness (mil). Note: Area of template is 50 $cm^2$. Repeat for "Tab B". Touch "Instrument Tab". Fill out the following by touching each bubble: Cell Temp (° C.) and Test Gas RH (%). Note: Make sure 100% RH is set to off. Cell temperature can be set to a minimum of 10° C. to maximum of 40° C. Test Gas RH can be set to minimum 5% to 90%. If 100% RH is needed, it requires a different method. Repeat for "Tab B". Once the test parameters are set, select "Start Selected" or "Start All" depending on sample number. Note: The indicator light for each cell on front panel will be green indicating the start of test.

Surface Resistivity Measurements

Surface resistivity of nonwoven webs and films can be measured according to ASTM D257.

Softness Rating

The hand feel of a nonwoven web or pouch of the disclosure is related to the softness of the sample and can be evaluated using relative testing methods. A tester carrying out the softness evaluation uses clean hands to feel the samples in whatever manner or method the individual chose, to determine a softness rating for the nonwoven webs and articles of the disclosure as compared to a control material comprising a nonwoven web consisting of fibers consisting of polyvinyl alcohol homopolymers having a degree of hydrolysis of 88%, the fibers having a 2.2 dtex/51 mm cut, having a softness rating of 1 (softest) and a control material comprising a nonwoven web consisting of fibers consisting of 75% polyvinyl alcohol homopolymers having a degree of hydrolysis of 88%, the fibers having a 2.2/51 mm cut, and 25% of 22 dtex/38 mm PET fiber, having a softness rating of 5 (roughest/coarsest). The hand panel is a blind study so that the raters are not swayed by their perception of sample names. Samples were rated from 1 to 5.

Flushability Test

The ability of the nonwoven webs and/or laminates of the disclosure to be flushed in a septic or municipal sewage treatment system can be determined according to a modified INDA/EDANA—Criteria for Recognition as a Flushable Product, as provided below. The below test references nonwoven web samples, however it will be understood that the method can also be used for laminate structures.

Equipment and Materials Include:
    Rocking digital platform shaker,
    Two clear, plastic, 12×5×3.9 inch containers,
    Two sieves (12.5 mm apertures),
    Dried nonwoven web samples, and
    100° C. oven.

Parameters Include:
    Rocking platform set to 18 RPM and 11° tilt period,
    1 L tap water per container, and
    30 min testing period.

Testing Procedure:
    1. Place two containers on rocking platform. This method tests two samples at a time.
    2. Measure 1 L of tap water in beaker and pour into one plastic container. Repeat for other container. Make sure tap water in containers is at 15° C.±1° C. before starting test.
    3. Record weight of the initial dried test sample (initial sample mass (g)) and weight of sieves (initial sieve mass (g)) and record independently.
    4. Set appropriate parameters on digital rocking platform.
    5. Place each test sample in their corresponding container and immediately start the agitation process (rocking of the platform),
    6. Once the process is complete (after 30 minutes), take each container and pour through their corresponding sieves. Pouring at a height of 10 cm above sieve plate.
    7. Rinse container into sieve to ensure all of the remaining test sample was removed.
    8. Place sieve in 100° C. oven for 45 minutes to ensure all water evaporates.
    9. Record weight of sieve and remaining test sample together (total final mass (g)).
    10. Calculate the total retained sample mass (final sample mass (g)):

Final sample mass (g)=total final mass (g)−initial sieve mass (g)

11. Calculate the percent (%) disintegration:

% Disintegration=[1−(final sample mass (g)/initial sample mass (g))]×100

12. Make sure sieves are cleaned, dried, and re-weighed before starting next test.
    13. Repeat test until replicate of N=3 is complete for each specific test sample.

A sample is sufficiently flushable to be disposed of by flushing in a septic or municipal sewage treatment system when the sample has a percent disintegration equal to or greater than of at least 20%. In embodiments, the nonwoven webs, laminates, and pouches of the disclosure can have a percent disintegration of at least 20%, at least 30%, at least 35%, at least 40%, at least 45%, at least 50%, at least 55%, at least 60%, at least 65%, at least 70%, at least 75%, at least 80%, at least 85%, at least 90%, or at least 95% as measured by the Flushability Test.

Liquid Release Test

Figure 4:
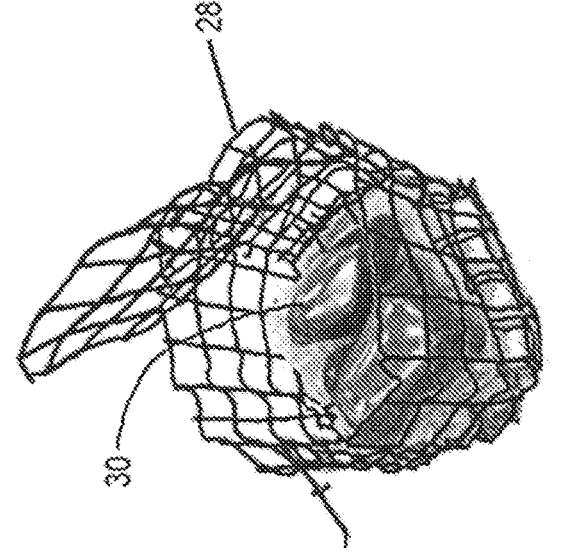
FIG. 4 is an illustration of a wire frame cage (shown with the top open, to better illustrate water-soluble pouches contained therein) for use in the Liquid Release Test described herein.

FIG. 4 is an illustration of a wire frame cage (shown with the top open, to better illustrate water-soluble pouches contained therein) for use in the Liquid Release Test described herein.

Figure 5:
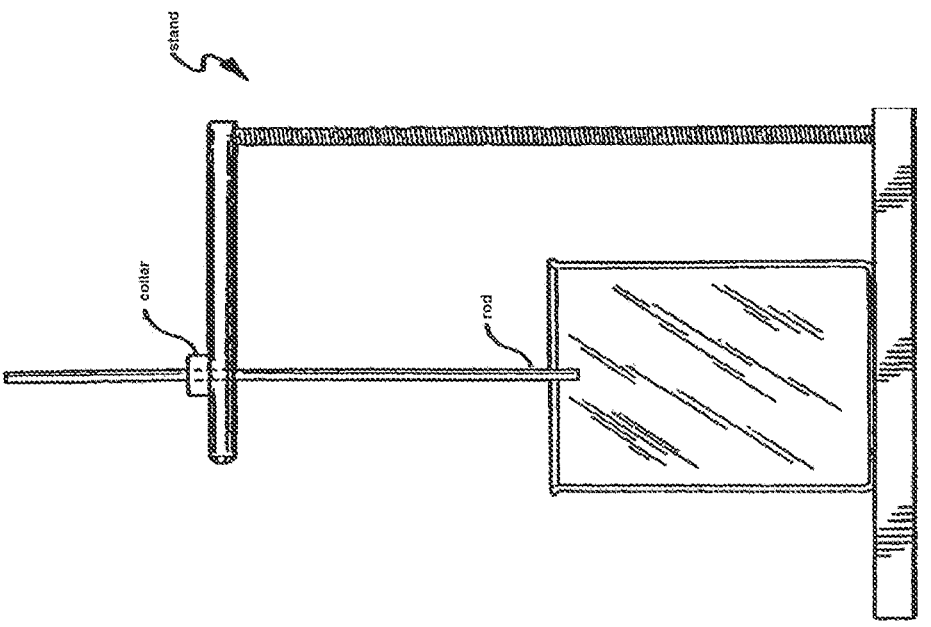
FIG. 5 shows an apparatus for performing the Liquid Release Test, including a beaker resting on a stand, the stand holding a rod for lowering a cage into the beaker, the rod being fixable by a collar with a set screw (not shown).

FIG. 5 shows an apparatus for performing the Liquid Release Test, including a beaker resting on a stand, the stand holding a rod for lowering a cage into the beaker, the rod being fixable by a collar with a set screw (not shown).

A water-soluble nonwoven web, film, and/or pouch characterized by or to be tested for delayed solubility according to the Liquid Release Test is analyzed as follows using the following materials:

2 L beaker and 1.2 liters of deionized (DI) water;

Water-soluble pouch to be tested; the pouch is preconditioned for two weeks at 38° C.; for results to be comparative, all nonwoven webs tested should have the same basis weight and all films tested should have the same thickness, for example, 88 μm or 76 μm;

Thermometer;

Wire cage; and

Timer.

Before running the experiment, ensure that enough DI water is available to repeat the experiment five times, and ensure that the wire cage and beaker are clean and dry.

The wire frame cage is a plastic coated wire cage (4"× 3.5"×2.5") with no sharp edges, or equivalent. The gauge of the wire should be about 1.25 mm and the wire should have openings the size of 0.5 inch (1.27 cm) squares. An example image of a cage 28 with test pouches 30 is shown in FIG. 4.

To set up for the test, carefully place the water-soluble pouch in the cage while not scratching the pouch on the cage and allowing free space for the pouch to move. Do not bind the pouch tightly with the wire cage, while still ensuring it is secure and will not come out of the cage. The orientation of the pouch in the cage should be such that the natural buoyancy of the pouch, if any, is allowed (i.e. the side of the pouch that will float to the top should be placed towards the top). If the pouch is symmetrical, the orientation of the pouch generally would not matter.

Next, fill the 2 L beaker with 1200 milliliters of 20° C. DI water.

Next, lower the wire frame cage with the enclosed pouch into the water. Ensure that the cage is 1 inch (2.54 cm) from the bottom of the beaker. Be sure to fully submerge the pouch on all sides. Ensure that the cage is stable and will not move and start a timer as soon as the pouch is lowered into the water. The position of the cage with respect to the water in the beaker can be adjusted and maintained by any suitable means, for example by using a clamp fixed above the beaker, and a rod attached to the top of the cage. The clamp can engage the rod to fix the position of the cage, and tension on the clamp can be lowered in order to lower the cage into the water. Other means of frictional engagement can be used in the alternative to a clamp, for example a collar with a set screw, as shown in FIG. 5 (set screw not shown). FIG. 5 shows a beaker resting on a stand, the stand holding a rod for lowering a cage (not shown) into the beaker, the rod being able to hold a fixed vertical position by use of a collar having a set screw (not shown) that engages the rod, for example by friction or by engagement with a hole (not shown) in the rod.

Liquid content release is defined as the first visual evidence of the liquid leaving the submerged pouch.

Determination of the Degree of Hydrolysis of a Fiber

Titration Method. The degree of hydrolysis of a fiber can be determined using titration. In particular, a known amount of polyvinyl alcohol fibers are dissolved in 200 mL of deionized water by agitation and heating the mixture at a temperature higher than 70° C. Once all of the PVOH has dissolved, the solution is cooled to room temperature. Once the solution has cooled, 4-5 drops of phenolphthalein indicator solution are added to the PVOH solution, along with 20.0 mL of 0.5N NaOH solution. The solution is mixed and left at room temperature for a minimum of 2 hours. After this time, 20.0 mL of 0.5N sulfuric acid are added to the solution and mixed. The solution is titrated with 0.1N NaOH solution until the endpoint, which is taken as the point at which the solution turns faint pink and maintains this color without returning to a colorless solution for a minimum of 30 seconds. Using the measurements obtained in the aforementioned procedure, the DH of the PVOH is determined via the following calculations $$A_1 = \frac{(V_{sample} - V_{blank}) \times N \times 0.06005}{\text{Wt}_{sample} \times \frac{P}{100}} \times 100$$

$$A_2 = \frac{44.05 \times A_1}{60.05 - (0.42 \times A_1)}$$

$$DH = 100 - A_2$$

where:

A1: residual acetate groups (wt %),

A2: residual acetate groups (mole %),

DH: degree of hydrolysis (mole %),

Vsample: volume of 0.1N NaOH solution added during titration of sample (mL),

Vblank: volume of 0.1N NaOH solution added during titration of blank (mL),

N: certified concentration of standardized 0.1N NaOH solution used in titration step Wtsample: sample mass (g), and P: purity of PVOH sample=100–(volatile matter (wt %)+sodium acetate (wt %)).

FTIR Method. FTIR can be used to determine the degree of hydrolysis of the outer portion of a fiber surface via attenuated total reflectance (ATR). The depth of the fiber which this method measures is dependent on the specific ATR apparatus, in particular, the crystal used. By taking the ratio of the peak heights at ~1730 cm$^{-1}$ (ketone peak, attributed to residual acetate groups) and ~1420 cm$^{-1}$ (reference peak), one can use the equation obtained by plotting the same ratios for PVOH resins against known degrees of hydrolysis to determine the degree of hydrolysis of the unknown sample.

Gradient Test Method. A gradient in the degree of hydrolysis of a fiber can be determined and quantified using cross-section X-ray photoelectron spectroscopy (XPS), depth XPS, NMR techniques, ultraviolet photoelectron spectrometry (UPS), environmental SCM, or Auger electron spectroscopy (AES or SAM).

For XPS analysis, the depth of the fiber which this method measures is dependent on the specific ion beam used during the XPS analysis for depth profiling to determine changes in degree of hydrolysis as a function of cross section. By taking the ratio of the deconvoluted peaks at 287.6 eV and 288.8 eV, representing the carboxyl and carbonyl groups of acetate groups for non-fully hydrolyzed PVOH, to that of 286.5 eV and 532.8 eV, corresponding to the hydroxyl groups of PVOH, one can use the equation obtained by plotting the same ratios for PVOH resins against known degrees of hydrolysis to determine the degree of hydrolysis of the unknown sample. This method can be repeated between ion beam sputtering stages to gain a complete depth profile and change of degree of hydrolysis across the cross-section of the PVOH fibers. XPS methods are described in Gilbert et al "Depth-profiling X-ray photoelectron spectroscopy (XPS) analysis of interlayer diffusion in polyelectrolyte multilay-ers" PNAS, vol. 110, no. 17, 6651-6656 (2013) (available: https://www.pnas.org/content/pnas/1/10/17/6651.full.pdf), and European Polymer Journal 126 (2020) 109544, the entirety of which are hereby incorporated by reference.

AES methods are described in ASTM E984-12, the entirety of which is hereby incorporated by reference.

Measurement of Fiber Shrinkage (%)

A MonoSol Standard Operating Procedure is used to measure a shrinkage of a fiber along a longitudinal axis of the fiber while contacting water at a temperature in a range of from 10° C. to 23° C.

Materials Include:

Fiber samples (approximately 3 grams), 500 mL beaker,

Chilled deionized water (located in a refrigerator),

Deionized water,

Paper clip,

Alligator clamp (solubility stand),

Stir plate, and

Timer.

A sample is prepared through the following steps:

obtain a small bundle of fibers (approximate weight of 0.013 gram (g)-0.015 g) that is not entangled to ensure that the fibers of the small bundle will hold in the paper clip and the alligator clamp;

take a paper clip and pull an end of the fiber through the cross sections of the paper clip; and do so for each fiber that needs to be tested, with a replicate of N=3 for each testing temperature, e.g., 23° C. and 10° C.

Figure 8:
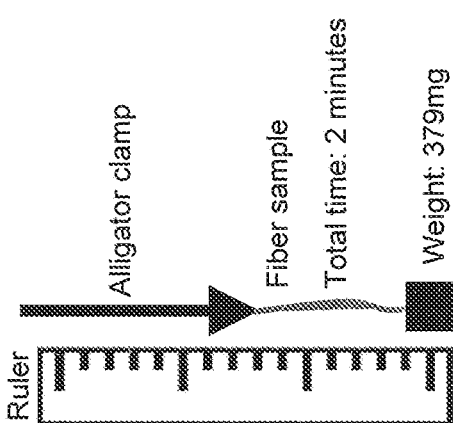
FIG. 8 illustrates an apparatus set-up used for measuring a shrinkage along a longitudinal axis of a fiber with the fiber contacting water at a temperature in a range of from 10° C. to 23° C.

The testing apparatus as shown in FIG. 8 is set up as follows:

fill a 500 mL beaker with 400 mL of water of a respective temperature while the water temperature is checked using a temperature probe before and during testing; and tape a ruler to the top of the alligator clamp such that the ruler hangs parallel to the clamp;

Place the beaker on a stir plate and a solubility stand next to the stir plate, submerging the ruler into the beaker such that a length of the fiber can be read.

The testing procedure includes the following steps:

attach the free end of the paper clipped fiber into the alligator clamp;

submerge the test sample into the beaker so that it's lined up next to the ruler;

start the timer and record the initial length of the fiber. The test sample fiber length is from the end of alligator clip to the top of the paper clip (as shown in FIG. 8);

after two minutes, record the final length of the fiber; and lift the clamp out of the water and remove the sample fiber from the clamp. Be sure to thoroughly dry off the outside and the inside of clamp between each test.

The shrinkage of a fiber is calculated using the following equation:

$$\text{shrinked length} = \text{initial length} - \text{final length}$$

$$\frac{\text{shrinked length}}{\text{initial length}} \times 100\% = \text{fiber shrinkage (\%)}$$

After contacting water, a fiber provided in the present disclosure absorbs water and swells in the traverse cross-section, while displaying a shrinkage in its length along the longitudinal direction.

One or more optional features that can be used individu-ally or in combination are described in the following para-graphs. Optionally, the fiber to be treated is a polyvinyl acetate fiber. Optionally, the fiber to be treated is a polyvinyl alcohol fiber. Optionally, the fiber to be treated is a polyvinyl alcohol fiber comprising a polyvinyl alcohol polymer having a degree of hydrolysis in a range of 79-99%. Optionally, the fiber to be treated is a polyvinyl alcohol fiber comprising a polyvinyl alcohol polymer having a degree of hydrolysis in a range of 88%-96%. Optionally, the fiber to be treated is a polyvinyl alcohol fiber comprising a polyvinyl alcohol poly-mer having a degree of hydrolysis of 88%, 92%, or 96%. Optionally, the fiber to be treated is a polyvinyl alcohol fiber comprising a polyvinyl alcohol copolymer. Optionally, the fiber to be treated is a polyvinyl alcohol fiber comprising an anionically modified comopolymer. Optionally, the fiber to be treated is a polyvinyl alcohol fiber comprising a polyvinyl alcohol copolymer and an anionically modified PVOH copo-lymer.

Optionally, the hydrolysis agent comprises a hydroxide salt selected from the group consisting of sodium hydroxide, potassium hydroxide, ammonium hydroxide, and a combi-nation thereof. Optionally, the hydrolysis agent comprises sodium hydroxide. Optionally, the hydrolysis agent com-prises potassium hydroxide. Optionally, the solvent of the hydrolysis agent solution comprises methanol. Optionally, the solvent of the hydrolysis agent solution comprises methanol and water. Optionally, the solvent of the hydrolysis agent solution comprises DMSO and water. Optionally, the solvent of the hydrolysis agent solution comprises an alco-hol that is a liquid under the treatment conditions.

Optionally, the admixing of the fiber to be treated and the hydrolysis agent solution comprises immersing the fiber in the hydrolysis agent solution. Optionally, the admixing comprises heating the mixture of the fiber and the hydrolysis agent solution. Optionally, the admixing comprises heating the mixture of the fiber and the hydrolysis agent solution to a temperature of about 30° C. to about 60° C. Optionally, the admixing comprises heating the mixture of the fiber and the hydrolysis agent for up to about one hour. Optionally, the admixing comprises heating the mixture of the fiber and the hydrolysis agent for about 1 hour to about 6 hours. Option-ally, the admixing comprises heating the mixture of the fiber and the hydrolysis agent for about 6 hours to about 24 hours.

Optionally, the fiber to be treated can be contacted with the hydrolysis agent solution to increase the degree of hydrolysis of a hydrolyzable polymer of the fiber in a region of the fiber comprising at least the surface of the fiber. Optionally, the contacting can be by immersion. Optionally, the contacting can be by dip-coating. Optionally, the contacting can be by spraying. Optionally, the contacting can be by brushing. Optionally, the contacting can be by rolling.

In some embodiments, the hydrolysis agent solution comprises sodium hydroxide and methanol, the admixing step comprises immersing the fiber in the hydrolysis agent solution, and the mixture of the fiber in the hydrolysis agent solution is heated to a temperature of about 30° C. to 60° C. for about 1 minute to about 24 hours. The fiber comprises a polymer comprising at least one of a vinyl acetate moiety or a vinyl alcohol moiety and having a degree of hydrolysis less than 100% as described herein. For example, in some embodiments, the fiber comprises a copolymer of vinyl alcohol and vinyl acetate having a degree of hydrolysis of 88%, 92%, or 96% or an anionically modified copolymer having a carboxylate or sulfonate modification having a degree of hydrolysis of 88%, 92%, or 96%. The hydrolysis agent solution comprises sodium hydroxide and methanol. The admixing comprises immersing the fiber in the hydrolysis agent solution, and the mixture of the fiber in the hydrolysis agent solution is heated to a temperature of about 30° C. to 60° C. for a time period, for example, from about 12 hours to about 24 hours, or from about 1 hour to about 12 hours, or from about one minute to about 1 hour.

An hydrolysis reaction of a copolymer of vinyl acetate and vinyl alcohol is illustrated in Scheme (1) as follows:

(1)

Such a copolymer is a polyvinyl alcohol copolymer, and can be a modified polyvinyl alcohol copolymer as described herein.

The present disclosure also provides a particle having a core-sheath structure or also referred to as a core-shell structure, and methods of making such a particle. The present disclosure including the compositions and the methods with respect to fibers are also applicable to particles. The term "particle" as used herein is understood to encompass any product in a particulate form, which may have any suitable shape and/or any suitable size. In embodiments, the particle may have a regular or uniform shape. e.g., spherical, cube, cuboid, cylinder, ellipsoid, or an irregular shape. In embodiments, the particle size may be at micron level or millimeter level. For example, the particle may have any suitable form, such as a bead, a microsphere, or a powder form. In some embodiments, the particle may have a size in a range of from about 1 micron to about 1,000 microns, for example, from about 5 microns to about 100 microns, from about 10 microns to about 100 microns, from about 2 microns to about 10 microns, or any other suitable size or range. In some embodiments, the particle may have a size in a range of from about 1 millimeter (mm) to about 10 mm, for example, from about 1 mm to 5 mm, from about 1 mm to 2 mm, or any other suitable size or range.

In embodiments, the particle has a core-shell structure including a core region and a shell region at least partially covering, encompassing, or surrounding the core region. The core region includes a polymer comprising at least one of a vinyl acetate moiety or a vinyl alcohol moiety having a first degree of hydrolysis less than 100% as described herein. In example embodiments, the shell region is disposed radially outward from the core region. The shell region includes the polymer comprising at least one of a vinyl acetate moiety or a vinyl alcohol moiety and having a second degree of hydrolysis greater than the first degree of hydrolysis. In some embodiments, the particle has an increasing gradient in a degree of hydrolysis of the polymer extending radially from a center of the core region to an exterior surface of the shell region. As described herein, the polymer comprising at least one of a vinyl acetate moiety or a vinyl alcohol moiety comprises a polyvinyl alcohol homopolymer, a polyvinyl acetate homopolymer, a polyvinyl alcohol copolymer, a modified polyvinyl alcohol copolymer, or combinations thereof. For example, the polyvinyl alcohol copolymer is a copolymer of vinyl acetate and vinyl alcohol in some embodiments. The polyvinyl alcohol copolymer may be anionically modified to further include a carboxylate, a sulfonate, or combinations thereof.

In embodiments, a method for making a particle having a core-shell structure includes at least one step of admixing a particle (or a certain amount of particles) comprising a hydrolyzable polymer as described herein with a hydrolysis agent solution to form a mixture so as to increase the degree of hydrolysis in a surface region, e.g., the shell region, of the particle. The polymer comprises at least one of a vinyl acetate moiety or a vinyl alcohol moiety and has a degree of hydrolysis less than 100%. In embodiments, the particle has a uniform composition. The resulting particle has a core-shell structure including a core region and a shell region (or the surface region). As described herein, the hydrolysis agent solution comprises a hydrolysis agent and a solvent. The mixture of the particle and the hydrolysis agent solution may be heated. The hydrolysis agent solution is admixed under conditions sufficient to provide at least one of a predetermined degree of hydrolysis or a predetermined an increasing gradient in the degree of hydrolysis increase from a center of the particle to an exterior surface of the particle. The particle may be admixed with the hydrolysis agent solution at a temperature in a range of about 10° C. to about 100° C. for a period of time in a range of from about 1 minute to about 48 hours as described above. The polymer may have a degree of hydrolysis greater than about 79% and less than about 96% prior to the step of admixing. The polymer in the sheath region has a second degree of hydrolysis in a range of from about 88% to about 96% after the step of admixing. The resulting particle is water-soluble after the step of admixing.

In another aspect, the present disclosure also provides three dimensional articles having a core-sheath structure or also referred to as a core-shell structure including a surface region, i.e., the sheath region, and a core region, and methods of making such an article. The present disclosure including the compositions and the methods with respect to fibers or particles are also applicable to any three dimensional article. The sheath region includes the polymer comprising at least one of a vinyl acetate moiety or a vinyl alcohol moiety and having a second degree of hydrolysis greater than the first degree of hydrolysis for the polymer in the core region. In some embodiments, the article has an increasing gradient in a degree of hydrolysis of the polymer extending from a center of the core region to an exterior surface of the sheath region. The articles may have any suitable size and shape, and can be disposable after use and dissolvable in water.

The following paragraphs describe further aspects of the disclosure.

1. A method of treating a fiber, said method comprising: admixing a fiber comprising a polymer comprising at least one of a vinyl acetate moiety or a vinyl alcohol moiety and having a degree of hydrolysis less than 100% with a hydrolysis agent solution to form a mixture so as to increase the degree of hydrolysis of at least a portion of the fiber.

2. The method according to clause 1, further comprising heating the mixture of the fiber and the hydrolysis agent solution.

3. The method according to clause 1 or 2, wherein the hydrolysis agent solution is admixed under conditions sufficient to provide at least one of a predetermined degree of hydrolysis or a predetermined degree of hydrolysis increase to the portion of the fiber.

4. The method according to any of clauses 1-3, wherein the fiber is admixed with the hydrolysis agent solution for a period of time in a range of from about 1 minute to about 48 hours.

5. The method according to any of clauses 1-4, wherein the fiber is admixed with the hydrolysis agent solution at a temperature in a range of about 10° C. to about 100° C.

6. The method according to any of clauses 1-5, wherein the polymer has a degree of hydrolysis greater than about 79% and less than about 96% prior to admixing the fiber with the hydrolysis agent solution.

7. The method according to any of clauses 1-6, wherein the fiber is water-soluble after admixing the fiber with the hydrolysis agent solution.

8. The method according to any of clauses 1-7, wherein the hydrolysis agent solution comprises a hydrolysis agent and a solvent.

9. The method according to clause 8, wherein the hydrolysis agent comprises a metallic hydroxide, a metal hydride, a sulfite, sulfur dioxide, a dithionate, a thiosulfate, a hydrazine, oxalic acid, formic acid, ascorbic acid, dithiothreitol, a phosphite, a dihypophosphite, phosphorous acid, sulfuric acid, sulphonic acid, hydrochloric acid, ammonium hydroxide, water, or combinations thereof.

10. The method according to clause 8, wherein the hydrolysis agent comprises a metallic hydroxide.

11. The method according to clause 10, wherein the metallic hydroxide comprises an alkali metal hydroxide, an alkaline earth metal hydroxide, a main group metal hydroxide, or combinations thereof.

12. The method according to clause 8, wherein the hydrolysis agent comprises sodium hydroxide, potassium hydroxide, calcium hydroxide, barium hydroxide, trialkyltin hydroxide, or combinations thereof.

13. The method according to any of clauses 8-12, wherein the hydrolysis agent is provided in an amount of about 0.2% to about 75% (w/w) based on a weight of the solvent.

14. The method according to any of clauses 8-13, wherein the fiber is not soluble in the solvent.

15. The method according to any of clauses 8-14, wherein the solvent comprises a polar solvent.

16. The method according to any of clauses 8-15, wherein the solvent comprises one or more solvents selected from the group consisting of: n-propanol, acetone, ethanol, N-methylpyrrolidone, methanol, acetonitrile, N,N-dimethylformamide, dimethyl sulfoxide, formic acid, water, and combinations thereof.

17. The method according to clause 8, wherein the solvent comprises a nonpolar solvent.

18. The method according to clause 8, wherein the solvent comprises an alcohol that is a liquid under admixing conditions.

19. The method according to clause 8, wherein the solvent comprises a mixture of a first solvent and a second solvent.

20. The method according to clause 19, wherein the first solvent comprises a polar solvent and the second solvent comprises a nonpolar solvent.

21. The method according to clause 19, wherein the first solvent has a first dielectric constant and the second solvent has a second dielectric constant and the first dielectric constant is higher than the second dielectric constant.

22. The method according to clause 21, wherein a difference between the first dielectric constant and the second dielectric constant is at least 3.

23. The method according to any of clauses 1-22, further comprising admixing an activator with the fiber and the hydrolysis agent solution.

24. The method according to any of clauses 1-23, wherein the polymer comprising at least one of a vinyl acetate moiety or a vinyl alcohol moiety comprises a polyvinyl alcohol homopolymer, a polyvinyl acetate homopolymer, a polyvinyl alcohol copolymer, or combinations thereof.

25. The method according to clause 24, wherein the polyvinyl alcohol copolymer is a copolymer of vinyl acetate and vinyl alcohol.

26. The method according to clause 24, wherein the polyvinyl alcohol copolymer comprises an anionically modified copolymer.

27. The method according to clause 26, wherein the anionically modified copolymer comprises a carboxylate, a sulfonate, or combinations thereof.

28. The method according to any of clauses 1-27, wherein the fiber further comprises an additional polymer.

29. The method according to clause 28, wherein the additional polymer is selected from the group consisting of: polyvinyl alcohol, polyvinyl acetate, polyacrylate, a water-soluble acrylate copolymer, polyvinyl pyrrolidone, polyethylenimine, pullulan, guar gum, gum Acacia, xanthan gum, carrageenan, starch, modified starch, polyalkylene oxide, polyacrylamide, polyacrylic acid, cellulose, cellulose ether, cellulose ester, cellulose amide, polycarboxylic acid, polyamino acid, polyamide, a gelatin, dextrin, copolymers of the foregoing, and combinations of any of the foregoing additional polymers or copolymers.

30. The method according to any of clauses 1-29, wherein admixing the fiber with the hydrolysis agent solution is performed under conditions sufficient to provide a fiber having a transverse cross-section having a structure including a core and a sheath, wherein the core comprises the polymer with a first degree of hydrolysis and the sheath comprises the polymer with a second degree of hydrolysis greater than the first degree of hydrolysis.

31. The method according to any of clauses 1-30, wherein admixing the fiber with hydrolysis agent solution is performed under conditions sufficient to provide a fiber having a transverse cross-section having an increasing gradient in a degree of hydrolysis from an interior region of the fiber to a surface region of the fiber.

32. The method according to any of clauses 1-31, wherein admixing the fiber with the hydrolysis agent solution is performed under conditions sufficient to provide a fiber having a transverse cross-section with the polymer having a same degree of hydrolysis across the transverse cross-section.

33. The method according to clause 1, wherein the hydrolysis agent solution comprises sodium hydroxide and methanol, the admixing comprises immersing the fiber in the hydrolysis agent solution, and the mixture of the fiber in the hydrolysis agent solution is heated to a temperature of about 30° C. to about 60° C. for about 1 minute to about 24 hours.

34. The method according to clause 1, wherein the fiber comprises a copolymer of vinyl alcohol and vinyl acetate having a degree of hydrolysis of about 88%, about 92%, or about 96%, the hydrolysis agent solution comprises sodium hydroxide and methanol, the admixing comprises immersing the fiber in the hydrolysis agent solution, and the mixture of the fiber in the hydrolysis agent solution is heated to a temperature of about 30° C. to about 60° C. for about 12 hours to about 24 hours.

35. The method according to clause 1, wherein the fiber comprises an anionically modified copolymer having a carboxylate or sulfonate modification and a degree of hydrolysis of about 88%, about 92%, or about 96%, the hydrolysis agent solution comprises sodium hydroxide and methanol, the admixing comprises immersing the fiber in the hydrolysis agent solution, and the mixture of the fiber in the hydrolysis agent solution is heated to a temperature of about 30° C. to about 60° C. for about 12 hours to about 24 hours.

36. The method according to clause 1, wherein the fiber comprises a copolymer of vinyl alcohol and vinyl acetate having a degree of hydrolysis of about 88%, about 92%, or about 96%, the hydrolysis agent solution comprises sodium hydroxide and methanol, the admixing comprises immersing the fiber in the hydrolysis agent solution, and the mixture of the fiber in the hydrolysis agent solution is heated to a temperature of about 30° C. to about 60° C. for about 1 hour to about 12 hours.

37. The method according to clause 1, wherein the fiber comprises an anionically modified copolymer having a carboxylate or sulfonate modification and a degree of hydrolysis of about 88%, about 92%, or about 96%, the hydrolysis agent solution comprises sodium hydroxide and methanol, the admixing comprises immersing the fiber in the hydrolysis agent solution, and the mixture of the fiber in the hydrolysis agent solution is heated to a temperature of about 30° C. to about 60° C. for about 1 hour to about 12 hours.

38. The method according to clause 1, wherein the fiber comprises a copolymer of vinyl alcohol and vinyl acetate having a degree of hydrolysis of about 88%, about 92%, or about 96%, the hydrolysis agent solution comprises sodium hydroxide and methanol, the admixing comprises immersing the fiber in the hydrolysis agent solution, and the mixture of the fiber in the hydrolysis agent solution is heated to a temperature of about 30° C. to about 60° C. for up to about 1 hour.

39. The method according to clause 1, wherein the fiber comprises an anionically modified copolymer having a carboxylate or sulfonate modification and a degree of hydrolysis of about 88%, about 92%, or about 96%, the hydrolysis agent solution comprises sodium hydroxide and methanol, the admixing comprises immersing the fiber in the hydrolysis agent solution, and the mixture of the fiber in the hydrolysis agent solution is heated to a temperature of about 30° C. to about 60° C. for up to about 1 hour.

40. A method of treating a fiber, said method comprising: contacting a surface of a fiber comprising a polymer comprising at least one of a vinyl acetate moiety or a vinyl alcohol moiety and having a degree of hydrolysis less than 100% with a hydrolysis agent solution to increase the degree of hydrolysis of the polymer in a region of the fiber comprising at least the surface of the fiber.

41. The method according to clause 40, wherein contacting a surface of a fiber with a hydrolysis agent solution comprises immersion, spraying, transfer coating, wicking, foaming, brushing, rolling, humidification, vapor deposition, printing, or combinations thereof.

42. The method according to clause 40 or 41, comprising contacting the surface of the fiber with the hydrolysis agent solution is performed after formation of the fiber as part of a continuous inline process.

43. The method according to any of clauses 40-42, wherein the fiber is in motion during the contacting of the surface of the fiber with the hydrolysis agent solution.

44. The method according to any of clauses 40-43, comprising contacting the surface of the fiber with the hydrolysis agent solution is performed in a batch by a batch process.

45. The method according to any of clauses 40-44, wherein the fiber comprises at least one of a staple fiber, a staple yarn, a fiber fill, needle punch fabrics, bonding fibers, or combinations thereof.

46. The method according to any of clauses 40-45, further comprising washing and drying the fiber after contacting the surface of the fiber with the hydrolysis agent solution.

47. The method according to clause 46, wherein washing the fiber comprises rinsing the fiber with a non-solvent.

48. The method according to any of clauses 40-47, wherein drying the fiber comprises air jet drying, agitating, vortexing, centrifuging, or combinations thereof.

49. The method according to any of clauses 40-48, wherein the polymer comprising at least one of a vinyl acetate moiety or a vinyl alcohol moiety comprises a polyvinyl alcohol homopolymer, a polyvinyl acetate homopolymer, a polyvinyl alcohol copolymer, or combinations thereof.

50. The method according to clause 49, wherein the polyvinyl alcohol copolymer comprises an anionically modified copolymer.

51. The method according to clause 50, wherein the anionically modified copolymer comprises a carboxylate, a sulfonate, or combinations thereof.

52. The method according to any of clauses 40-51, wherein the fiber further comprises an additional polymer.

53. The method according to clause 52, wherein the additional polymer is selected from the group consisting of: a polyvinyl alcohol, a polyvinyl acetate, a polyacrylate, a water-soluble acrylate copolymer, a polyvinyl pyrrolidone, a polyethylenimine, a pullulan, a guar gum, a gum Acacia, a xanthan gum, a carrageenan, a starch, a modified starch, a polyalkylene oxide, a polyacrylamide, a polyacrylic acid, a cellulose, a cellulose ether, a cellulose ester, a cellulose amide, a polycarboxylic acid, a polyamino acid, a polyamide, a gelatin, dextrin, copolymers of the foregoing, and combinations of any of the foregoing additional polymers or copolymers.

54. The method according to any of clauses 40-53, wherein the hydrolysis agent solution comprises a hydrolysis agent and a solvent.

55. The method according to clause 54, wherein the hydrolysis agent comprises a metallic hydroxide, a metal hydride, a sulfite compound, sulfur dioxide, a dithionate, a thiosulfate, a hydrazine, oxalic acid, formic acid, ascorbic acid, dithiothreitol, a phosphite, a hypophosphite, phosphorous acid, sulfuric acid, sulphonic acid, hydrochloric acid, ammonium hydroxide, water, or combinations thereof.

56. The method according to clause 54, wherein the hydrolysis agent comprises a metallic hydroxide.

57. The method according to clause 56, wherein the metallic hydroxide comprises an alkali metal hydroxide, an alkaline earth metal hydroxide, a main group metal hydroxide, or combinations thereof.

58. The method according to clause 56, wherein the metal hydroxide hydrolysis agent comprises sodium hydroxide, potassium hydroxide, calcium hydroxide, barium hydroxide, trialkyltin hydroxide, or combinations thereof 59. The method according to clause 54, wherein the hydrolysis agent is provided in an amount of about 0.2% to about 75% (w/w) based on a weight of the solvent.

60. The method according to clause 54, wherein the fiber is not soluble in the solvent.

61. The method according to clause 54, wherein the hydrolysis agent solution further comprises an activator.

62. A method of treating a nonwoven web comprising a plurality of fibers comprising a polymer comprising at least one of a vinyl acetate moiety or a vinyl alcohol moiety and having a degree of hydrolysis less than 100%, said method comprising: contacting at least a portion of the nonwoven web with a hydrolysis agent solution to increase the degree of hydrolysis of the polymer in the plurality of fibers.

63. The method according to clause 62, wherein contacting at least a portion of the nonwoven web with a hydrolysis agent solution comprises immersion, spraying, transfer coating, wicking, foaming, brushing, rolling, humidification, vapor deposition, printing, or combinations thereof.

64. The method according to clause 62 or 63, wherein contacting at least a portion of the nonwoven web with a hydrolysis agent solution occurs concurrently with bonding the plurality of fibers into the nonwoven web.

65. The method according to clause 64, wherein contacting and bonding comprises chemical bonding.

66. The method according to clause 64, wherein contacting and bonding comprises using heat activated catalysis.

67. The method according to any of clauses 62-66, wherein the polymer comprising at least one of a vinyl acetate moiety or a vinyl alcohol moiety comprises a polyvinyl alcohol homopolymer, a polyvinyl acetate homopolymer, a polyvinyl alcohol copolymer, or combinations thereof.

68. The method according to clause 67, wherein the polyvinyl alcohol copolymer comprises an anionically modified copolymer.

69. The method according to clause 68, wherein the anionically modified copolymer comprises a carboxylate, a sulfonate, or combinations thereof.

70. The method according to any of clauses 62-69, wherein the fiber further comprises an additional polymer.

71. The method according to clause 70, wherein the additional polymer is selected from the group consisting of: polyvinyl alcohol, polyvinyl acetate, polyacrylate, a water-soluble acrylate copolymer, polyvinyl pyrrolidone, polyethylenimine, pullulan, guar gum, gum Acacia, xanthan gum, carrageenan, starch, modified starch, polyalkylene oxide, polyacrylamide, polyacrylic acid, cellulose, cellulose ether, cellulose ester, cellulose amide, polycarboxylic acid, polyamino acid, polyamide, gelatin, dextrin, copolymers of the foregoing, and combinations of any of the foregoing additional polymers or copolymers.

72. The method according to any of clauses 62-71, wherein the hydrolysis agent solution comprises a hydrolysis agent and a solvent.

73. The method according to clause 72, wherein the hydrolysis agent comprises a metallic hydroxide, a metal hydride, a sulfite compound, sulfur dioxide, a dithionate, a thiosulfate, a hydrazine, oxalic acid, formic acid, ascorbic acid, dithiothreitol, a phosphite, a hypophosphite, phosphorous acid, sulfuric acid, sulphonic acid, hydrochloric acid, ammonium hydroxide, water, or combinations thereof.

74. The method according to clause 72, wherein the hydrolysis agent comprises a metallic hydroxide.

75. The method according to clause 74, wherein the metallic hydroxide comprises an alkali metal hydroxide, an alkaline earth metal hydroxide, a main group metal hydroxide, or combinations thereof.

76. The method according to clause 75, wherein the hydrolysis agent comprises sodium hydroxide, potassium hydroxide, calcium hydroxide, barium hydroxide, trialkyltin hydroxide, or combinations thereof.

77. The method according to any of clauses 72-76, wherein the hydrolysis agent is provided in an amount of about 0.2% to about 75% (w/w) based on a weight of the solvent.

78. The method according to any of clauses 72-77, wherein the fiber is not soluble in the solvent.

79. The method according to any of clauses 72-78, wherein the hydrolysis agent solution further comprises an activator.

80. A method for making a particle having a core-shell structure, comprising: admixing a particle comprising a polymer comprising at least one of a vinyl acetate moiety or a vinyl alcohol moiety and having a degree of hydrolysis less than 100% with a hydrolysis agent solution to form a mixture so as to increase the degree of hydrolysis in a surface region of the particle.

81. The method according to clause 80, further comprising heating the mixture of the particle and the hydrolysis agent solution.

82. The method according to clause 80 or 81, wherein the hydrolysis agent solution is admixed under conditions sufficient to provide at least one of a predetermined degree of hydrolysis or a predetermined an increasing gradient in the degree of hydrolysis increase from a center of the particle to an exterior surface of the particle.

83. The method according to any of clauses 80-82, wherein the particle is admixed with the hydrolysis agent solution at a temperature in a range of about 10° C. to about 100° C. for a period of time in a range of from about 1 minute to about 48 hours.

84. The method according to any of clauses 80-83, wherein the polymer has a degree of hydrolysis greater than about 79% and less than about 96% prior to admixing the particle with the hydrolysis agent solution.

85. The method according to any of clauses 80-84, wherein the particle has a core-structure including a core region and a shell region, the polymer in the shell region has a degree of hydrolysis in a range of from about 88% to about 96% after admixing the particle with the hydrolysis agent solution.

86. The method according to any of clauses 80-85, wherein the particle is water-soluble after admixing the particle with the hydrolysis agent solution.

EXAMPLES

Fibers Used

As shown in Table 2, four fibers, Fiber A, Fiber B, Fiber C, and Fiber D, which comprise a copolymer of vinyl acetate and vinyl alcohol having a degree of hydrolysis of 88%, 96%, 98%, and 99.99%, respectively, were used as the starting materials. These fibers have uniform composition, and have additional properties shown in Table 2. In the Examples and Comparative Examples described herein, the fibers being used have a fineness of 2.2 dtex.

TABLE 2

| Fiber | Viscosity (4% solution) | DH (mol %) | Fineness (dtex) | Solubility Temp (C.) | Tenacity (cN/dtex) | Elonga-tion (%) |
|---|---|---|---|---|---|---|
| A | 22-23 | 88 | 1.7 2.2 | 20 | 5 | 20 |
| B | 22-23 | 96 | 1.2 1.7 | 40 | 7 | 15 |
| C | 22-23 | 98 | 1.2 1.7 | 70 | 7 | 12 |
| D | 22-23 | 99.99 | 1.2 1.7 | 95 | 9 | 10 |

Example 1

The samples of Fiber A, which comprises a copolymer of vinyl acetate and vinyl alcohol having a degree of hydrolysis of 88% as the sole fiber forming material were post-process hydrolyzed as follows. In the Examples, a polymer comprising vinyl alcohol moieties is referred as "a polyvinyl alcohol polymer," and a fiber comprising such a polymer is referred as "a polyvinyl alcohol fiber." 5 grams (g) of the polyvinyl alcohol fibers were immersed in a 10% solution of sodium hydroxide in methanol. The fibers did not dissolve in the methanol. The resulting mixture was heated to 60° C. for 24 hours. After 24 hours, the mixture was cooled and the fibers separated from the methanol. The resulting hydrolyzed fibers were dried to remove any residual methanol prior to measuring the degree of hydrolysis using the titration method disclosed herein. The degree of hydrolysis of the hydrolyzed fibers was found to be 99.9% using the titration method.

Thus, Example 1 shows using the method of the disclosure to prepare a post-process hydrolyzed polyvinyl alcohol fiber.

Example 2

Fibers comprising a copolymer of vinyl acetate and vinyl alcohol having a degree of hydrolysis of 88%, 92% or 96% as the sole fiber forming material or in combination with other fiber forming materials are post-process hydrolyzed as follows. 5 g of the polyvinyl alcohol fibers are immersed in a 25% solution of sodium hydroxide in a solvent or mixture (i.e., 10% methanol and 90% hexane by weight) thereof, having a dielectric constant of about 20 or greater. The fibers do not dissolve in the solvent. The resulting mixture is heated to 60° C. for 12 hours. After 12 hours, the mixture is cooled and the fibers separated from the solvent. The resulting hydrolyzed fibers are dried to remove any residual solvent prior to measuring the degree of hydrolysis using the titration method disclosed herein. The degree of hydrolysis of the hydrolyzed fibers are found to be 99.9% using the titration method.

Thus, Example 2 shows using methods of the disclosure to prepare post-process hydrolyzed polyvinyl alcohol fibers.

Example 3

Fibers comprising a copolymer of vinyl acetate and having a degree of hydrolysis of 88%, 92% or 96% as the sole fiber forming material or in combination with other fiber forming materials are post-process hydrolyzed as follows. 5 g of the polyvinyl alcohol fibers are immersed in a 10% solution of sodium hydroxide in methanol. The fibers do not dissolve in the solvent. The resulting mixture is heated to 60° C. for 1 to 6 hours. After 1 to 6 hours, the mixture is cooled and the fibers separated from the solvent. The resulting hydrolyzed fibers are dried to remove any residual solvent prior to measuring the degree of hydrolysis using the solution titration method and the ATR-FTIR method as disclosed herein. The hydrolyzed fibers are found to have a transverse cross-section having an increasing gradient in the degree of hydrolysis of the polymer an inner region to a surface region.

Thus, Example 3 shows using methods of the disclosure to prepare post-process hydrolyzed polyvinyl alcohol fibers of the disclosure having a transverse cross-section characterized by a gradient structure.

Example 4

Fibers comprising a copolymer of vinyl acetate and vinyl alcohol having a degree of hydrolysis of 88%, 92% or 96% as the sole fiber forming material or in combination with other fiber forming materials are post-process hydrolyzed as follows. 5 g of the polyvinyl alcohol fibers are immersed in a 10% solution of sodium hydroxide in a 60/40 (w/w) mixture of DMSO/water. The fibers do not dissolve in the solvent. The resulting mixture is heated to 60° C. for up to one hour. The mixture is then cooled and the fibers separated from the solvent. The resulting hydrolyzed fibers are dried to remove any residual solvent prior to measuring the degree of hydrolysis using the solution titration method and the ATR-FTIR method as disclosed herein. The hydrolyzed fibers are found to have a transverse cross-section having a core-sheath structure, wherein only the polymer of the surface of the fiber a greater degree of hydrolysis than the polymer of the core.

Thus, Example 4 shows using methods of the disclosure to prepare post-process hydrolyzed polyvinyl alcohol fibers of the disclosure having a transverse cross-section characterized by a core-sheath structure.

Example 5

Fibers comprising polyvinyl alcohol having a degree of hydrolysis of 88%, 92% or 96% as the sole fiber forming material or in combination with other fiber forming materials are post-process hydrolyzed as follows. 5 g of the polyvinyl alcohol fibers are immersed in a 10% solution of sodium hydroxide in methanol. The fibers do not dissolve in the solvent. The resulting mixture is heated to 60° C. for 1-6 hours. After 1-6 hours, the mixture is cooled and the fibers separated from the solvent. The resulting hydrolyzed fibers are dried to remove any residual solvent prior to measuring the degree of hydrolysis using the solution titration method and the ATR-FTIR method as disclosed herein. The hydrolyzed fibers are found to have a transverse cross-section having an increasing gradient in the degree of hydrolysis from an interior region to a surface region.

Thus, Example 5 shows using methods of the disclosure to prepare post-process hydrolyzed polyvinyl alcohol fibers of the disclosure having a transverse cross-section characterized by an increasing degree of hydrolysis gradient from an interior region to a surface region.

Examples 6-46

Examples 6-46 further illustrate controlling the solubility profile of cold-water soluble fibers by creating a "core and sheath" structure of varying solubility via secondary saponification reaction. Fiber A comprising a copolymer of vinyl acetate and vinyl alcohol, which has a degree of polymerization of 1,700 and a degree of hydrolysis of 88%, was used as a starting material. The fibers or nonwoven webs including Fiber A were treated in a batch process, respectively, at a temperature in an increasing range (20, 30, 40, 50, or 60° C.), for a period of time in an increasing range (1, 2, 5, or 10 minutes), while maintaining the base concentration (0.05M). Depending on how many fibers are to be modified, the amount of base needed to fully saponify the sample was calculated to determine how much base to add to the reaction. Referring to the reaction in Scheme (1), for example, the calculated amount of NaOH needed to fully hydrolyze 3 g of the fibers (Fiber A) is 0.299 g.

The samples were made using the following procedures: Base (NaOH or KOH) pellets were crush with a mortar and pestle, then placed in a vacuum oven at 60° C. for 5 hours. Such a base was further dried in a desiccator for 12 hours prior to use, and then returned to the desiccator after each use. Dried NaOH or KOH of a calculated amount and the solvent of a corresponding amount of solvent were added into an Erlenmeyer flask of a suitable size, so that a resulting molarity of the reaction solution was 0.05 M. A stir bar was placed into the reaction flask to ensure that the base is thoroughly dissolved in the solvent. Heat might be used to expedite the dissolution if needed. A timer and long forceps were used. A Buchner funnel washing station with a vacuum flask and a pump was set up. The fibers of a pre-determined amount were placed in the reaction flask, while the timer was started. The fibers were pulled out the reaction solution at the designated time intervals (e.g., 1, 2, 5, 10 minutes, respectively) and rinsed with methanol in the Buchner funnel under vacuum filtration conditions. The resulting modified fibers were thoroughly dried. The modified fibers were placed in a labeled large weigh boat and allowed to dry in a chemical hood overnight. After the modified fibers were dried, the modified fiber sample was analyzed using ATR-FTIR. This procedure was the same for a wet batch process for treating Fiber A nonwoven web, except that the 2 inch×1 inch nonwoven webs (3 for each time interval) were suspended in the solution via an alligator clamp.

The degree of hydrolysis of each resulting sample was determined by the titration technique, which quantifies the amount of hydroxyl groups present on a polymer chain, and/or ART-FTIR, which quantifies the loss of acetate groups ($1715$ cm$^{-1}$ peak) in a sample. Differential Scanning calorimetry (DSC) was used to test glass transition temperature ($T_g$) values and transitions of the modified samples.

Unless expressly described otherwise, the degree of hydrolysis for a fiber or a nonwoven web obtained using ATR-FTIR is with respect to the sample surface or the sheath region. The degree of hydrolysis in the interior or core region of such a sample may be the same as that of an untreated sample.

Example 6

Fibers (Fiber A) were treated with 0.05 M NaOH in methanol at 50° C. for 10 minutes. The surfaces of the resulting modified fibers were analyzed under ATR-FTIR. At least three fibers or three areas of the same fiber were tested. The ATR-FTIR curves overlapped with each other without any significant difference. These results show identical degrees of hydrolysis and uniform modification of the fibers under the same conditions.

Examples 7-10

Four samples of Fiber A were treated with 0.05 M of a base (NaOH or KOH) in a solvent (methanol or 10% methanol/90% hexane) at 40° C. for 1 minute, respectively. For these four samples, Examples 7-10, the combinations of the base and the solvent are: KOH and methanol (MeOH), NaOH and MeOH, KOH and MeOH/hexane, and NaOH and MeOH/hexane, respectively. Comparative Example 1 is Fiber A.

Figure 9:
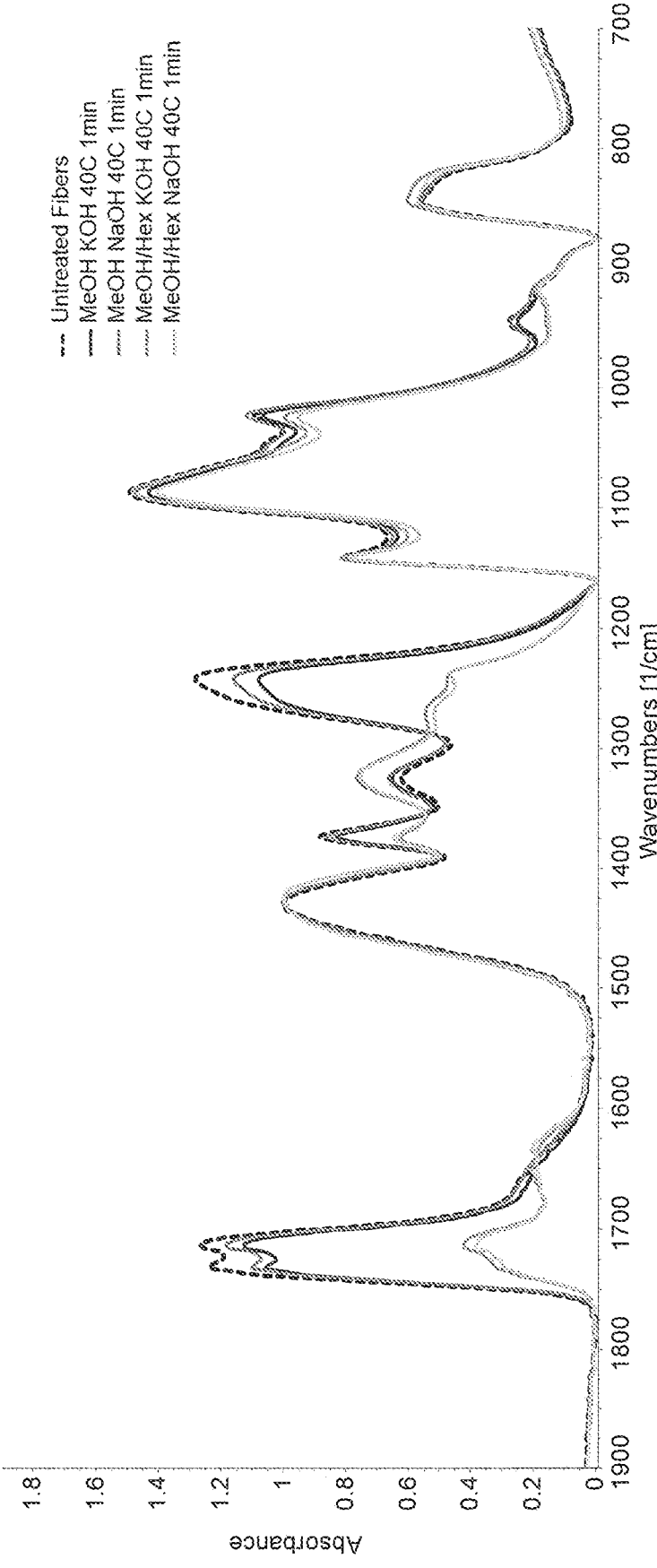
FIG. 9 shows ATR-FTIR results of fibers (Fiber A) before and after the fibers are treated with 0.05 M of a base (NaOH or KOH) in a solvent (methanol or 10% methanol/90% hexane) at 40° C. for 1 minute, respectively.

Referring to FIG. 9 showing the ATR-FTIR curves of Examples 7-10 and Comparative Example 1, it was found that the solvent having 10% methanol and 90% hexane catalyzes the secondary saponification of the fibers comprising a copolymer of vinyl acetate and vinyl alcohol.

The samples of Fiber A were also treated with 0.05 M NaOH in methanol at different temperatures for different time intervals, for example, at 50° C. for 1 minute, 2 minutes, 5 minutes, and 10 minutes, respectively. Based on a model derived from the rate of change in the degree of hydrolysis, it was found that the secondary saponification is a temperature driven second order reaction.

Examples 11-22

Table 3 shows the reaction conditions and the results of Examples 11-22, which are treated fibers. The fibers were treated with NaOH. The results include degree of hydrolysis, fiber shrinkage, and glass transition temperature (Tg), compared to those of Comparative Examples 1 and 2, which are fibers A and B comprising a copolymer of vinyl acetate and vinyl alcohol having degree of hydrolysis of 88% and 96%, respectively, and have uniform composition and structure throughout the fibers. Examples 11-22 were treated fibers from the samples of Fiber A. The degree of hydrolysis values of Examples 11-22 were obtained using ATR-FTIR on the surface or sheath regions of the fibers. The degree of hydrolysis in the interior or core region of such a sample may be the same as that of the untreated fiber.

TABLE 3

| Example No. | Conditions: 0.05M NaOH | | Average % DH | Shrinkage (%) | | |
|---|---|---|---|---|---|---|
| (Fiber) | Temp (° C.) | Time (min) | (mol %) | 10° C. | 23° C. | Tg (° C.) |
| No. 11 | 40 | 1 | 90.90 | | | |
| No. 12 | | 2 | 91.30 | | | |
| No. 13 | | 5 | 92.70 | | | |
| No. 14 | | 10 | 94.70 | 22.41 | 44.91 | |
| No. 15 | 50 | 1 | 92.10 | | | 73.67 |
| No. 16 | | 2 | 93.90 | | | 75.67 |
| No. 17 | | 5 | 95.40 | 45.37 | 43.98 | 78.67 |
| No. 18 | | 10 | 96.80 | 57.75 | 65.22 | 79.74 |
| No. 19 | 60 | 1 | 93.60 | | | |
| No. 20 | | 2 | 95.30 | | | |
| No. 21 | | 5 | 97.00 | 54.75 | 60.86 | |
| No. 22 | | 10 | 97.60 | 53.26 | 53.48 | |
| Comparative Example No. 1 (Fiber A) | non-modified | | 89.20 | 30.54 | | 72.32 |
| Comparative Example No. 2 (Fiber B) | | | 96.00 | no shrink | 51.77 | 81.44 |

Figure 10:
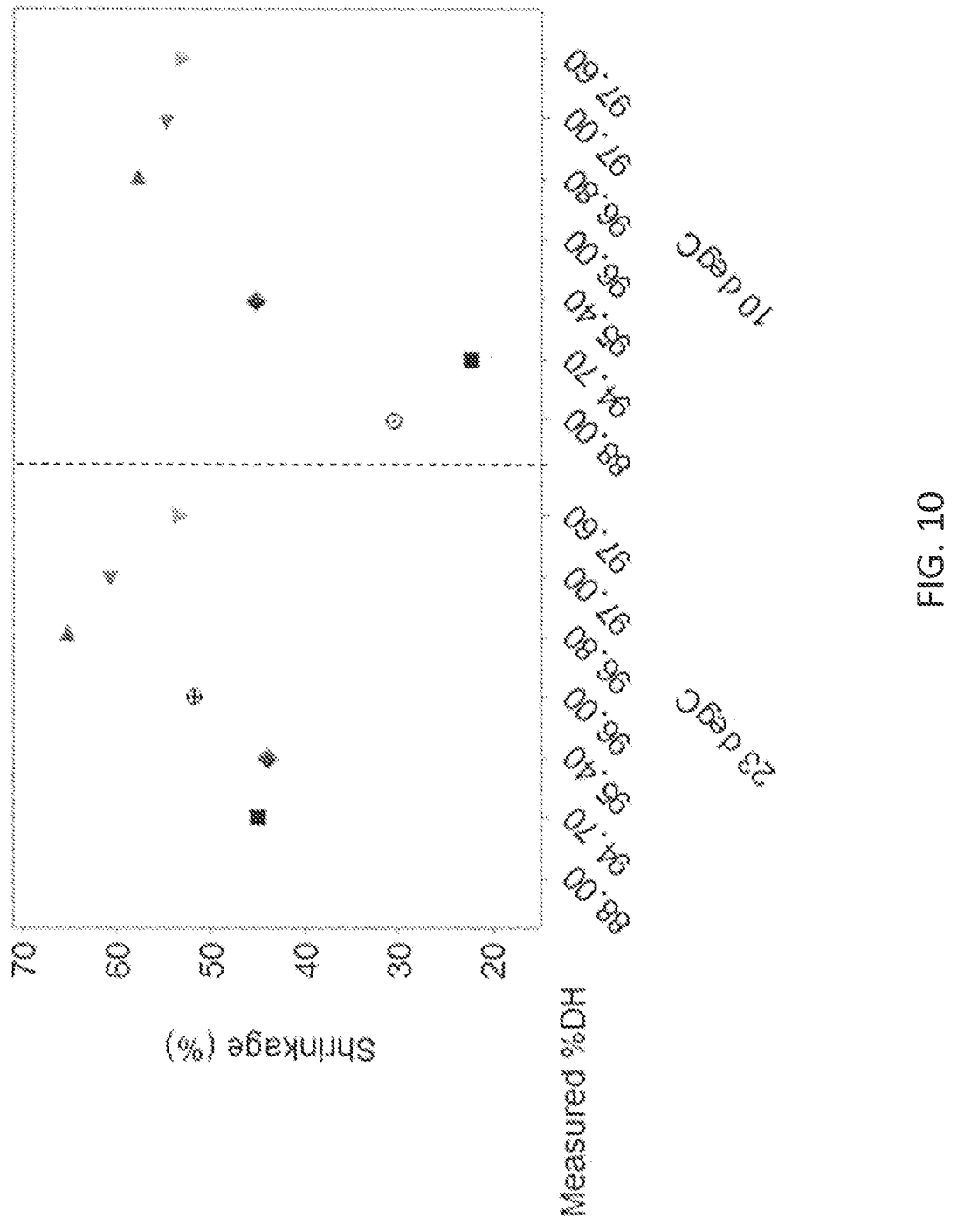
FIG. 10 shows fiber shrinkage along a longitudinal axis of different fibers having different degrees of hydrolysis with the fiber contacting water at a temperature of 10° C. or 23° C.

FIG. 10 shows the fiber shrinkage of different fibers having different degrees of hydrolysis while contacting water at a temperature of 10° C. or 23° C. Modified fibers such as Examples 11-22 outperform Comparative Examples such as Fibers A and B in an ability to swell with water and not solubilize immediately. The modified fiber having 96.8% of degree of hydrolysis (Example 18) shows the highest affinity for shrinking due to its higher degree of hydrolysis in its sheath, which stays intact, while its core having lower degree of hydrolysis swells with water. The resulting fibers maintain their performance at different water temperatures, for example, in the range of from 10° C. to 23° C.

As shown in Table 3, the glass transition (Tg) temperature of the treated fibers increases with an increase in the degree of hydrolysis. In the DSC curves, a modified fiber showed a broad range of glass transition, which suggests multiple species exist in such a fiber sample such as species having lower and higher degree of hydrolysis. Such a glass transition enhances manufacturing and bonding capabilities without sacrificing solubility.

Gel permeation chromatography (GPC) was used to test molecular weight and polydispersity of the polymer in the fiber samples before and after treatment. Table 4 shows the results of molecular weight and polydispersity of the polymer in Examples 15-18 and Comparative Examples 1-2. The refraction index increment (dn/dc) was 0.146 mL/g. Statistical analysis shows that there is no significant difference in the molecular weight and degree of polymerization of the polymer in the fiber samples before and after treatment under different conditions. Only the saponification or hydrolysis reaction occurs and non-desired transformations, such as esterification, degradation, and/or crosslinking, are suppressed and controlled by using the reaction conditions described herein.

TABLE 4

| Sample | Description/ Treatment Conditions | Test Run | Mn (kDa) | Mp (kDa) | Mw (kDa) | Polydis- persity (Mw/Mn) |
|---|---|---|---|---|---|---|
| Comparative Example 2 | Fiber B | 1 | 50.83 | 67.77 | 117.56 | 2.313 |
| | | 2 | 53.20 | 70.11 | 118.43 | 2.226 |

TABLE 4-continued

| Sample | Description/ Treatment Conditions | Test Run | Mn (kDa) | Mp (kDa) | Mw (kDa) | Polydis- persity (Mw/Mn) |
|---|---|---|---|---|---|---|
| Comparative Example 1 | Fiber A | 1 | 69.56 | 104.78 | 108.25 | 1.556 |
| | | 2 | 71.23 | 107.47 | 113.30 | 1.591 |
| Example 15 | Fiber A/ 50° C. 1 min | 1 | 58.21 | 104.00 | 116.32 | 1.998 |
| | | 2 | 65.18 | 104.77 | 118.60 | 1.82 |
| Example 16 | Fiber A/ 50° C. 2 min | 1 | 60.25 | 102.22 | 130.51 | 2.166 |
| | | 2 | 61.15 | 101.56 | 131.39 | 2.149 |
| Example 17 | Fiber A/ 50° C. 5 min | 1 | 60.19 | 86.58 | 149.12 | 2.477 |
| | | 2 | 58.60 | 84.11 | 149.73 | 2.555 |
| Example 18 | Fiber A/ 50° C. 10 min | 1 | 47.29 | 60.10 | 83.01 | 1.756 |
| | | 2 | 47.50 | 60.18 | 87.20 | 1.836 |

Examples 23-34

Table 5 shows the reaction conditions and the results of Examples 23-34, which are treated nonwoven webs. The nonwoven webs were treated with KOH. In the present disclosure, it was found that treatment of a sample such as fibers, a nonwoven web, or a block with KOH or NaOH does not make significant difference. The results include degree of hydrolysis, softness, and solubility testing results such as rupture time and disintegration time at 23° C., 40° C. and 60° C., compared to those of Comparative Examples 3-8. Comparative Examples 3, 5, 6, and 7 are nonwoven webs having fibers (Fiber A, Fiber B, Fiber C, and Fiber D, respectively) comprising a copolymer of vinyl acetate and vinyl alcohol having a uniform degree of hydrolysis of 88%, 96%, 98%, 99.99%, respectively. Comparative Example 4 is a nonwoven web having Fiber A exposure to heat methanol (50° C. for 10 minutes). Examples 23-34 were treated nonwoven webs comprising fibers (Fiber A). The degree of hydrolysis values of Examples 23-34 were obtained using ATR-FTIR on the surface or sheath regions of fibers. The degree of hydrolysis in the interior or core region of such a sample may be the same as that of the untreated fibers.

ATR-FTIR curves. The secondary saponification is limited to the surface of a tow fiber, therefore creating a higher degree of hydrolysis in the outer region and a lower degree of hydrolysis in the inner region of the sample.

TABLE 5

| Examples/ Nonwoven | Batch Reaction Conditions: 0.05M KOH | | | Solubilities 23 C. | | Solubilities 40 C. | | Solubilities 60 C. | | N = 6 |
| | Temp | Time (min) | % DH Average | Rupture Time (s) | Disintegration Time (s) | Rupture Time (s) | Disintegration Time (s) | Rupture Time (s) | Disintegration Time (s) | people Softness |
|---|---|---|---|---|---|---|---|---|---|---|
| No. 23 | 40 | 1 | 92.30 | 5.33 | 16.00 | 1.33 | 2.33 | 1.00 | 1.67 | |
| No. 24 | | 2 | 94.30 | 5.67 | 22.33 | 1.67 | 2.67 | 1.00 | 2.33 | |
| No. 25 | | 5 | 95.40 | 5.00 | 22.33 | 1.67 | 2.67 | 1.00 | 2.67 | |
| No. 26 | | 10 | 96.70 | 5.67 | 56.67 | 2.00 | 14.33 | 1.00 | 2.67 | 4.08 |
| No. 27 | 50 | 1 | 93.50 | 4.00 | 15.67 | 1.00 | 2.00 | 1.00 | 2.00 | |
| No. 28 | | 2 | 94.50 | 4.67 | 18.00 | 1.67 | 3.00 | 1.00 | 2.67 | |
| No. 29 | | 5 | 96.80 | 6.00 | 60.00 | 2.00 | 7.00 | 1.00 | 2.33 | |
| No. 30 | | 10 | 98.10 | 10.00 | 95.00 | 2.67 | 36.33 | 1.00 | 2.67 | 3.75 |
| No. 31 | 60 | 1 | 94.50 | 4.00 | 23.67 | 1.00 | 2.00 | 1.00 | 2.00 | |
| No. 32 | | 2 | 96.00 | 5.00 | 76.33 | 1.67 | 4.00 | 1.00 | 2.00 | |
| No. 33 | | 5 | 97.40 | 6.00 | 180.00 | 2.67 | 26.33 | 1.00 | 2.33 | |
| No. 34 | | 10 | 98.30 | 11.67 | 180.00 | 4.00 | 24.00 | 2.67 | 14.33 | 3.58 |
| Comparative Example (CEx) No. 3 (Fiber A) | non-modified | | 89.20 | 21.00 | 58.67 | | | | | 2.92 |
| CEx. 4 (Fiber A, exposed to reaction conditions) | | | | | | | | | | 3.12 |
| CEx. 5 (Fiber B) | | | 96.00 | 103.00 | 176.00 | 7.00 | 28.67 | | | |
| CEx. 6 (Fiber C) | | | 98.00 | Insoluble | | Insoluble | | | | |
| CEx. 7 (Fiber D) | | | 99.00 | | | | | | | |
| CEx. 8(75% Fiber B, 25% 20 dpf PET) | | | | 123.33 | | 8.67 | | | | 1.98 |

Figure 11:
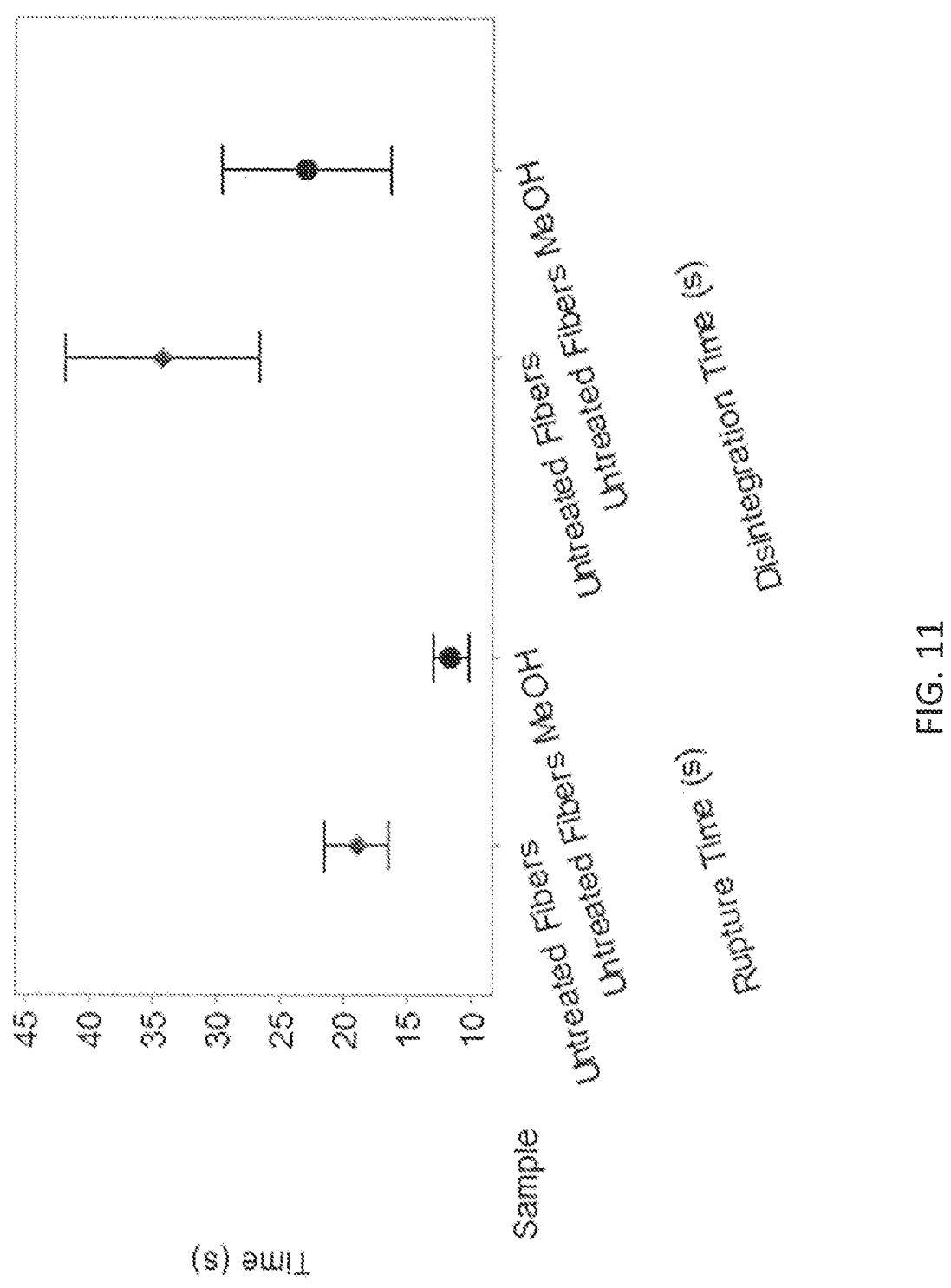
FIG. 11 shows rupture time (seconds) and disintegration time (seconds) of a nonwoven web having an exemplary fiber (Fiber A) before and after exposed to heated methanol.
Figure 12:
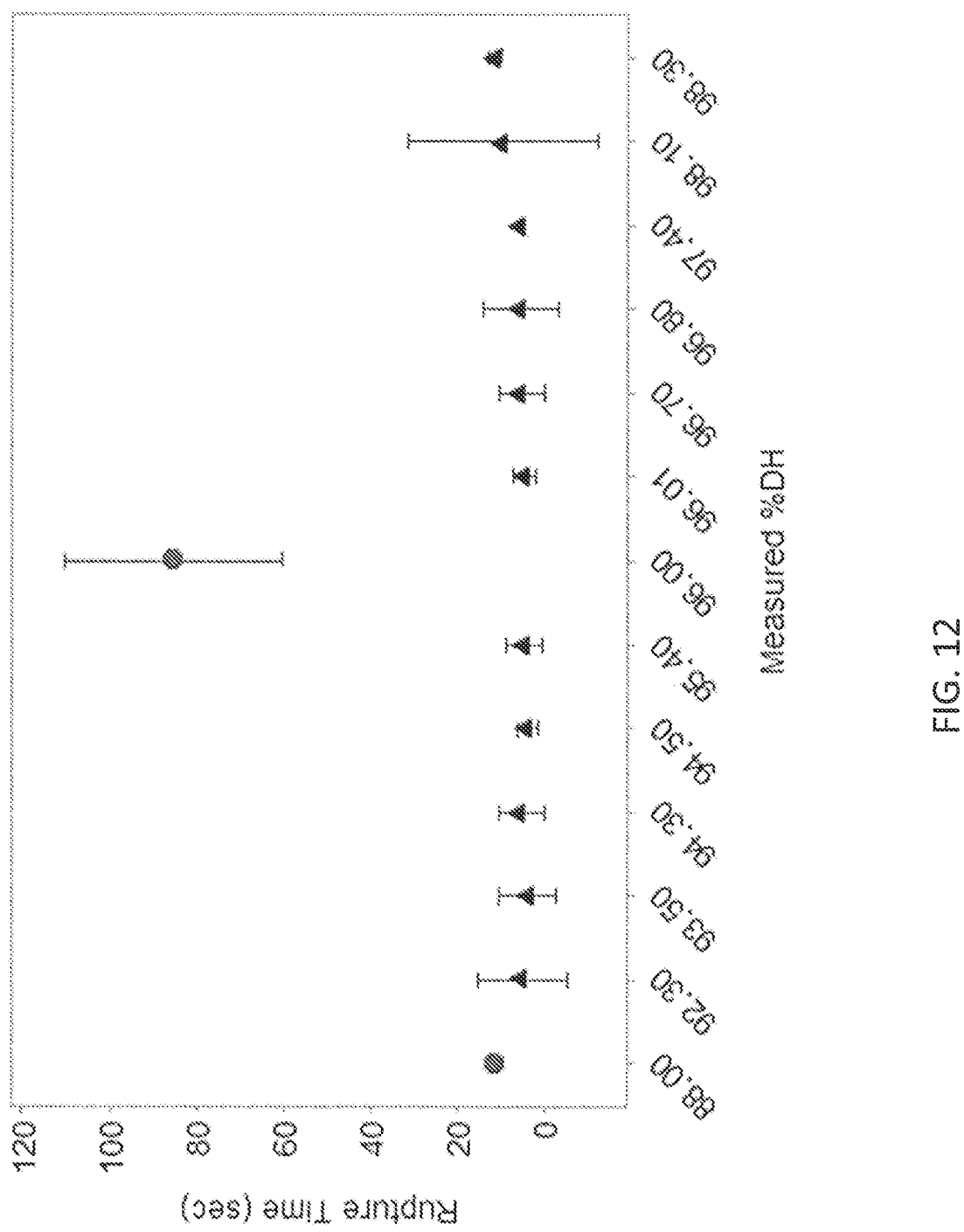
FIG. 12 shows rupture time (seconds) of nonwoven webs including fibers having different degrees of hydrolysis.
Figure 13:
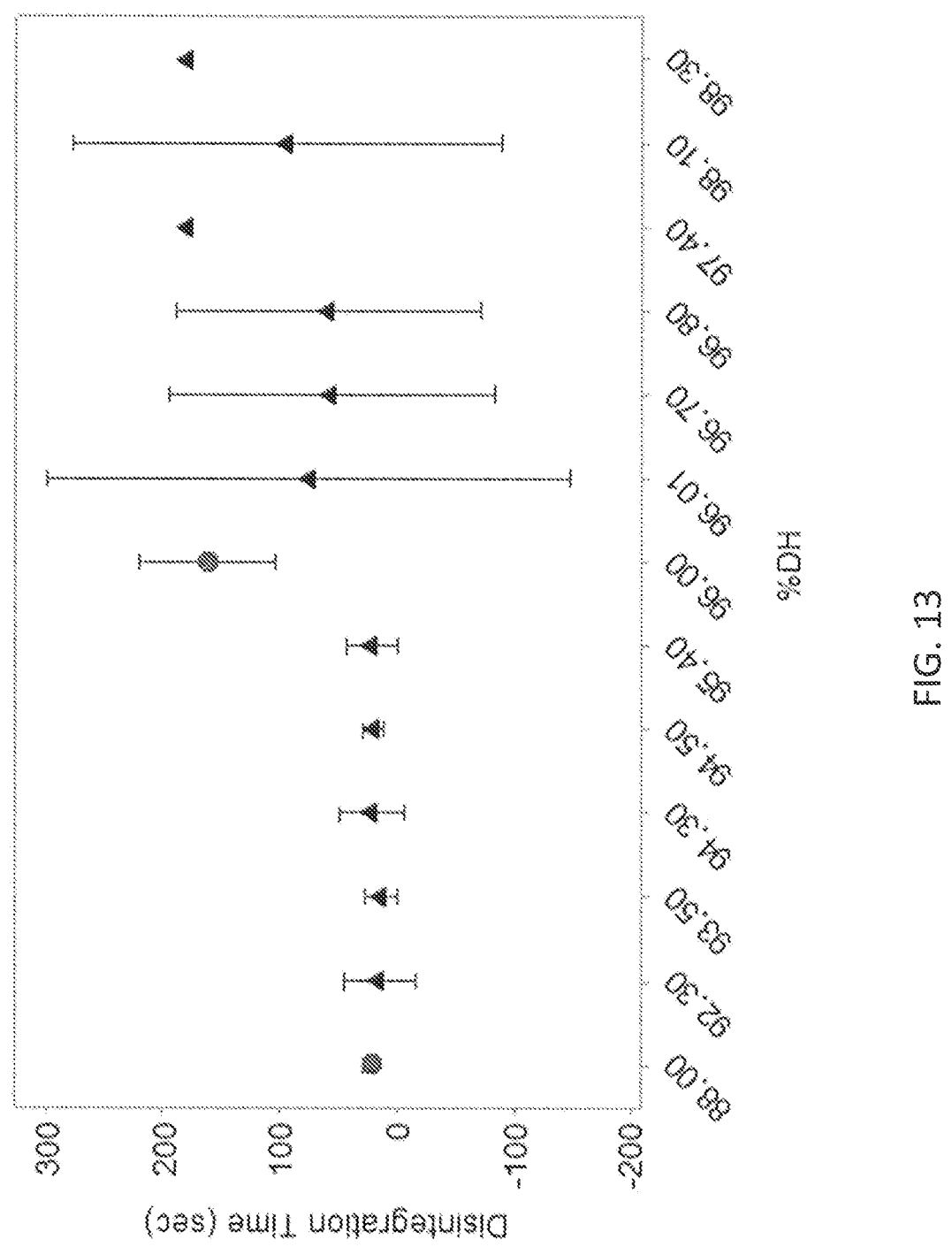
FIG. 13 shows disintegration time (seconds) of nonwoven webs including fibers having different degrees of hydrolysis.

FIG. 11 illustrates rupture time (seconds) and disintegration time (seconds) of a nonwoven web having an exemplary fiber (Fiber A) before and after exposed to heated methanol (e.g., at 50° C. for 10 minutes). FIGS. 12-13 show rupture time and disintegration time of nonwoven webs including fibers having different degrees of hydrolysis. Compared to untreated nonwoven webs, the treated or modified nonwoven webs with similar or higher measured degree of hydrolysis show improved solubility. The comparative examples having higher degree of hydrolysis may show gelling and may not be dissolved in water. However, the modified fibers and nonwoven structures having high degree of hydrolysis are dissolvable in water. The modified fibers and nonwoven structures break apart prior to gelation, as opposed to Comparative Example 5 (Fiber B nonwoven webs).

In Table 5, the softness data is rated from 1 (rough) to 5 (soft). The three samples tested show much higher softness than the Comparative Examples without treatment.

Examples 35-46

Figure 14:
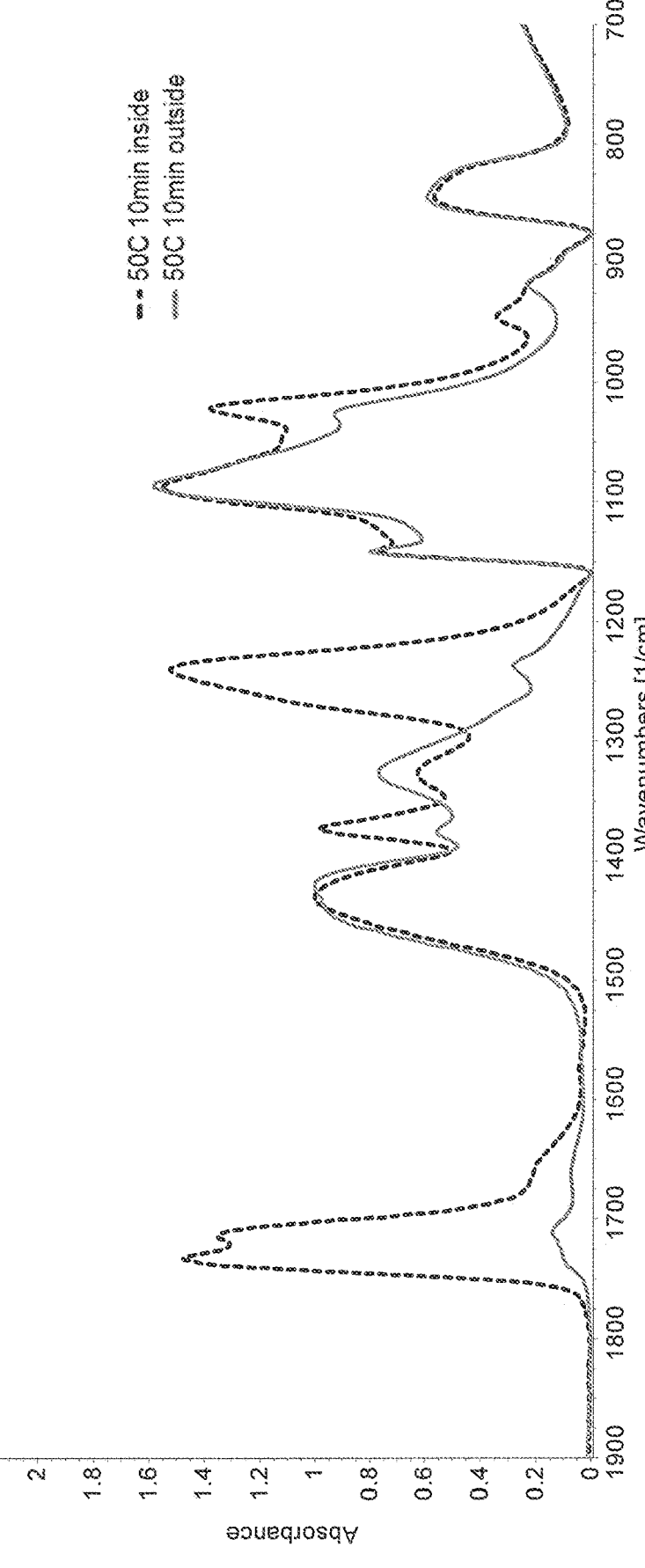
FIG. 14 shows ATR-FTIR results of an interior ("inside") region and a surface ("outside") region of an exemplary block comprising a copolymer of vinyl acetate and vinyl alcohol.

Table 6 shows the reaction conditions and the results of Examples 35-46, which are treated block samples. The block samples were made of a copolymer of vinyl acetate and vinyl alcohol having a degree of hydrolysis being 88%. These samples were treated with KOH. Each block sample had a size of 1.5 centimeters (cm)×1.5 cm×0.5 cm. After treated and dried, a sample having a thickness in a range of from 0.1 mm to 0.5 mm is cut from the block sample and then tested using ATR-FTIR. The results include degree of hydrolysis values in the interior ("inner") region and the surface ("outer") region. FIG. 14 shows the respective

TABLE 6

| Example No. (Block) | Batch Reaction Conditions: 0.05M KOH/NaOH | | % DH Outer Region Average | % DH Inner Region Average |
| | Temp (° C.) | Time (min) | | |
|---|---|---|---|---|
| No. 35 | 40 | 1 | 92 | 89.9 |
| No. 36 | | 2 | 93 | 89.5 |
| No. 37 | | 5 | 96.5 | 89.1 |
| No. 38 | | 10 | 98.4 | 89.5 |
| No. 39 | 50 | 1 | 93.4 | 89.6 |
| No. 40 | | 2 | 96 | 89.3 |
| No. 41 | | 5 | 98 | 89.2 |
| No. 42 | | 10 | 99.1 | 89.4 |
| No. 43 | 60 | 1 | 96 | 89.4 |
| No. 44 | | 2 | 98 | 89.4 |
| No. 45 | | 5 | 98.8 | 89.3 |
| No. 46 | | 10 | 99.3 | 89.8 |

The foregoing description is given for clearness of understanding only, and no unnecessary limitations should be understood therefrom, as modifications within the scope of the disclosure may be apparent to those having ordinary skill in the art.

All patents, publications and references cited herein are hereby fully incorporated by reference. In case of conflict between the present disclosure and incorporated patents, publications and references, the present disclosure should control.

What is claimed is:

1. A method of treating a fiber, said method comprising:
   admixing a fiber comprising a polymer comprising at least one of a vinyl acetate moiety or a vinyl alcohol moiety and having a degree of hydrolysis less than 100% with a hydrolysis agent solution to form a mixture so as to increase the degree of hydrolysis of at least a portion of the fiber, wherein the fiber does not dissolve in the hydrolysis agent solution and admixing a fiber increases the degree of hydrolysis of at least a portion of the fiber, wherein admixing a fiber with the hydrolysis agent solution is performed under conditions sufficient to provide a post-process fiber having a transverse cross-section with an increasing gradient in the degree of hydrolysis from an interior region of the post-process fiber to a surface region of the post-process fiber.

2. The method according to claim 1, further comprising heating the mixture of the fiber and the hydrolysis agent solution.

3. The method according to claim 1, wherein the fiber is admixed with the hydrolysis agent solution under conditions sufficient to provide at least one of a predetermined degree of hydrolysis or a predetermined degree of hydrolysis increase to the at least a portion of the fiber.

4. The method according to claim 1, wherein the fiber is admixed with the hydrolysis agent solution for a period of time in a range of from 1 minute to 48 hours.

5. The method according to claim 1, wherein the fiber is admixed with the hydrolysis agent solution at a temperature in a range of 10° C. to 100° C.

6. The method according to claim 1, wherein the polymer has a degree of hydrolysis greater than 79% and less than 96% prior to admixing the fiber with the hydrolysis agent solution.

7. The method according to claim 1, wherein the fiber is water-soluble after admixing the fiber with the hydrolysis agent solution.

8. The method according to claim 1, wherein the hydrolysis agent solution comprises a hydrolysis agent and a solvent.

9. The method according to claim 8, wherein the hydrolysis agent comprises a metallic hydroxide, a metal hydride, a sulfite, sulfur dioxide, a dithionate, a thiosulfate, a hydrazine, oxalic acid, formic acid, ascorbic acid, dithiothreitol, a phosphite, a dihypophosphite, phosphorous acid, sulfuric acid, sulphonic acid, hydrochloric acid, ammonium hydroxide, water, or combinations thereof.

10. The method according to claim 8, wherein the hydrolysis agent comprises a metallic hydroxide.

11. The method according to claim 10, wherein the metallic hydroxide comprises an alkali metal hydroxide, an alkaline earth metal hydroxide, a main group metal hydroxide, or combinations thereof.

12. The method according to claim 8, wherein the hydrolysis agent comprises sodium hydroxide, potassium hydroxide, calcium hydroxide, barium hydroxide, trialkyltin hydroxide, or combinations thereof.

13. The method according to claim 8, wherein the hydrolysis agent is provided in an amount of 0.2% (w/w) to 75% (w/w) based on a weight of the solvent.

14. The method according to claim 8, wherein the fiber is not soluble in the solvent.

15. The method according to claim 8, wherein the solvent comprises a polar solvent.

16. The method according to claim 8, wherein the solvent comprises one or more solvents selected from the group consisting of: n-propanol, acetone, ethanol, N-methylpyrrolidone, methanol, acetonitrile, N,N-dimethylformamide, dimethyl sulfoxide, formic acid, water, and combinations thereof.

17. The method according to claim 8, wherein the solvent comprises a nonpolar solvent.

18. The method according to claim 8, wherein the solvent comprises an alcohol that is a liquid under admixing conditions.

19. The method according to claim 8, wherein the solvent comprises a mixture of a first solvent and a second solvent.

20. The method according to claim 19, wherein the first solvent comprises a polar solvent and the second solvent comprises a nonpolar solvent.

21. The method according to claim 19, wherein the first solvent has a first dielectric constant and the second solvent has a second dielectric constant and the first dielectric constant is higher than the second dielectric constant.

22. The method according to claim 21, wherein a difference between the first dielectric constant and the second dielectric constant is at least 3.

23. The method according to claim 1, further comprising admixing an activator with the fiber and the hydrolysis agent solution.

24. The method according to claim 1, wherein the polymer comprises at least one of a vinyl acetate moiety or a vinyl alcohol moiety comprising a polyvinyl alcohol homopolymer, a polyvinyl acetate homopolymer, a polyvinyl alcohol copolymer, or combinations thereof.

25. The method according to claim 24, wherein the polyvinyl alcohol copolymer is a copolymer of vinyl acetate and vinyl alcohol.

26. The method according to claim 24, wherein the polyvinyl alcohol copolymer comprises an anionically modified copolymer.

27. The method according to claim 26, wherein the anionically modified copolymer comprises a carboxylate, a sulfonate, or combinations thereof.

28. The method according to claim 1, wherein the fiber further comprises an additional polymer.

29. The method according to claim 28, wherein the additional polymer is selected from the group consisting of: polyvinyl alcohol, polyvinyl acetate, polyacrylate, a water-soluble acrylate copolymer, polyvinyl pyrrolidone, polyethylenimine, pullulan, guar gum, gum Acacia, xanthan gum, carrageenan, starch, modified starch, polyalkylene oxide, polyacrylamide, polyacrylic acid, cellulose, cellulose ether, cellulose ester, cellulose amide, polycarboxylic acid, polyaminoacid, polyamide, a gelatin, dextrin, copolymers of the foregoing, and combinations of any of the foregoing additional polymers or copolymers.

30. The method according to claim 1, wherein admixing the fiber with the hydrolysis agent solution is performed under conditions sufficient to provide the post-process fiber having the transverse cross-section having a structure including a core and a sheath, wherein the core comprises the polymer with a first degree of hydrolysis and the sheath comprises the polymer with a second degree of hydrolysis greater than the first degree of hydrolysis.

31. The method according to claim 1, wherein the hydrolysis agent solution comprises sodium hydroxide and methanol, and admixing comprises immersing the fiber in the hydrolysis agent solution, and heating the mixture of the fiber in the hydrolysis agent solution to a temperature of 30° C. to 60° C. for 1 minute to 24 hours.

32. The method according to claim 1, wherein the fiber comprises a copolymer of vinyl alcohol and vinyl acetate having a degree of hydrolysis of 88%, 92%, or 96%, the hydrolysis agent solution comprises sodium hydroxide and methanol, and admixing comprises immersing the fiber in the hydrolysis agent solution, and heating the mixture of the fiber in the hydrolysis agent solution to a temperature of 30° C. to 60° C. for 12 hours to 24 hours.

33. The method according to claim 1, wherein the fiber comprises an anionically modified copolymer having a carboxylate or sulfonate modification and a degree of hydrolysis of 88%, 92%, or 96%, the hydrolysis agent solution comprises sodium hydroxide and methanol, and admixing comprises immersing the fiber in the hydrolysis agent solution, and heating the mixture of the fiber in the hydrolysis agent solution to a temperature of 30° C. to 60° C. for 12 hours to 24 hours.

34. The method according to claim 1, wherein the fiber comprises a copolymer of vinyl alcohol and vinyl acetate having a degree of hydrolysis of 88%, 92%, or 96%, the hydrolysis agent solution comprises sodium hydroxide and methanol, and admixing comprises immersing the fiber in the hydrolysis agent solution, and heating the mixture of the fiber in the hydrolysis agent solution to a temperature of 30° C. to 60° C. for 1 hour to 12 hours.

35. The method according to claim 1, wherein the fiber comprises an anionically modified copolymer having a carboxylate or sulfonate modification and a degree of hydrolysis of 88%, 92%, or 96%, the hydrolysis agent solution comprises sodium hydroxide and methanol, and admixing a fiber comprises immersing the fiber in the hydrolysis agent solution, and heating the mixture of the fiber in the hydrolysis agent solution to a temperature of 30° C. to 60° C. for 1 hour to 12 hours.

36. The method according to claim 1, wherein the fiber comprises a copolymer of vinyl alcohol and vinyl acetate having a degree of hydrolysis of 88%, 92%, or 96%, the hydrolysis agent solution comprises sodium hydroxide and methanol, and admixing comprises immersing the fiber in the hydrolysis agent solution, and heating the mixture of the fiber in the hydrolysis agent solution to a temperature of 30° C. to 60° C. for up to 1 hour.

37. The method according to claim 1, wherein the fiber comprises an anionically modified copolymer having a carboxylate or sulfonate modification and a degree of hydrolysis of 88%, 92%, or 96%, the hydrolysis agent solution comprises sodium hydroxide and methanol, and admixing comprises immersing the fiber in the hydrolysis agent solution, and heating the mixture of the fiber in the hydrolysis agent solution to a temperature of 30° C. to 60° C. for up to 1 hour.

38. The method of claim 1, further comprising:
contacting a surface of the fiber with the hydrolysis agent solution to increase the degree of hydrolysis of the polymer at the surface of the fiber.

39. The method according to claim 38, wherein contacting a surface of the fiber with the hydrolysis agent solution comprises immersion, spraying, transfer coating, wicking, foaming, brushing, rolling, humidification, vapor deposition, printing, or combinations thereof.

40. The method according to claim 38, wherein contacting a surface of the fiber with the hydrolysis agent solution is performed after formation of the fiber as part of a continuous inline process.

41. The method according to claim 38, wherein contacting a surface of the fiber with the hydrolysis agent solution is performed while the fiber is in motion.

42. The method according to claim 38, wherein contacting a surface of the fiber with the hydrolysis agent solution is performed in a batch by a batch process.

43. The method according to claim 38, wherein the fiber comprises at least one of a staple fiber, a staple yarn, a fiber fill, needle punch fabrics, bonding fibers, or combinations thereof.

\* \* \* \* \*